(12) United States Patent
Zhou et al.

(10) Patent No.: US 12,071,439 B2
(45) Date of Patent: Aug. 27, 2024

(54) PROCESS AND INTERMEDIATES FOR PREPARING A JAK INHIBITOR

(71) Applicant: Incyte Corporation, Wilmington, DE (US)

(72) Inventors: Jiacheng Zhou, Newark, DE (US); Shili Chen, Newark, DE (US); Zhongjiang Jia, Kennett Square, PA (US); Pingli Liu, Wilmington, DE (US); David Meloni, Bear, DE (US); Yongchun Pan, Wilmington, DE (US); Naijing Su, Hockessin, DE (US); Michael Xia, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/861,597

(22) Filed: Jul. 11, 2022

(65) Prior Publication Data

US 2023/0059389 A1 Feb. 23, 2023

Related U.S. Application Data

(60) Provisional application No. 63/220,752, filed on Jul. 12, 2021.

(51) Int. Cl.
*C07D 487/04* (2006.01)
*C07D 205/04* (2006.01)

(52) U.S. Cl.
CPC ......... *C07D 487/04* (2013.01); *C07D 205/04* (2013.01)

(58) Field of Classification Search
CPC ............................ C07D 487/04; A61K 31/519
USPC ........................................ 544/280; 514/265.1
See application file for complete search history.

(56) References Cited

U.S. PATENT DOCUMENTS

| | | | |
|---|---|---|---|
| 7,335,667 B2 | 2/2008 | Rodgers et al. |
| 7,598,257 B2 | 10/2009 | Rodgers et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,445,488 B2 | 5/2013 | Rodgers et al. |
| 8,486,902 B2 | 7/2013 | Rodgers et al. |
| 8,530,485 B2 | 9/2013 | Rodgers et al. |
| 8,541,425 B2 | 9/2013 | Rodgers et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,883,806 B2 | 11/2014 | Zhou |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,443 B2 | 3/2015 | Liu et al. |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,193,733 B2 | 11/2015 | Rodgers et al. |
| 9,206,187 B2 | 12/2015 | Rodgers et al. |
| 9,216,984 B2 | 12/2015 | Li et al. |
| 9,221,845 B2 | 12/2015 | Cao |
| 9,249,145 B2 | 2/2016 | Rodgers et al. |
| 9,290,506 B2 | 3/2016 | Zhou et al. |
| 9,334,274 B2 | 5/2016 | Rodgers et al. |
| 9,359,358 B2 | 6/2016 | Rodgers et al. |
| 9,376,439 B2 | 6/2016 | Rodgers et al. |
| 9,382,231 B2 | 7/2016 | Li et al. |
| 9,464,088 B2 | 10/2016 | Huang et al. |
| 9,487,521 B2 | 11/2016 | Zhou et al. |
| 9,512,161 B2 | 12/2016 | Rodgers et al. |
| 9,580,419 B2 | 2/2017 | Rodgers et al. |
| 9,611,269 B2 | 4/2017 | Yao et al. |
| 9,623,029 B2 | 4/2017 | Li et al. |
| 9,662,335 B2 | 5/2017 | Rodgers et al. |
| 9,714,233 B2 | 7/2017 | Liu et al. |
| 9,718,834 B2 | 8/2017 | Zhou et al. |
| 9,802,957 B2 | 10/2017 | Zhou et al. |
| 9,814,722 B2 | 11/2017 | Rodgers et al. |

(Continued)

FOREIGN PATENT DOCUMENTS

| | | |
|---|---|---|
| CA | 2928286 | 10/2016 |
| CN | 106397443 | 2/2017 |

(Continued)

OTHER PUBLICATIONS

International Preliminary Report on Patentability in International Application No. PCT/US2021/046286, dated Mar. 2, 2023, 9 pages.
International Preliminary Report on Patentability in International Application No. PCT/US2021/046298, dated Mar. 2, 2023, 7 pages.
Aleksanyan et al., "Synthesis and transformations of novel formyl 1-substituted quinolines," Heterocycl Commun., Jan. 1, 2011, 17(3-4):105-110.
Arnold, "Synthetic Reactions of Dimethyl Formamide," Collect Czech Chem Comm., 1963, 28:863-868 (English Abstract).

(Continued)

*Primary Examiner* — Jeffrey H Murray
(74) *Attorney, Agent, or Firm* — Fish & Richardson P.C.

(57) ABSTRACT

The present disclosure is related to processes for preparing baricitinib, salts thereof, and related synthetic intermediate compounds and salts thereof.

31 Claims, 9 Drawing Sheets

(56) References Cited

U.S. PATENT DOCUMENTS

| | | |
|---|---|---|
| 9,879,010 B2 | 1/2018 | Rodgers et al. |
| 9,908,888 B2 | 3/2018 | Zhou et al. |
| 9,926,301 B2 | 3/2018 | Li et al. |
| 9,974,790 B2 | 5/2018 | Rodgers et al. |
| 9,999,619 B2 | 6/2018 | Huang et al. |
| 10,016,429 B2 | 7/2018 | Rodgers et al. |
| 10,166,191 B2 | 1/2019 | Ni et al. |
| 10,364,248 B2 | 7/2019 | Zhou et al. |
| 10,398,699 B2 | 9/2019 | Rodgers et al. |
| 10,428,104 B2 | 10/2019 | Tatlock et al. |
| 10,435,392 B2 | 10/2019 | Li et al. |
| 10,450,325 B2 | 10/2019 | Zhou et al. |
| 10,463,667 B2 | 11/2019 | Rodgers et al. |
| 10,513,522 B2 | 12/2019 | Yao et al. |
| 10,562,904 B2 | 2/2020 | Zhang et al. |
| 10,610,530 B2 | 4/2020 | Li et al. |
| 10,639,310 B2 | 5/2020 | Rodgers et al. |
| 10,640,506 B2 | 5/2020 | Rodgers et al. |
| 10,695,337 B2 | 6/2020 | Huang et al. |
| 10,758,543 B2 | 9/2020 | Parikh et al. |
| 10,766,900 B2 | 9/2020 | Lai |
| 10,869,870 B2 | 12/2020 | Parikh et al. |
| 10,874,616 B2 | 12/2020 | Ni et al. |
| 10,899,736 B2 | 1/2021 | Wang et al. |
| 10,975,085 B2 | 4/2021 | Zhou et al. |
| 11,001,571 B2 | 5/2021 | Li et al. |
| 11,213,528 B2 | 1/2022 | Li et al. |
| 11,214,573 B2 | 1/2022 | Yao et al. |
| 11,219,624 B2 | 1/2022 | Parikh et al. |
| 11,285,140 B2 | 3/2022 | Huang et al. |
| 11,331,320 B2 | 5/2022 | Rodgers et al. |
| 11,337,927 B2 | 5/2022 | Ni et al. |
| 11,897,889 B2 | 2/2024 | Zhou et al. |
| 11,905,292 B2 | 2/2024 | Zhou et al. |
| 2007/0135461 A1 | 6/2007 | Rodgers et al. |
| 2008/0312259 A1 | 12/2008 | Rodgers et al. |
| 2009/0233903 A1 | 9/2009 | Rodgers et al. |
| 2010/0190981 A1 | 7/2010 | Zhou et al. |
| 2011/0224190 A1 | 9/2011 | Huang et al. |
| 2012/0022058 A1 | 1/2012 | Arhancet et al. |
| 2013/0060026 A1 | 3/2013 | Zhou et al. |
| 2014/0256941 A1 | 9/2014 | Liu et al. |
| 2015/0087632 A1 | 3/2015 | Rodgers et al. |
| 2015/0065484 A1 | 10/2015 | Yeleswaram et al. |
| 2019/0023712 A1 | 1/2019 | Zhang et al. |
| 2019/0169200 A1 | 6/2019 | Pan et al. |
| 2019/0211021 A1 | 7/2019 | Zhang et al. |
| 2019/0233392 A1 | 8/2019 | Wang et al. |
| 2021/0238168 A1 | 8/2021 | Li et al. |
| 2022/0056034 A1 | 2/2022 | Zhou et al. |
| 2022/0056035 A1 | 2/2022 | Zhou et al. |

FOREIGN PATENT DOCUMENTS

| | | |
|---|---|---|
| CN | 107759601 | 3/2018 |
| CN | 107759623 | 3/2018 |
| CN | 109651424 | 4/2019 |
| CN | 110003216 | 7/2019 |
| CN | 110724145 | 1/2020 |
| CN | 113480546 | 10/2021 |
| EP | 434940 | 7/1991 |
| EP | 2398774 | 12/2011 |
| EP | 3262057 | 1/2018 |
| EP | 3398952 | 11/2018 |
| GB | 812366 | 4/1959 |
| IN | 2015CH05639 | 4/2017 |
| IN | 201641026603 | 2/2018 |
| WO | WO 2004021979 | 3/2004 |
| WO | WO 2005116035 | 12/2005 |
| WO | WO 2007012953 | 2/2007 |
| WO | WO 2007092213 | 8/2007 |
| WO | WO 2009016460 | 2/2009 |
| WO | WO 2010039939 | 4/2010 |
| WO | WO 2010083283 | 7/2010 |
| WO | WO 2010116282 | 10/2010 |
| WO | WO 2011057022 | 5/2011 |
| WO | WO 2011063159 | 5/2011 |
| WO | WO 2011103423 | 8/2011 |
| WO | WO 2011133637 | 10/2011 |
| WO | WO 2013024895 | 2/2013 |
| WO | WO 2016026974 | 2/2016 |
| WO | WO 2016026975 | 2/2016 |
| WO | WO 2016035014 | 3/2016 |
| WO | WO 2016063294 | 4/2016 |
| WO | WO 2016135582 | 9/2016 |
| WO | WO 2017032349 | 3/2017 |
| WO | WO 2017106957 | 6/2017 |
| WO | WO 2017114461 | 7/2017 |
| WO | WO 2017125097 | 7/2017 |
| WO | WO 2018055097 | 3/2018 |
| WO | WO 2019224677 | 11/2019 |
| WO | WO 2020163653 | 8/2020 |
| WO | WO 2022040172 | 2/2022 |

OTHER PUBLICATIONS

Arnold, "Synthetic reactions of dimethylformamide. XV. Synthesis of symmetrical tetraformylethane," Collect Czech Chem Comm., 1962, 27:2993-2995.

Berge et al., "Pharmaceutical Salts," Journal of Pharmaceutical Science, 1977, 66:1-19.

Blume-Jensen P. et al., "Oncogenic kinase signalling," Nature, 2001, 411(6835):355-365.

Borrell et al., "Design and synthesis of two pyrazole libraries based on o-hydroxyacetophenones," Mol Divers., 2004, 8(2):147-157.

Bredereck et al., "Reactions of Activated Methyl Groups Attached to Heterocycles," Agnew Chem Internat Edit., 1963, 2(12):738.

Brown et al., "Vilsmeier Reaction on 6-Methylpurine," J Chem Soc., 1971, 0:128-132.

CAS No. 945950-37-8 "4-Methyl-7H-pyrrolo[2,3-d]pyrimidine," Chemical Book, retrieved on Mar. 9, 2021, retrieved from URL <https://www.chemicalbook.com/CASEN_945950-37-8.htm>, 3 pages.

Ciernik, "Formylation of Nitrogen-containing heterocycles and their quaternary salts,"Collection Czechoslov Chem., 1972, 37:2273-2281 (English Abstract).

Doohan et al., "The photomediated reaction of alkynes with cycloalkanes," Organic & Biomolecular Chemistry., 2006, 4(5):942-952.

Greene et al., "Protective Groups in Organic Synthesis," 4d Ed., Wiley & Sons, 2007, 1111 pages.

Gupton et al., "Preparation of indole containing building blocks for the regiospecific construction of indole appended pyrazoles and pyrroles, " Tetrahedron, Jul. 1, 2013, 69(29):5829-5840.

International Search Report and Written Opinion in International Application No. PCT/US2021/046286, dated Nov. 9, 2021, 17 pages.

International Search Report and Written Opinion in International Application No. PCT/US2021/046298, dated Nov. 11, 2021, 14 pages.

International Search Report and Written Opinion in International Application No. PCT/US2022/073599, dated Sep. 30, 2022, 18 pages.

Jones et al., "The Vilsmeier Reaction of Non-Aromatic Compounds," Organic Reactions, Hoboken, NJ, 2000, vol. 56, Ch. 2, pp. 355-659.

Kobor et al., "Synthesis of Acetic Acid, Propionic and Aminomethyl Theophylline Darivatives Substituted at Position 8," A Juhász Gyula Tanárképző Főiskola tudományos közleményei, 1977, pp. 31-40 (English Abstract).

Li et al., "Synthesis of INCB018424 with High ee Value," Hecheng Huaxue, 2011, 19(2):280-282 (English Abstract).

Lin et al., "Enantioselective synthesis of Janus kinase inhibitor INCB018424 via an organocatalytic aza-Michael reaction," Organic Letters, May 2009, 11(9):1999-2002.

Mulyana et al., "New cobalt(II) and zinc(II) coordination frameworks incorporating a pyridyl-pyrazole ditopic ligand," Dalton Translations, 2005, 9:1598-1601.

(56) References Cited

OTHER PUBLICATIONS

Ooms et al., "Chemistry of Tetra-alkoxyethenes. Part V1.1 Cycloadditions with ag-Unsaturated Carbonyl Compounds and Chemistry of the Resulting Tetra-alkoxydihydropyrans," Journal of the Chemical Society, Perkin Transactions 1: Organic and Bio-Organic Chemistry, 1976, 14:1533-1538.
Ravin "Preformulation," Remington's Pharmaceutical Sciences, Mack Publishing Company, Easton, Pa., 1985,17th Ed., Chapter 76, pp. 1409-1423.
Saxena et al., "Synthesis and antiviral activity of certain 4-substituted and 2,4-disubstituted 7-[(2-hydroxyethoxy)methyl]pyrrolo[2,3-d]pyrimidines," Journal of Medicinal Chemistry, 1988, 31(8):1501-6.
Scott et al., "Jaks, STATs, Cytokines, and Sepsis." Clin Diagn Lab Immunol., 2002, 9(6):1153-1159.
Seus, "Vilsmeier Formylation of 4-Dimethylaminostilbene," J Org Chem., Aug. 1965, 30:2818-2821.
STN Reg No. 105-56-6, "Acetic acid, 2-cyano-, ethyl ester," dated Nov. 16, 1984, 1 page.
STN Reg No. 3473-63-0, "Methanimidamide, acetate," date Nov. 16, 1984, 1 page.
STN Reg No. 39929-79-8, "1H-Pyrrolo[2,3-d]pyrimidine-2,4(3H,7H)-dione," dated Nov. 16, 1984, 1 page.
STN Reg No. 5977-14-0, "Butanamide, 3-oxo-," dated Nov. 16, 1984, 1 page.
STN Reg No. 7252-83-7, "Ethane, 2-bromo-1,1-dimethoxy-," dated Nov. 16, 1984, 1 page.
STN Reg No. 873-83-6, "2,4(1H,3H)-Pyrimidinedione, 6-amino-," dated Nov. 16, 1984, 1 page.
STN Reg No. 90213-66-4, "7H-Pyrrolo[2,3-d]pyrimidine, 2,4-dichloro-," dated Nov. 16, 1984, 1 page.
STN Reg No. 933715-40-3, "5-Pyrimidineacetic acid, 4-amino-6-methyl-," dated Apr. 30, 2007, 1 page.
Thiyagarajan et al., "Structure based medicinal chemistry approach to develop 4-methyl-7-deazaadenine carbocyclic nucleosides as anti-HCV agent," Bioorganic & Medicinal Chemistry Letters, 2012, 22(24):7742-7747.
Wiest et al., "A Route to 2-Substituted 3-Cyanopyrroles: Synthesis of Danaidal and Suffrutine A," Journal of Organic Chemistry (2016), 81(14):6149-6156.
Eurasian Office Action in Eurasian Application No. 202390604, dated Feb. 29, 2024, 12 pages (with English Translation).
Eurasian Office Action in Eurasian Application No. 202390605, dated Mar. 20, 2024, 11 pages (with English Translation).
Georgian Office Action in Georgian Application No. AP 2021 16193, dated Jun. 23, 2023, 2 pages (with English Translation).
Georgian Office Action in Georgian Application No. AP 2021 16193, dated Oct. 20, 2023, 3 pages (with English Translation).
Gupton et al., "The preparation and some reactions of a benzotriazole substituted vinamidinium salt," Tetrahedron, Jan. 1993, 49(45):10205-18.
Saudi Arabian Office Action in Saudi Arabian Application No. 523442595, dated Dec. 17, 2023, 11 pages (with English Translation).
Sri Lankan Office Action in Sri Lankan Application No. 22590, dated Nov. 15, 2023, 1 page.

PROCESS AND INTERMEDIATES FOR PREPARING A JAK INHIBITOR

CROSS-REFERENCES TO RELATED APPLICATIONS

This application claims priority to U.S. Provisional Application No. 63/220,752, filed on Jul. 12, 2021, the content of which is incorporated herein in its entirety.

FIELD

The present disclosure is related to processes for preparing baricitinib, salts thereof, and related synthetic intermediate compounds and salts thereof. Baricitinib and salts thereof are useful as inhibitors of the Janus Kinase family of protein tyrosine kinases (JAKs) for treatment of inflammatory diseases, myeloproliferative disorders, and other diseases.

BACKGROUND

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P. et al., Nature 2001, 411(6835):355-365). Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. The Janus kinase family of protein tyrosine kinases (JAKs) belong to the non-receptor type of tyrosine kinases and include family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2).

The pathway involving JAKs and Signal Transducers and Activators of Transcription (STATs) is engaged in the signaling of a wide range of cytokines. Cytokines are low-molecular weight polypeptides or glycoproteins that stimulate biological responses in virtually all cell types. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "Jaks, STATs, Cytokines, and Sepsis." Clin Diagn Lab Immunol 9(6): 1153-9).

The JAK family plays a role in the cytokine-dependent regulation of proliferation and function of cells involved in immune response. The JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. Moreover, multiple cytokines that signal through JAK kinases have been linked to inflammatory diseases or conditions of the upper respiratory tract such as those affecting the nose and sinuses (e.g., rhinitis, sinusitis) whether classically allergic reactions or not. The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

Blocking signal transduction at the level of the JAK kinases holds promise for developing treatments for human cancers. Inhibition of the JAK is also envisioned to have therapeutic benefits in patients suffering from skin immune disorders such as atopic dermatitis, alopecia areata, psoriasis, and skin sensitization. Accordingly, JAK inhibitors are widely sought. For example, the JAK inhibitor, baricitinib, {1-(ethylsulfonyl)-3-[4-(7H-pyrrolo[2,3-d]pyrimidin-4-yl)-1H-pyrazol-1-yl]azetidin-3-yl}acetonitrile, is reported in U.S. Pat. No. 8,158,616, filed Mar. 10, 2009, which is incorporated herein by reference in its entirety.

In view of the growing demand for compounds for the treatment of disorders related to JAK inhibitors, new and more efficient routes to baricitinib, salts thereof, and intermediates related thereto, are needed. The processes and compounds described herein help meet these and other needs.

SUMMARY

The present disclosure provides, inter alia, processes of preparing baricitinib, comprising reacting a compound of formula 3:

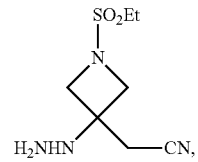

or a salt thereof, with a reagent selected from (i) a salt of formula 2a, or a salt thereof, and (ii) a compound of formula 2b:

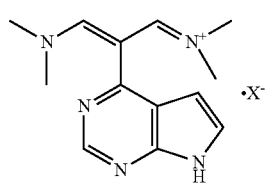

-continued

![Formula 2b: compound with OH, CHO groups on pyrrolopyrimidine]

2b wherein X⁻ is a counter anion.

The present disclosure also provides, inter alia, processes of preparing baricitinib, comprising reacting a compound of formula 3:

![Formula 3: azetidine with SO2Et, H2NHN, CN substituents]

3 or a salt thereof, with a reagent selected from (i) a salt of formula 2a, and (ii) a compound of formula 2b:

![Formula 2a: bis(dimethylamino)methylene compound on pyrrolopyrimidine with X⁻]

2a

![Formula 2b: compound with OH, CHO groups on pyrrolopyrimidine]

2b wherein X⁻ is a counter anion.

The present disclosure further provides a compound of formula 3:

![Formula 3: azetidine with SO2Et, H2NHN, CN substituents]

3 or a salt thereof.

The present disclosure also provides processes of making a compound of formula 3, or a salt thereof, comprising reacting a compound of formula 6:

with hydrazine.

![Formula 6: azetidine with SO2Et and =CHCN]

6

The present disclosure further provides processes of preparing baricitinib, or a salt thereof, comprising reacting a salt of formula 2c:

![Formula 2c: bis(dimethylamino)methylene compound on pyrrolopyrimidine with Cl⁻]

2c with a compound of formula 3:

![Formula 3: azetidine with SO2Et, H2NHN, CN substituents]

3 to form the baricitinib, or the salt thereof.

In some embodiments, the salt of formula 2c is prepared by a process comprising reacting a salt of formula 2d:

![Formula 2d: bis(dimethylamino)methylene compound on pyrrolopyrimidine with 2Cl⁻]

2d with a base to form the salt of formula 2c.

In some embodiments, the salt of formula 2d is prepared by a process comprising:

(a) reacting a compound of formula 2P:

[Structure 2P: 4-chloro-7H-pyrrolo[2,3-d]pyrimidine with P¹ on N]

with MeMgBr in the presence of a Grignard catalyst to form a compound of formula 1aP:

[Structure 1aP: 4-methyl-7H-pyrrolo[2,3-d]pyrimidine with P¹ on N]

(b) deprotecting the compound of formula 1 aP to form a compound of formula 1a:
or a salt thereof; and

[Structure 1a: 4-methyl-7H-pyrrolo[2,3-d]pyrimidine]

(c) reacting the compound of formula 1a, or the salt thereof, with a Vilsmeier reagent formed from dimethylformamide and a chlorinating agent to form the salt of formula 2d;

wherein P¹ is an amino protecting group.

In some embodiments, the salt of formula 2d is prepared by a process comprising:

(a) reacting a compound of formula 22P:

[Structure 22P: 2,4-dichloro-7H-pyrrolo[2,3-d]pyrimidine with P² on N]

with MeMgBr in the presence of a Grignard catalyst to form a compound of formula 23P:

[Structure 23P: 2-chloro-4-methyl-7H-pyrrolo[2,3-d]pyrimidine with P² on N]

(b) reducing the compound of formula 23P to form a compound of formula 1a:
or a salt thereof; and

[Structure 1a: 4-methyl-7H-pyrrolo[2,3-d]pyrimidine]

(c) reacting the compound of formula 1a, or the salt thereof, with a Vilsmeier reagent formed from dimethylformamide and a chlorinating agent to form the salt of formula 2d;

wherein P² is an amino protecting group.

In some embodiments, the compound of formula 3, or the salt thereof, is prepared by a process comprising:
reacting a compound of formula 6:
with hydrazine.

[Structure 6: azetidine with SO₂Et on N and =CH-CN exocyclic]

The details of one or more embodiments of the invention are set forth in the accompanying drawings and the detailed description below.

DETAILED DESCRIPTION

Figure 1:
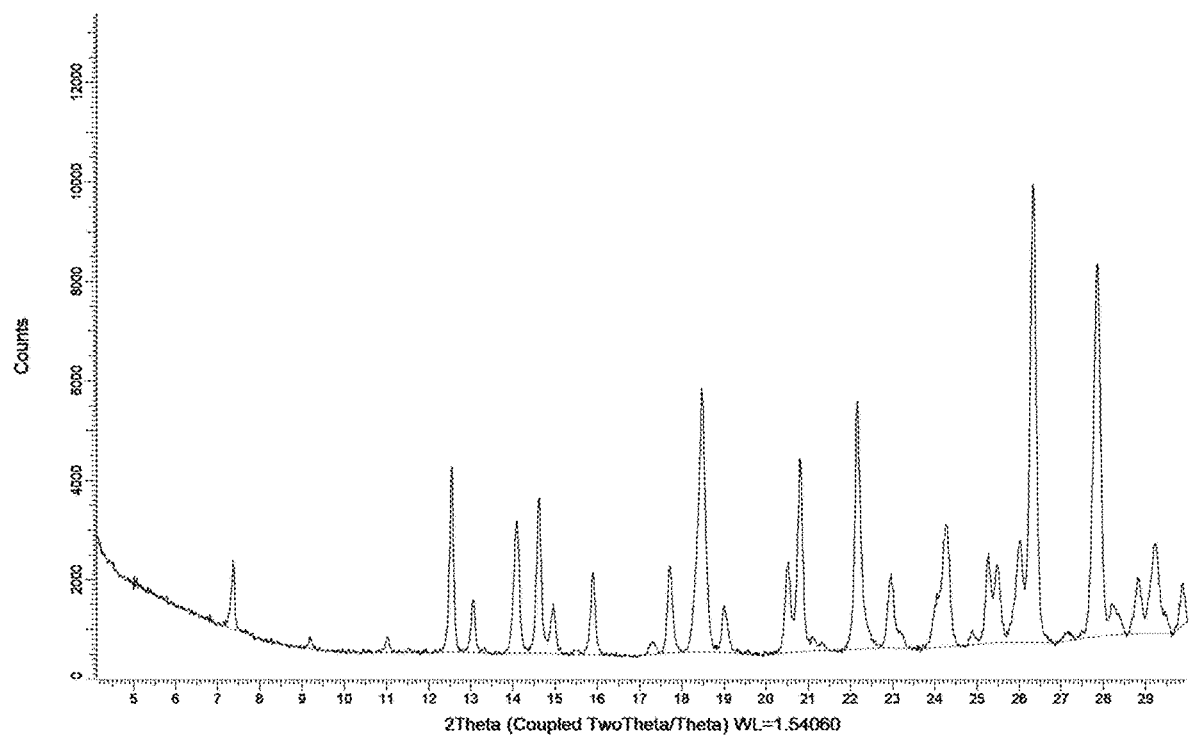
FIG. 1 is an X-ray powder diffraction (XRPD) pattern of Compound 2d Form I.

The present disclosure provides processes of preparing baricitinib, also known as {1-(ethylsulfonyl)-3-14-(7H-pyrrolo[2,3-d]pyrimidin-4-yl)-1H-pyrazol-1-yl]azetidin-3-yl}acetonitrile, and intermediates used in the process thereto. Baricitinib has the following structure:

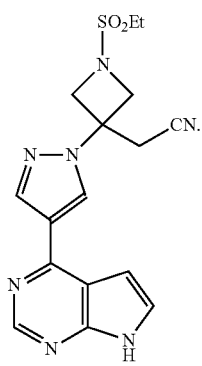

Compound 1

Baricitinib is also referred to as Compound 1 in this disclosure. The compound and various processes of preparing the compound are disclosed in U.S. Pat. No. 8,158,616, filed Mar. 10, 2009, which is incorporated herein by reference in its entirety.

In some embodiments, provided herein is a process of preparing baricitinib, or a salt thereof, comprising reacting a compound of formula 3:

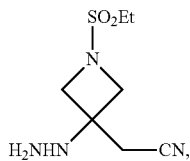

3 or a salt thereof, with a reagent selected from (i) a salt of formula 2a, or a salt thereof, and (ii) a compound of formula 2b:

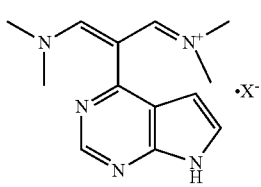

2a

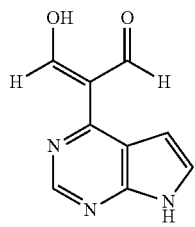

2b wherein X⁻ is a counter anion.

In some embodiments, the present disclosure provides a process of preparing baricitinib, or a salt thereof, comprising reacting a compound of formula 3:

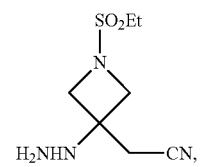

3 or a salt thereof, with a reagent selected from (i) a salt of formula 2a, and (ii) a compound of formula 2b:

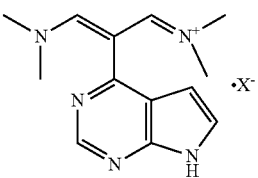

2a

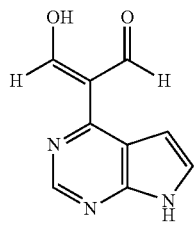

2b wherein X⁻ is a counter anion.

In some embodiments, from about 1 to about 1.5 molar equivalent of the reagent ((i) a salt of formula 2a, or a salt thereof, or (ii) a compound of formula 2b) is utilized relative to the compound of formula 3, or salt thereof. In some embodiments, about 1.25 molar equivalent of the reagent is utilized relative to the compound of formula 3, or salt thereof. In some embodiments, about 1 molar equivalent of the reagent is utilized relative to the compound of formula 3, or salt thereof.

In some embodiments, the reacting of the reagent ((i) a salt of formula 2a, or a salt thereof, or (ii) a compound of formula 2b) with the compound of formula 3, or a salt thereof, is carried out in a solvent component. The solvent component can comprise a polar protic solvent or a polar aprotic solvent. In some embodiments, solvent component comprises water. In some embodiments, the solvent component comprises an alcohol. In some embodiments, the solvent component comprises formula $C_{1-6}$ alkyl-OH. In some embodiments, the solvent component is ethanol. In some embodiments, the solvent component comprises dimethylformamide. In some embodiments, the solvent component comprises water, an alcohol or a combination thereof.

In some embodiments, the reagent is a salt of formula 2a. In some embodiments, the reagent is a salt of a salt of formula 2a (e.g., a hydrochloric acid salt of a salt of formula 2a). In some embodiments, the reagent is the hydrochloric acid salt of the salt of formula 2a. In some embodiments, the hydrochloric acid salt of the salt of formula 2a is a salt of formula 2d:

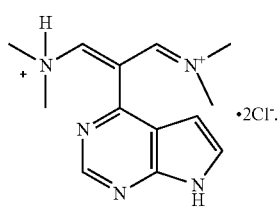

2d

In some embodiments, X⁻ is selected from Cl⁻, Br⁻, I⁻, $BF_4^-$, $PF_6^-$, $AsF_6^-$, $SbF_6^-$, and $ClO_4^-$. In some embodiments, X⁻ is selected from Cl⁻, $BF_4^-$, $PF_6^-$, $AsF_6^-$, $SbF_6^-$, and $ClO_4^-$. In some embodiments, X⁻ is $BF_4^-$. In some embodiments, X⁻ is $PF_6^-$. In some embodiments, X⁻ is $AsF_6^-$. In some embodiments, X⁻ is $SbF_6^-$. In some embodiments, X⁻ is $ClO_4^-$. In some embodiments, X⁻ is Cl⁻.

In some embodiments, from about 1 to about 2 molar equivalent of the reagent, which is a salt of formula 2d, is utilized relative to the compound of formula 3, or salt thereof. In some embodiments, about 1.5 molar equivalent of the reagent is utilized relative to the compound of formula 3, or salt thereof. In some embodiments, about 1 molar equivalent of the reagent is utilized relative to the compound of formula 3, or salt thereof.

In some embodiments, the reacting of the reagent ((i) a salt of formula 2a, or a salt thereof, or (ii) a compound of formula 2b) with the compound of formula 3, or the salt thereof, is carried out in a solvent component. The solvent component can comprise a polar protic solvent or a polar aprotic solvent. In some embodiments, the solvent component comprises water. In some embodiments, the solvent component comprises an alcohol. In some embodiments, the solvent component comprises a compound of formula $C_{1-6}$ alkyl-OH. In some embodiments, the solvent component is ethanol. In some embodiments, the solvent component comprises dimethylformamide. In some embodiments, the solvent component comprises water, an alcohol or a combination thereof.

In some embodiments, the reagent is the compound of formula 2b. In some embodiments, the compound of formula 2b is prepared by a process comprising reacting the salt of formula 2a or the salt of formula 2c, or a salt thereof, with a base. In some embodiments, the reacting of the salt of formula 2a or the salt of formula 2c, or a salt thereof, with a base is conducted in a solvent component comprising water. In some embodiments, the base, present for the reacting of the salt of formula 2a or the salt of formula 2c, or a salt thereof, is a strong base. In some embodiments, the base, present for the reacting of the salt of formula 2a or the salt of formula 2c, or a salt thereof, is a hydroxide. In some embodiments, the base, present for the reacting of the salt of formula 2a or the salt of formula 2c, or a salt thereof, is an alkali metal hydroxide. In some embodiments, the base, present for the reacting of the salt of formula 2a or the salt of formula 2c, or a salt thereof, is sodium hydroxide. In some embodiments, from about 10 to about 15 molar equivalents of the base is utilized relative to the salt of formula 2a or the salt of formula 2c, or a salt thereof. In some embodiments, from about 12 molar equivalents of the base is utilized relative to the salt of formula 2a or the salt of formula 2c, or a salt thereof. In some embodiments, the reacting of the salt of formula 2a or the salt of formula 2c, or a salt thereof, with the base is conducted at a temperature of from about −10° C. to about 60° C. In some embodiments, the temperature is from about 0° C. to room temperature. In some embodiments, the temperature is from about 40° C. to about 60° C. In some embodiments, the temperature is from 0° C. to room temperature and then heated to from about 40° C. to about 60° C.

In some embodiments, the salt of formula 2a, or the salt thereof, or the compound of formula 2b is prepared by a process comprising:

reacting the compound of formula 1a:

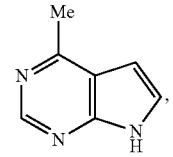

1a or a salt thereof, with a Vilsmeier reagent formed from dimethylformamide.

In some embodiments, the salt of formula 2a, or the salt thereof, or the compound of formula 2b is prepared by a process comprising:

reacting the compound of formula 5a:

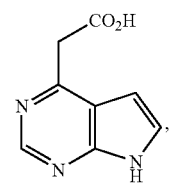

5a or a salt thereof, with a Vilsmeier reagent formed from dimethylformamide.

In some embodiments, the compound of formula 5a is a salt. In some embodiments, the compound of formula 5a is the sodium salt.

In some embodiments, the product of the reacting of the salt of formula 2a, or the salt thereof, (or, alternatively, the compound of formula 5a, or the salt thereof) with the Vilsmeier reagent is a salt of formula 2d:

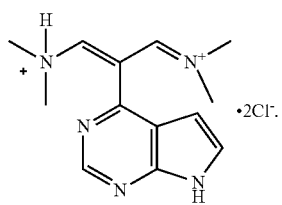

2d

In some embodiments, the salt of formula 2d is crystalline. In some embodiments, the crystalline form of the salt of formula 2d is Form I.

Figure 2:
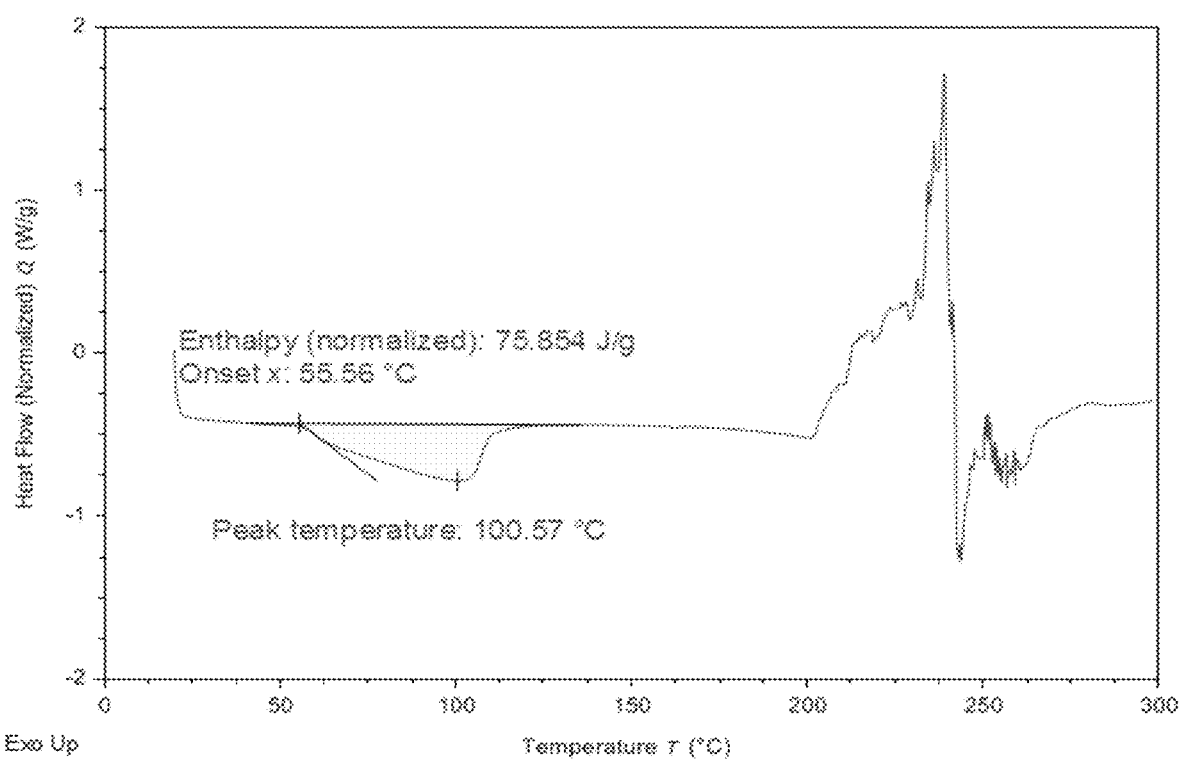
FIG. 2 is a differential scanning calorimetry (DSC) thermogram of Compound 2d Form I.
Figure 3:
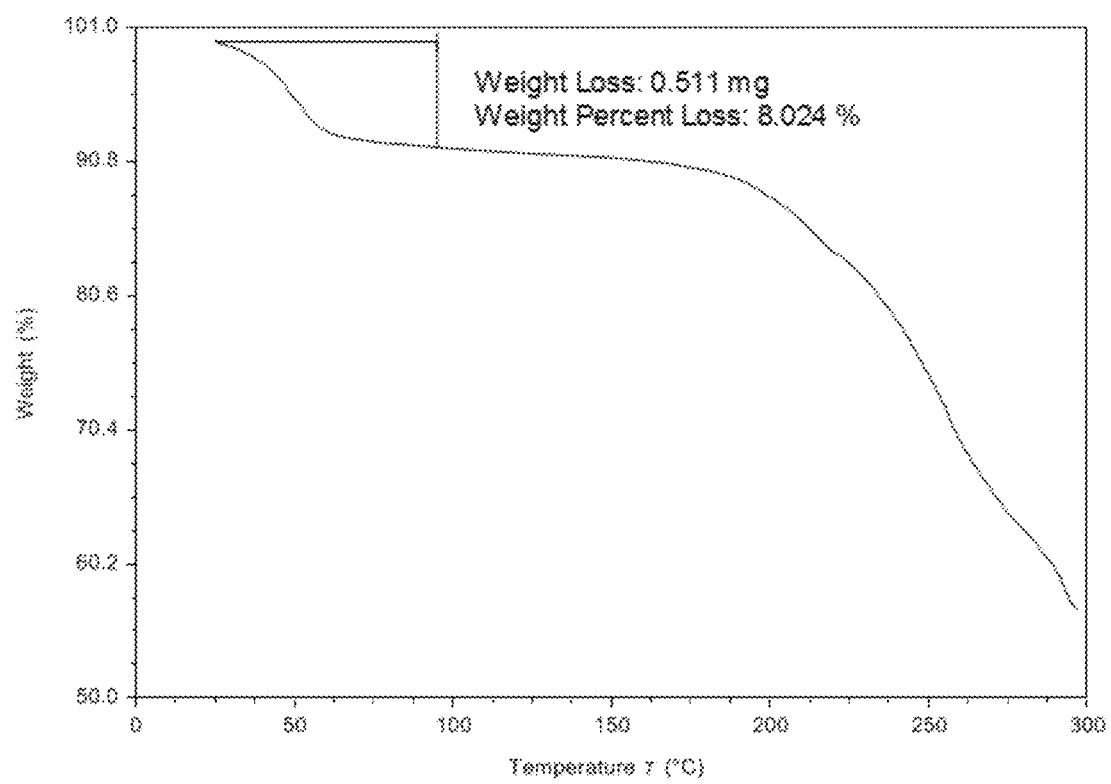
FIG. 3 is a thermogravimetric analysis (TGA) thermogram of Compound 2d Form I.

In some embodiments, Form I has an XRPD pattern substantially as shown in FIG. 1. Form I can have a DSC thermogram substantially as depicted in FIG. 2. In some embodiments, Form I has a TGA thermogram substantially as depicted in FIG. 3.

In some embodiments, Form I has at least one XRPD peak, in terms of 2-theta (±0.2 degrees), selected from 7.4, 12.5, 13.1, 14.1, 14.6, 15.0, 15.9, 17.7, 18.5, 19.0, 20.5, 20.8, 22.2, 23.0, 24.3, 26.3, and 27.9 degrees. In some embodiments, Form I has at least two XRPD peaks, in terms of 2-theta (±0.2 degrees), selected from 7.4, 12.5, 13.1, 14.1, 14.6, 15.0, 15.9, 17.7, 18.5, 19.0, 20.5, 20.8, 22.2, 23.0, 24.3, 26.3, and 27.9 degrees. In some embodiments, Form I has at least three XRPD peaks, in terms of 2-theta (±0.2 degrees), selected from 7.4, 12.5, 13.1, 14.1, 14.6, 15.0, 15.9, 17.7, 18.5, 19.0, 20.5, 20.8, 22.2, 23.0, 24.3, 26.3, and 27.9 degrees. In some embodiments, Form I has at least four XRPD peaks, in terms of 2-theta (±0.2 degrees), selected from 7.4, 12.5, 13.1, 14.1, 14.6, 15.0, 15.9, 17.7, 18.5, 19.0, 20.5, 20.8, 22.2, 23.0, 24.3, 26.3, and 27.9 degrees. In some embodiments, Form I has characteristic XRPD peaks, in terms of 2-theta (±0.2 degrees), at 7.4, 12.5, 13.1, 14.1, 14.6, 15.0, 15.9, 17.7, 18.5, 19.0, 20.5, 20.8, 22.2, 23.0, 24.3, 26.3, and 27.9 degrees.

In some embodiments, Form I has an endothermic peak with an onset temperature (±3° C.) at 56° C. and a maximum at 101° C. in a DSC thermogram.

Figure 4:
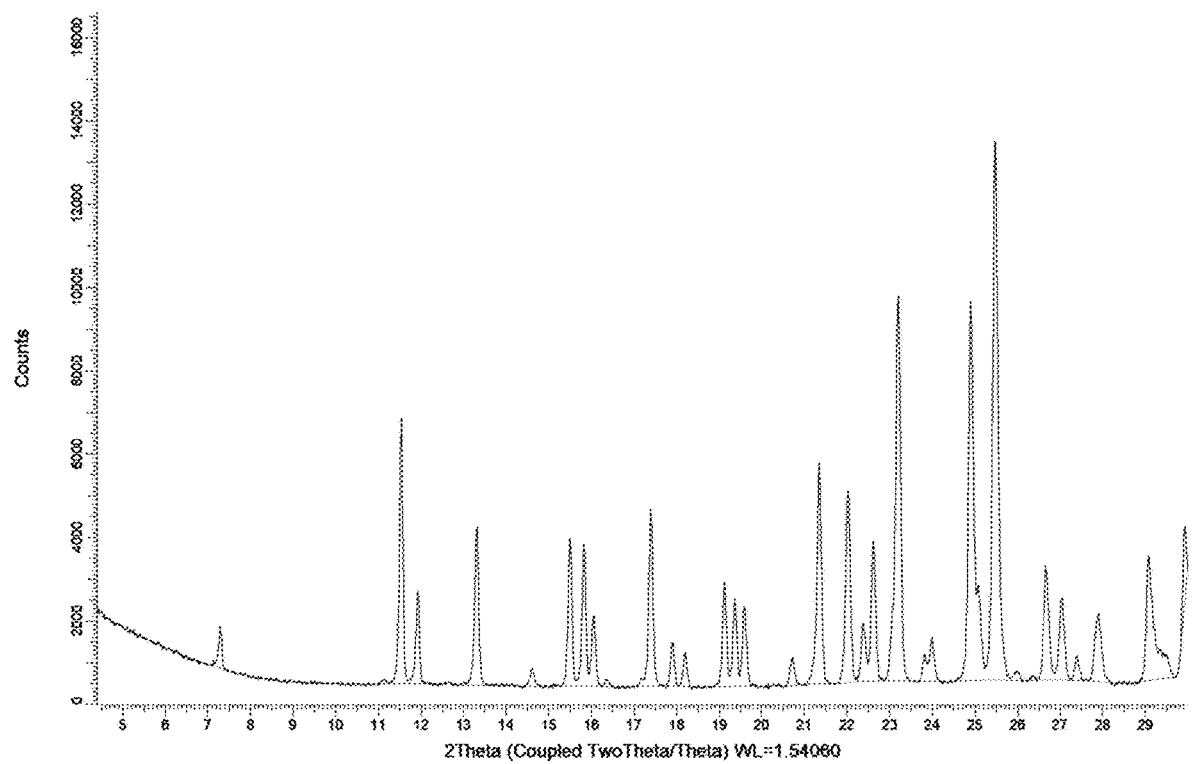
FIG. 4 is an XRPD pattern of Compound 2d Form II.
Figure 5:
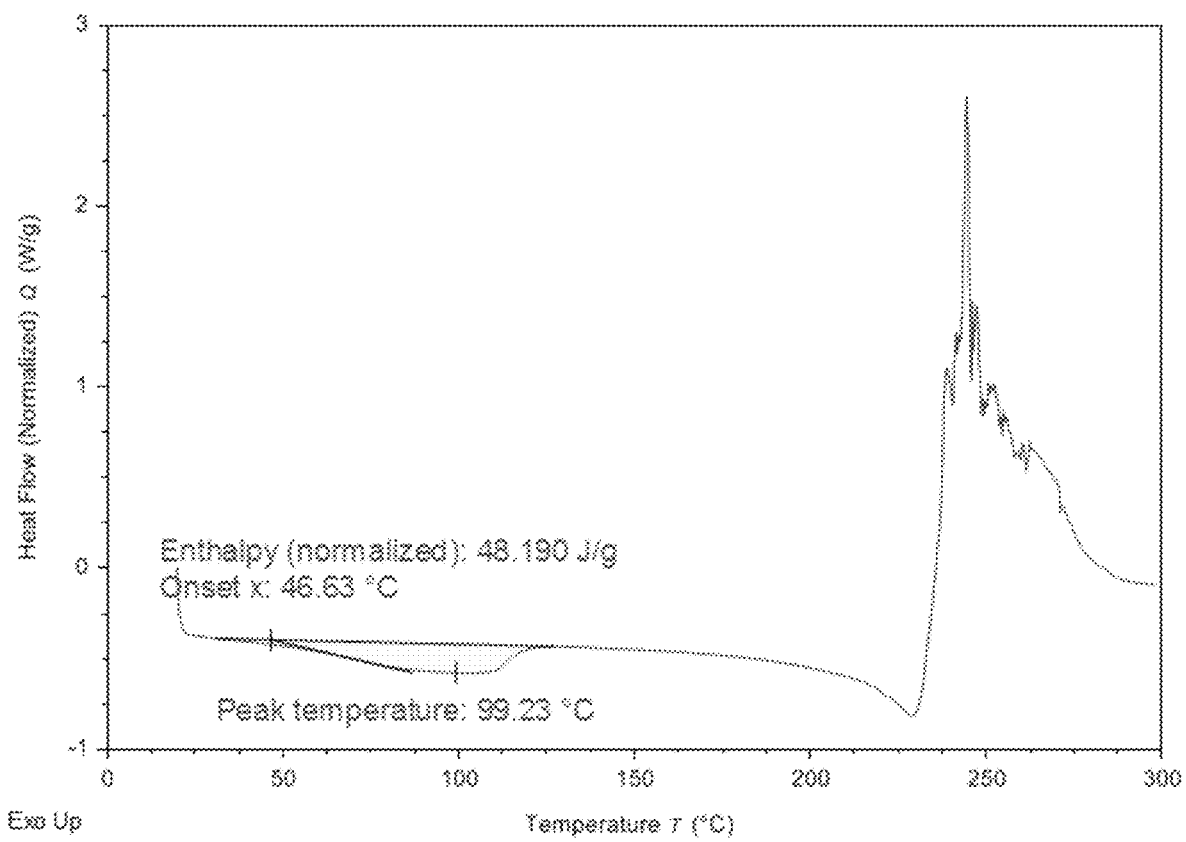
FIG. 5 is a DSC thermogram of Compound 2d Form II.
Figure 6:
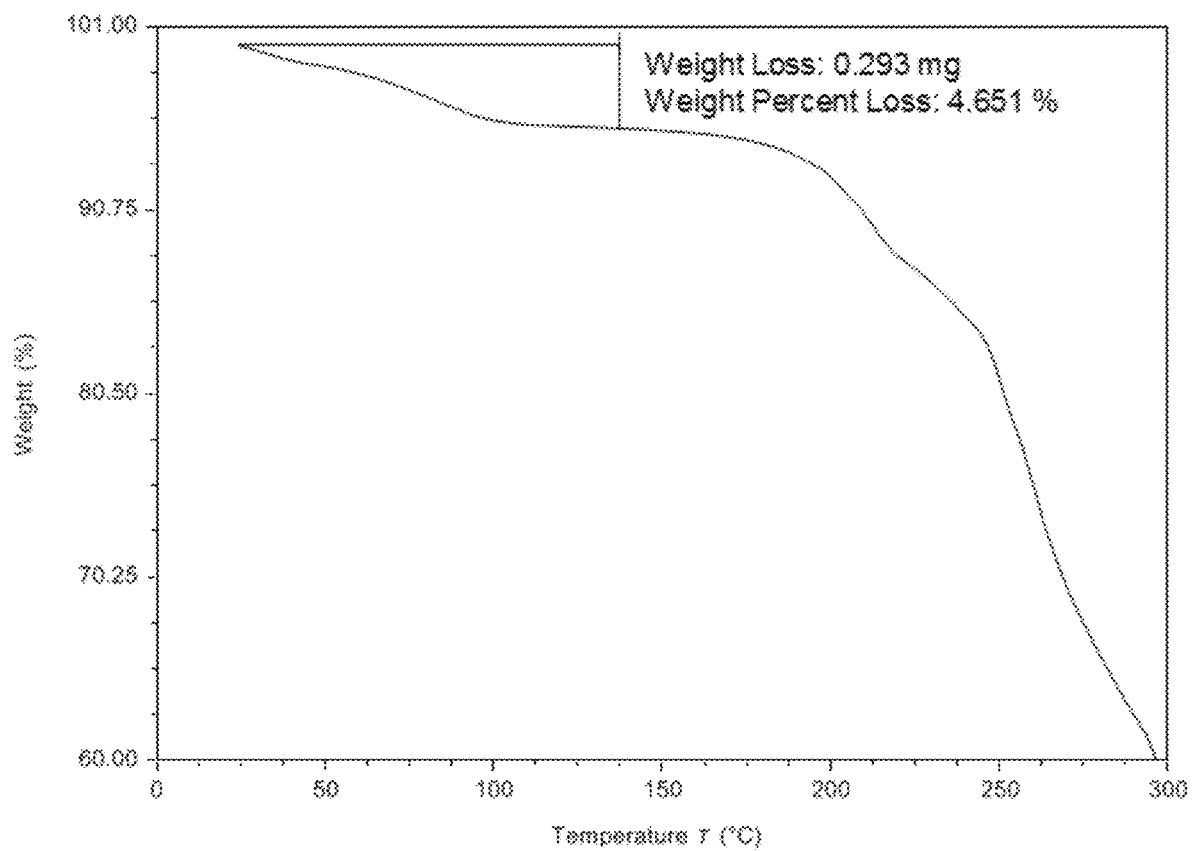
FIG. 6 is a TGA thermogram of Compound 2d Form II.

In some embodiments, the crystalline form of the salt of formula 2d is Form II. In some embodiments, Form II has an XRPD pattern as substantially shown in FIG. 4. In some embodiments, Form II has a DSC thermogram substantially as depicted in FIG. 5. In some embodiments, Form II a TGA thermogram substantially as depicted in FIG. 6.

In some embodiments, Form II has at least one XRPD peak, in terms of 2-theta (±0.2 degrees), selected from 7.3, 11.5, 11.9, 13.3, 15.5, 15.8, 16.1, 17.4, 19.1, 19.4, 19.6, 21.4, 22.0, 22.6, 23.2, 24.9, 25.5, 26.7, and 29.1 degrees. In some embodiments, Form II has at least two XRPD peaks, in terms of 2-theta (±0.2 degrees), selected from 7.3, 11.5, 11.9, 13.3, 15.5, 15.8, 16.1, 17.4, 19.1, 19.4, 19.6, 21.4, 22.0, 22.6, 23.2, 24.9, 25.5, 26.7, and 29.1 degrees. In some embodiments, Form has at least three XRPD peaks, in terms of 2-theta (±0.2 degrees), selected from 7.3, 11.5, 11.9, 13.3, 15.5, 15.8, 16.1, 17.4, 19.1, 19.4, 19.6, 21.4, 22.0, 22.6, 23.2, 24.9, 25.5, 26.7, and 29.1 degrees. In some embodiments, Form II has at least four XRPD peaks, in terms of 2-theta (±0.2 degrees), selected from 7.3, 11.5, 11.9, 13.3, 15.5, 15.8, 16.1, 17.4, 19.1, 19.4, 19.6, 21.4, 22.0, 22.6, 23.2, 24.9, 25.5, 26.7, and 29.1 degrees. In some embodiments, Form II has characteristic XRPD peaks, in terms of 2-theta (±0.2 degrees), at 7.3, 11.5, 11.9, 13.3, 15.5, 15.8, 16.1, 17.4, 19.1, 19.4, 19.6, 21.4, 22.0, 22.6, 23.2, 24.9, 25.5, 26.7, and 29.1 degrees.

In some embodiments, Form II has an endothermic peak with an onset temperature (±3° C.) at 47° C. and a maximum at 99° C. in a DSC thermogram.

In some embodiments, the process of making the salt of formula 2a further comprises reacting the salt of formula 2d with a base to form a salt of formula 2c:

In some embodiments, the product of the reacting of the salt of formula 2a, or the salt thereof, (or, alternatively, the compound of formula 5a, or the salt thereof) with the Vilsmeier reagent is a salt of formula 2c (which is a salt of formula 2a, wherein X— is Cl⁻):

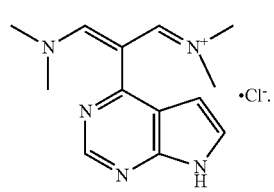

In some embodiments, the process of making the salt of formula 2a further comprises reacting the salt of formula 2c with a salt of formula $M^+X^-$ to form the salt of formula 2a, wherein:

$M^+$ is a counter cation; and $X^-$ is a counter anion other than Cl⁻.

In some embodiments, $M^+$ is an alkali metal counter cation. In some embodiments, $M^+$ is $Li^+$, $Na^+$ or $K^+$. In some embodiments, $M^+$ is $Na^+$. In some embodiments, $X^-$ is selected from $Br^-$, $I^-$, $BF_4^-$, $PF_6^-$, $AsF_6^-$, $SbF_6$, and $ClO_4^-$. In some embodiments, $X^-$ is selected from $BF_4^-$, $PF_6^-$, $AsF_6^-$, $SbF_6^-$, and $ClO_4^-$. In some embodiments, $X^-$ is $BF_4^-$. In some embodiments, $X^-$ is $PF_6^-$. In some embodiments, $X^-$ is $AsF_6^-$. In some embodiments, $X^-$ is $SbF_6^-$. In some embodiments, $X^-$ is $ClO_4^-$.

In some embodiments, the Vilsmeier reagent used in any of the reactions described herein is prepared by a process comprising reacting dimethylformamide with a chlorinating agent. In some embodiments, the chlorinating agent is selected from oxalyl chloride, phosphorus oxychloride, triphosgene, thionyl chloride, sulfuryl chloride, and phosphorus pentachloride. In some embodiments, the chlorinating agent is selected from oxalyl chloride, phosphorus oxychloride, and triphosgene. In some embodiments, the chlorinating agent is oxalyl chloride. In some embodiments, the chlorinating agent is phosphorus oxychloride. In some embodiments, the chlorinating agent is triphosgene.

In some embodiments, from about 1 to about 5 molar equivalents of the chlorinating agent, present for the reacting with dimethylformamide, are utilized relative to the compound of formula 1a or 5a, or the salt thereof. In some embodiments, from about 1 to about 4 molar equivalents of the chlorinating agent, present for the reacting with dimethylformamide, are utilized relative to the compound of formula 1a or 5a, or the salt thereof. In some embodiments, from about 1 to about 3 molar equivalents of the chlorinating agent, present for the reacting with dimethylformamide, are utilized relative to the compound of formula 1a or 5a, or the salt thereof. In some embodiments, about 1 molar equivalent of the chlorinating agent, present for the reacting with dimethylformamide, is utilized relative to the compound of formula 1a or 5a, or the salt thereof. In some embodiments, about 2 molar equivalents of the chlorinating agent, present for the reacting with dimethylformamide, are utilized relative to the compound of formula 1a or 5a, or the salt thereof. In some embodiments, about 3 molar equivalents of the chlorinating agent, present for the reacting with dimethylformamide, are utilized relative to the compound of formula 1a or 5a, or the salt thereof. In some embodiments, about 4 molar equivalents of the chlorinating agent, present for the reacting with dimethylformamide, are utilized relative to the compound of formula 1a or 5a, or the salt thereof. In some embodiments, about 5 molar equivalents of the chlorinating agent, present for the reacting with dimethylformamide, are utilized relative to the compound of formula 1a or 5a, or the salt thereof.

In some embodiments, from about 10 to about 25 molar equivalents of dimethylformamide, present for the reacting with a chlorinating agent, are utilized relative to the compound of formula 1a or 5a, or the salt thereof. In some embodiments, from about 10 to about 20 molar equivalents of dimethylformamide, present for the reacting with a chlorinating agent, are utilized relative to the compound of formula 1a or 5a, or the salt thereof. In some embodiments, from about 10 to about 15 molar equivalents of dimethylformamide, present for the reacting with a chlorinating agent, are utilized relative to the compound of formula 1a or 5a, or the salt thereof. In some embodiments, from about 11 to about 14 molar equivalents of dimethylformamide, present for the reacting with a chlorinating agent, are utilized relative to the compound of formula 1a or 5a, or the salt thereof. In some embodiments, from about 11 to about 13 molar equivalents of dimethylformamide, present for the reacting with a chlorinating agent, are utilized relative to the compound of formula 1a, or the salt thereof.

In some embodiments, the preparation of the Vilsmeier reagent is carried out in a solvent component. In some embodiments, the solvent component, present for the preparation of the Vilsmeier reagent, comprises an organic solvent. In some embodiments, the solvent component, present for the preparation of the Vilsmeier reagent, comprises a polar aprotic solvent. In some embodiments, the solvent component, present for the preparation of the Vilsmeier reagent, comprises acetonitrile, dimethyformamide, or a combination thereof.

In some embodiments, the Vilsmeier reagent is prepared at a temperature between from about −10° C. to about 60° C. In some embodiments, the Vilsmeier reagent is prepared at a temperature between from about −10° C. to about 30° C. In some embodiments, the Vilsmeier reagent is prepared at a temperature between from about −10° C. to about room temperature. In some embodiments, the temperature is about 0° C. to about room temperature. In some embodiments, the Vilsmeier reagent is prepared at a temperature between from about room temperature to about 60° C. In some embodiments, the Vilsmeier reagent is prepared at a temperature between from about 30° C. to about 70° C., about 40° C. to about 70° C., about 30° C. to about 60° C., or about 40° C. to about 60° C. In some embodiments, the Vilsmeier reagent is prepared at a temperature between from about 75° C. to about 80° C., 80° C. to 90° C., or 85° C. to 90° C.

In some embodiments, the reacting of the compound of formula 1a or 5a, or the salt thereof, with the Vilsmeier reagent is carried out at a temperature of from about 40° C. to about 100° C. In some embodiments, the reacting of the compound of formula 1a or 5a, or the salt thereof, with the Vilsmeier reagent is carried out at a temperature of from about 70° C. to about 100° C. In some embodiments, the reacting of the compound of formula 1a or 5a, or the salt thereof, with the Vilsmeier reagent is carried out at a temperature of from about 40° C. to about 60° C.

In some embodiments, the compound of formula 1a, or the salt thereof, is the hydrochloride salt.

In some embodiments, the compound of formula 1a, or the salt thereof, is prepared by a process comprising:
deprotecting a compound of formula 1aP:

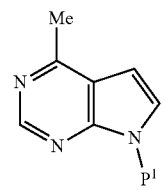

1aP wherein P¹ is an amino protecting group.

In some embodiments, P¹ is selected from (R¹)₃Si, wherein R¹ is C₁₋₆ alkyl. In some embodiments, R¹ is methyl, ethyl, propyl, isopropyl, butyl or t-butyl. In some embodiments, P¹ is t-butyldimethylsilyl. In some embodiments, P¹ is trimethylsilyl. In some embodiments, the deprotecting is carried out by reacting the compound of formula 1aP with a base. In some embodiments, the base, present for the deprotecting a compound of formula 1 aP, is a hydroxide base. In some embodiments, the base, present for the deprotecting a compound of formula 1 aP, is ammonium hydroxide. In some embodiments, the deprotecting is carried out in a solvent component. In some embodiments, the solvent component, present for the deprotecting a compound of formula 1 aP, comprises a polar protic solvent. In some embodiments, the solvent component, present for the deprotecting a compound of formula 1aP, comprises an alcohol. In some embodiments, the solvent component, present for the deprotecting a compound of formula 1aP, comprises formula C₁₋₆ alkyl-OH. In some embodiments, the solvent component, present for the deprotecting a compound of formula 1 aP, comprises methanol.

In some embodiments, the compound of formula 1aP is prepared by a process comprising:
reacting a compound of formula 2P:

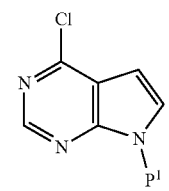

2P with MeMgBr in the presence of a Grignard catalyst,
wherein P¹ is an amino protecting group.

In some embodiments, the Grignard catalyst is an iron catalyst. In some embodiments, the iron catalyst is iron(III) acetylacetonate. In some embodiments, from about 1 to about 2 molar equivalents of MeMgBr are utilized relative to the compound of formula 2P. In some embodiments, from about 1% to about 10% molar equivalents of the Grignard catalyst are utilized relative to the compound of formula 2P. In some embodiments, the reacting of the compound formula 2P with MeMgBr is carried out in a solvent component. In some embodiments, the solvent component, present for the reacting of the compound formula 2P with MeMgBr, comprises a di-$C_{1-6}$ alkyl ether or a 4-10 membered heterocycloalkyl ether. In some embodiments, the solvent component, present for the reacting of the compound formula 2P with MeMgBr, comprises a tetrahydrofuran. In some embodiments, the reacting of the compound formula 2P with MeMgBr is carried out at a temperature of from about −10° C. to about 30° C.

In some embodiments, the compound of formula 2P is prepared by a process comprising:
protecting a compound of formula 12a:

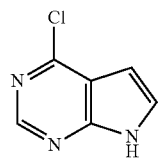

12a to form the compound of formula 2P.

In some embodiments, the protecting comprises reacting the compound of formula 12a with an alkali metal hydride and $P^1$—Y, wherein Y is halo. In some embodiments, $P^1$—Y is $(R^1)_3Si$—Y, wherein Y is halo and $R^1$ is $C_{1-6}$ alkyl. In some embodiments, $P^1$ is $(R^1)_3Si$, wherein $R^1$ is $C_{1-6}$ alkyl. In some embodiments, $R^1$ is methyl, ethyl, propyl, isopropyl, butyl or t-butyl. In some embodiments, $P^1$ is t-butyldimethylsilyl. In some embodiments, the alkali metal hydride is sodium hydride. In some embodiments, from about 1 to about 2 molar equivalents of the alkali metal hydride is utilized relative to the compound of formula 12a. In some embodiments, from about 1 to about 2 molar equivalents of $P^1$—Y is utilized relative to the compound of formula 12a. In some embodiments, the reacting of the compound of formula 12a with the alkali metal hydride and $P^1$—Y is carried out at a temperature of about −10° C. to about 20° C. In some embodiments, the reacting of the compound of formula 12a with the alkali metal hydride and $P^1$—Y is carried out in a solvent component, wherein the solvent component comprises an organic solvent. In some embodiments, the solvent component, present for the reacting of the compound of formula 12a with the alkali metal hydride and $P^1$—Y, comprises a di-$C_{1-6}$ alkyl ether or a 4-10 membered heterocycloalkyl ether. In some embodiments, the solvent component, present for the reacting of the compound of formula 12a with the alkali metal hydride and $P^1$—Y, comprises a tetrahydrofuran.

In some embodiments, the compound of formula 1a, or the salt thereof, is prepared by a process comprising:
reducing a compound of formula 23P:

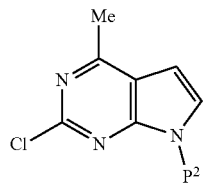

23P to form the compound of formula 1a, or the salt thereof;
wherein $P^2$ is an amino protecting group. Note that the HCl generated from the reduction results in removal of the protecting group $P^2$.

In some embodiments, the reducing of the compound of formula 23P is accomplished by a process comprising reacting the compound of formula 23P with hydrogen gas in the presence of a catalyst. For example, the catalyst, present for the reacting of the compound of formula 23P with hydrogen gas, is $Pd^0$ on carbon. In some embodiments, the amount of the catalyst relative to the compound of formula 23P is about 5% to about 15% by weight. In some embodiments, the reacting of the compound of formula 23P with hydrogen and the catalyst is carried out at a temperature of about 40° C. to about 70° C. In some embodiments, the reacting of the compound of formula 23P with hydrogen and the catalyst is carried out at a temperature of about 50° C. to about 60° C. In some embodiments, the reacting of the compound of formula 23P with hydrogen and the catalyst is carried out at a temperature of about 50° C. to about 55° C. In some embodiments, the reacting of the compound of formula 23P with hydrogen and the catalyst is carried out in a solvent component. In some embodiments, the solvent component, present for the reacting of the compound of formula 23P with hydrogen and the catalyst, comprises a polar protic solvent. In some embodiments, the solvent component, present for the reacting of the compound of formula 23P with hydrogen and the catalyst, comprises an alcohol. In some embodiments, the solvent component, present for the reacting of the compound of formula 23P with hydrogen and the catalyst, comprises formula $C_{1-6}$ alkyl-OH. In some embodiments, the solvent component, present for the reacting of the compound of formula 23P with hydrogen and the catalyst, comprises methanol.

In some embodiments, the compound of formula 1a, or the salt thereof, is the hydrochloric acid salt.

In some embodiments, the compound of formula 23P is prepared by a process comprising:
reacting a compound of formula 22P:

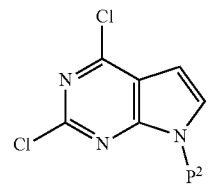

22P with MeMgCl in the presence of a Grignard catalyst,
wherein $P^2$ is an amino protecting group.

In some embodiments, the Grignard catalyst is an iron catalyst. In some embodiments, the iron catalyst is iron(III) acetylacetonate. In some embodiments, from about 1 to about 2 molar equivalents of MeMgCl is utilized relative to the compound of formula 22P. In some embodiments, from about 1% to about 10% molar equivalents of the Grignard catalyst are utilized relative to the compound of formula 22P. In some embodiments, the reacting of the compound formula 22P with MeMgCl is carried out in a solvent component. In some embodiments, the solvent component, present for the reacting of the compound formula 22P with MeMgCl, comprises a di-$C_{1-6}$ alkyl ether or a 4-10 membered heterocycloalkyl ether. In some embodiments, the solvent component, present for the reacting of the compound formula 22P with MeMgCl, comprises a tetrahydrofuran. In some embodiments, the reacting of the compound formula 22P with MeMgCl is carried out at a temperature of from about −10° C. to about 30° C.

In some embodiments, the compound of formula 22P is prepared by a process comprising:

protecting a compound of formula 22a:

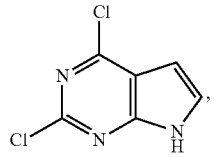

22a to form the compound of formula 22P.

In some embodiments, the protecting comprise reacting the compound of formula 22a with an alkali metal hydride and P²—Y, wherein Y is halo. In some embodiments, P² is (R¹)₃Si, wherein R¹ is $C_{1-6}$ alkyl. In some embodiments, R¹ is methyl, ethyl, propyl, isopropyl, butyl or t-butyl. In some embodiments, P² is t-butyldimethylsilyl. In some embodiments, the alkali metal hydride is sodium hydride. In some embodiments, from about 1 to about 2 molar equivalents of the alkali metal hydride is utilized relative to the compound of formula 22a. In some embodiments, from about 1 to about 2 molar equivalents of P²—Y are utilized relative to the compound of formula 22a. In some embodiments, the reacting of the compound of formula 22a with the alkali metal hydride and P²—Y is carried out at a temperature of about −10° C. to about 20° C. In some embodiments, the reacting of the compound of formula 22a with the alkali metal hydride and P²—Y is carried out in a solvent component, wherein the solvent component comprises an organic solvent. In some embodiments, the solvent component, present for the reacting of the compound of formula 22a with the alkali metal hydride and P²—Y, comprises a di-$C_{1-6}$ alkyl ether or a 4-10 membered heterocycloalkyl ether. In some embodiments, the solvent component, present for the reacting of the compound of formula 22a with the alkali metal hydride and P²—Y, comprises a tetrahydrofuran.

In some embodiments, the compound of formula 1a, or the salt thereof, is prepared by a process comprising:

reacting a compound of formula 18a:

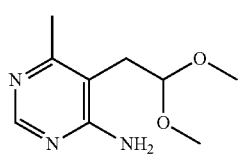

18a with an acid to form the compound of formula 1a, or the salt thereof.

In some embodiments, the acid, present for the reacting of the compound of formula 18a, is a strong acid. In some embodiments, the acid, present for the reacting of the compound of formula 18a, is hydrochloric acid. In some embodiments, the reacting of the compound of formula 18a with the acid is carried out in a solvent component, wherein the solvent component comprises a polar protic solvent. In some embodiments, the solvent component, present for the reacting of the compound of formula 18a with the acid, comprises an alcohol. In some embodiments, the solvent component, present for the reacting of the compound of formula 18a with the acid, comprises formula $C_{1-6}$ alkyl-OH. In some embodiments, the solvent component, present for the reacting of the compound of formula 18a with the acid, comprises isopropyl alcohol.

In some embodiments, the compound of formula 18a is prepared by a process comprising:

reacting a compound of formula 17a:

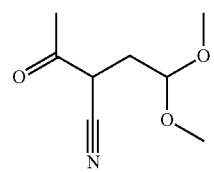

17a with formamidine acetate and triethyl orthoformate to form the compound of formula 18a, or the salt thereof.

In some embodiments, from about 10 to about 15 molar equivalents of formamidine acetate is utilized relative to the compound of formula 17a. In some embodiments, about 10, about 11, about 12, about 13, about 14, or about 15 molar equivalents of formamidine acetate is utilized relative to the compound of formula 17a. In some embodiments, about 12 molar equivalents of formamidine acetate is utilized relative to the compound of formula 17a. In some embodiments, from about 6 to about 10 molar equivalents of triethyl orthoformate is utilized relative to the compound of formula 17a. In some embodiments, about 6, about 7, about 8, about 9, or about 10 molar equivalents of triethyl orthoformate is utilized relative to the compound of formula 17a. In some embodiments, about 8 molar equivalents of triethyl orthoformate is utilized relative to the compound of formula 17a. In some embodiments, the reacting of the compound of formula 17a with formamidine acetate and triethyl orthoformate is carried out at a temperature of about 100° C. to about 150° C. In some embodiments, the temperature is about 110° C. to about 120° C. In some embodiments, the reacting of the compound of formula 17a with formamidine acetate and triethyl orthoformate is carried out in a solvent component, wherein the solvent component comprises a polar protic solvent. In some embodiments, the polar protic solvent comprises an alcohol. In some embodiments, the polar protic solvent comprises formula $C_{1-6}$ alkyl-OH. In some embodiments, the polar protic solvent comprises 1-butanol.

In some embodiments, the compound of formula 17a is prepared by a process comprising:

reacting a compound of formula 20a:

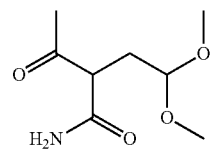

20a with a compound of formula 21a:

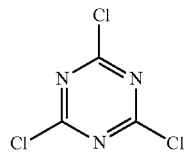

21a to form the compound of formula 17a.

In some embodiments, from about 0.4 to about 1 molar equivalents of the compound of formula 21a are utilized relative to the compound of formula 20a. In some embodiments, the reacting of the compound of formula 20a with the compound of formula 21a is carried out at room temperature. In some embodiments, the reacting of the compound of formula 20a with the compound of formula 21a is carried out in a solvent component, wherein the solvent component comprises a polar aprotic solvent. In some embodiments, the solvent component, present for the reacting of the compound of formula 20a with the compound of formula 21a, comprises dimethylformamide.

In some embodiments, the compound of formula 20a is prepared by a process comprising:
reacting a compound of formula 19a:

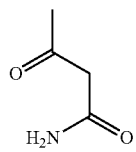

19a with bromo-1,1-dimethoxyethane and a base to form the compound of formula 20a.

In some embodiments, the base, present for the reacting of the compound of formula 19a with the bromo-1,1-dimethoxyethane, is an alkali metal carbonate. In some embodiments, the base, present for the reacting of the compound of formula 19a with the bromo-1,1-dimethoxyethane, is cesium carbonate. In some embodiments, from about 1 to about 2 molar equivalents of the base is utilized relative to the compound of formula 19a. In some embodiments, from about 1 to about 2 molar equivalents of bromo-1,1-dimethoxyethane is utilized relative to the compound of formula 19a. In some embodiments, the reacting of the compound of formula 19a with bromo-1,1-dimethoxyethane is carried out at a temperature of about 70° C. to about 100° C. In some embodiments, the reacting of the compound of formula 19a with bromo-1,1-dimethoxyethane is carried out in a solvent component, wherein the solvent component comprises a polar aprotic solvent. In some embodiments, the solvent component, present for the reacting of the compound of formula 19a with the bromo-1,1-dimethoxyethane, comprises dimethylformamide.

In some embodiments, the compound of formula 17a is prepared by a process comprising:
reacting a compound of formula 16a:

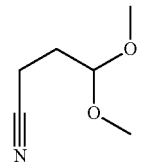

16a with ethyl acetate and a base to form the compound of formula 17a.

In some embodiments, the base, present for the reacting of the compound of formula 16a with ethyl acetate, is an alkali metal alkoxide. In some embodiments, the base, present for the reacting of the compound of formula 16a with the ethyl acetate, is potassium tert-butoxide. In some embodiments, from about 1 to about 3 molar equivalents of the base is utilized relative to the compound of formula 16a. In some embodiments, from about 1 to about 2 molar equivalents of ethyl acetate is utilized relative to the compound of formula 16a. In some embodiments, about 2 molar equivalents of the base is utilized relative to the compound of formula 16a. In some embodiments, the reacting of the compound of formula 16a with ethyl acetate and a base is carried out at room temperature. In some embodiments, the reacting of the compound of formula 16a with ethyl acetate and a base is carried out in a solvent component, wherein the solvent component comprises an organic solvent. In some embodiments, the solvent component, present for the reacting of the compound of formula 16a with ethyl acetate, comprises a di-$C_{1-6}$ alkyl ether or a 4-10 membered heterocycloalkyl ether. In some embodiments, the solvent component, present for the reacting of the compound of formula 16a with the ethyl acetate, comprises a tetrahydrofuran.

In some embodiments, the compound of formula 5a, or the salt thereof, is prepared by a process comprising:
hydrolyzing a compound of formula 27a:

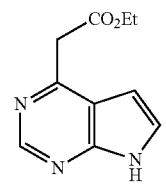

27a in water in the presence of a base.

In some embodiments, the base, present for the hydrolyzing of the compound of formula 27a, is an alkali metal hydroxide. In some embodiments, the base, present for the hydrolyzing of the compound of formula 27a, is sodium hydroxide. In some embodiments, from about 1 to about 2 molar equivalents of the base is utilized relative to the compound of formula 27a. In some embodiments, about 1.5 molar equivalents of the base is utilized relative to the compound of formula 27a. In some embodiments, the hydrolyzing of the compound of formula 27a is carried out at room temperature. In some embodiments, the hydrolyzing of the compound of formula 27a is carried out in a solvent component, wherein the solvent component comprises an organic solvent. In some embodiments, the solvent component, present for the hydrolyzing of the compound of formula 27a, comprises tetrahydrofuran, acetone, or a combination thereof.

In some embodiments, the compound of formula 5a, or the salt thereof, is the sodium salt of the compound of formula 5a. In some embodiments, the compound of formula 5a, or the salt thereof, is the compound of formula 5a.

In some embodiments, the product of the hydrolysis of the compound of formula 27a is the sodium salt of the compound of formula 5a. In some embodiments, the process further comprises reacting the sodium salt of the compound of formula 5a with a strong acid to form the compound of formula 5a.

In some embodiments, the compound of formula 5a is prepared by a process comprising reacting the sodium salt of the compound of formula 5a with a strong acid. In some embodiments, the strong acid, present for reacting the sodium salt of the compound of formula 5a, is hydrochloric acid. In some embodiments, the reacting of the sodium salt of compound of formula 5a with a strong acid and the hydrolyzing of the compound of formula 27a is carried out in a single pot.

In some embodiments, the compound of formula 27a is prepared by a process comprising:
reacting a compound of formula 26P:

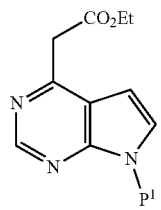

with a strong acid, wherein $P^1$ is an amino protecting group.

In some embodiments, $P^1$ is p-toluenesulfonyl. In some embodiments, the strong acid, present for the reacting of the compound of formula 26P, is hydrochloric acid. In some embodiments, the reacting of the compound of formula 26P with a strong acid is carried out at room temperature. In some embodiments, the reacting of the compound of formula 26P with a strong acid is carried out in a solvent component. In some embodiments, the solvent component, present for the reacting of the compound of formula 26P with the strong acid, comprises formula $C_{1-6}$ alkyl-OH. In some embodiments, the solvent component, present for the reacting of the compound of formula 26P with the strong acid, comprises ethanol.

In some embodiments, the compound of formula 26P is prepared by a process comprising:
reacting a compound of formula 25P:

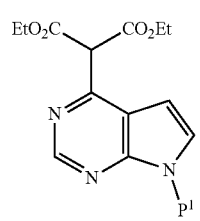

with an alkali metal alkoxide to form the compound of formula 26P, wherein $P^1$ is an amino protecting group.

In some embodiments, about 0.1 molar equivalents of the alkali metal alkoxide is utilized relative to the compound of formula 25P. In some embodiments, the reacting of the compound of formula 25P with the alkali metal alkoxide is carried out at room temperature. In some embodiments, the alkali metal alkoxide is sodium ethoxide. In some embodiments, the reacting of the compound of formula 25P with the alkali metal alkoxide is carried out in a solvent component, wherein the solvent component comprises a polar protic solvent. In some embodiments, the solvent component, present for the reacting of the compound of formula 25P with the alkali metal alkoxide, comprises an alcohol. In some embodiments, the solvent component, present for the reacting of the compound of formula 25P with the alkali metal alkoxide, comprises formula $C_{1-6}$ alkyl-OH. In some embodiments, the solvent component, present for the reacting of the compound of formula 25P with the alkali metal alkoxide, comprises ethanol.

In some embodiments, the compound of formula 27a is prepared by a process comprising:
reacting a compound of formula 25P:

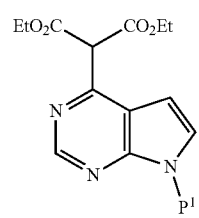

with an alkali metal alkoxide to form the compound of formula 27a.

In some embodiments, from about 1 to about 2 molar equivalents of the alkali metal alkoxide are utilized relative to the compound of formula 25P. In some embodiments, about 1 molar equivalent of the alkali metal alkoxide is utilized relative to the compound of formula 25P. In some embodiments, the reacting of the compound of formula 25P with the alkali metal alkoxide is carried out at a temperature of about 50° C. to about 80° C. In some embodiments, the reacting of the compound of formula 25P with the alkali metal alkoxide is carried out in a solvent component, wherein the solvent component, present for the reacting of the compound of formula 25P with the alkali metal alkoxide, comprises formula $C_{1-6}$ alkyl-OH. In some embodiments, the solvent component, present for the reacting of the compound of formula 25P with the alkali metal alkoxide, comprises ethanol.

In some embodiments, the compound of formula 25P is prepared by a process comprising:
reacting a compound of formula 2P:

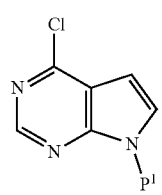

with diethyl malonate and a base, wherein P¹ is an amino protecting group.

In some embodiments, the base, present for the reacting of the compound of formula 2P with the diethyl malonate, is an alkali metal carbonate. In some embodiments, the base, present for the reacting of the compound of formula 2P with the diethyl malonate, is cesium carbonate. In some embodiments, the reacting of the compound of formula 2P with a base is carried out at a temperature of about 40° C. to about 70° C. In some embodiments, the reacting of the compound of formula 2P with a base is carried out in a solvent component, wherein the solvent component comprises a polar aprotic solvent. In some embodiments, the solvent component, present for the reacting of the compound of formula 2P with the diethyl malonate, comprises dimethylformamide.

In some embodiments, the compound of formula 2P is prepared by a process comprising protecting a compound of formula 12a to form the compound of formula 2P. In some embodiments, the protecting comprises reacting the compound of formula 12a with a base and P¹—Y, wherein Y is halo. In some embodiments, P¹ is p-toluenesulfonyl. In some embodiments, the base, present for the reacting of the compound of formula 12a and P¹—Y, is an alkali metal hydroxide. In some embodiments, the base, present for the reacting of the compound of formula 12a and P¹—Y, is sodium hydroxide. In some embodiments, the protecting the compound of formula 12a is carried out in a solvent component, wherein the solvent component comprises a polar aprotic solvent. In some embodiments, the solvent component, present for the reacting of the compound of formula 12a and P¹—Y, comprises acetone.

In some embodiments, the compound of formula 12a is prepared by a process comprising:

reacting a compound of formula 11a:

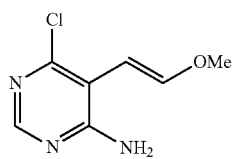

11a or a salt thereof, with a strong acid.

In some embodiments, the strong acid, present for the reacting of the compound of formula 11a, or the salt thereof, is hydrochloric acid. In some embodiments, the reacting of the compound of formula 11a, or the salt thereof, with a strong acid is carried out in a solvent component, wherein the solvent component comprises a polar aprotic solvent. In some embodiments, the solvent component, present for the reacting of the compound of formula 11a, or the salt thereof, with a strong acid, comprises a di-$C_{1-6}$ alkyl ether or a 4-10 membered heterocycloalkyl ether. In some embodiments, the solvent component, present for the reacting of the compound of formula 11a, or the salt thereof, comprises tetrahydrofuran. In some embodiments, the reacting of the compound of formula 11a, or the salt thereof, with a strong acid is carried out at the refluxing temperature of tetrahydrofuran.

In some embodiments, the compound of formula 11a is prepared by a process comprising:

reacting a compound of formula 10a:

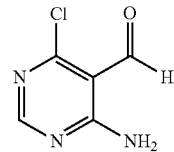

10a or a salt thereof, with (methoxymethyl)triphenylphosphonium chloride and a base.

In some embodiments, the base, present for reacting of the compound of formula 11a, or the salt thereof, with the (methoxymethyl)triphenylphosphonium chloride, is an alkali metal alkoxide. In some embodiments, the base, present for reacting of the compound of formula 11a, or the salt thereof, with the (methoxymethyl)triphenylphosphonium chloride, is potassium tert-butoxide. In some embodiments, the reacting of the compound of formula 11a, or the salt thereof, with (methoxymethyl)triphenylphosphonium chloride and a base is carried out at a temperature of about 10° C. to about 30° C. In some embodiments, the reacting of the compound of formula 11a, or the salt thereof, with (methoxymethyl)triphenylphosphonium chloride and a base is carried out in a solvent component, wherein the solvent component comprises a polar aprotic solvent. In some embodiments, the solvent component, present for reacting of the compound of formula 11a, or the salt thereof, with the (methoxymethyl)triphenylphosphonium chloride, comprises a di-$C_{1-6}$ alkyl ether or a 4-10 membered heterocycloalkyl ether. In some embodiments, the solvent component, present for reacting of the compound of formula 11a, or the salt thereof, with the (methoxymethyl)triphenylphosphonium chloride, comprises tetrahydrofuran.

In some embodiments, the compound of formula 10a, or the salt thereof, is prepared by a process comprising:

reacting a compound of formula 9a:

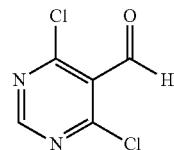

9a with ammonia.

In some embodiments, the reacting of the compound of formula 9a with ammonia is carried out at a temperature of about 40° C. to about 70° C. In some embodiments, the reacting of the compound of formula 9a with ammonia is carried out in a solvent component, wherein the solvent component comprises organic solvent. In some embodiments, in some embodiments, the solvent component, present for the reacting of the compound of formula 9a with ammonia, comprises toluene.

In some embodiments, the compound of formula 9a is prepared by a process comprising:
reacting a compound of formula 8a:

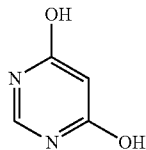

with a Vilsmeier reagent formed from dimethylformamide.

In some embodiments, the Vilsmeier reagent, present for the reacting with the compound of formula 8a, is prepared by a process comprising reacting dimethylformamide with a chlorinating agent. In some embodiments, the chlorinating agent, used to prepare the Vilsmeier reagent for reacting with the compound of formula 8a, is selected from oxalyl chloride, phosphorus oxychloride, triphosgene, thionyl chloride, sulfuryl chloride, and phosphorus pentachloride. In some embodiments, the chlorinating agent, used to prepare the Vilsmeier reagent for reacting with the compound of formula 8a, to form the compound of formula 8a, is phosphorus oxychloride. In some embodiments, about 4 to about 6 molar equivalents (e.g., 5 molar equivalents) of the chlorinating agent is utilized relative to a compound of formula 8a. In some embodiments, about 1 to about 3 molar equivalents (e.g., 2 molar equivalents) of the dimethylformamide is utilized relative to a compound of formula 8a. In some embodiments, the reacting dimethylformamide with a chlorinating agent is prepared at a temperature from about −10° C. to about 20° C. (e.g., about 0° C. to about 10° C.). In some embodiments, the reacting of a compound of formula 8a with a Vilsmeier reagent is carried out at a temperature from about 80° C. to about 130° C. (e.g., about 90° C. to about 120° C., or about 95° C. to about 115° C.).

In some embodiments, the compound of formula 12a is prepared by a process comprising:
reacting a compound of formula 15a:

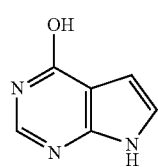

with a chlorinating agent.

In some embodiments, the chlorinating agent, present for the reacting with the compound of formula 15a, is selected from oxalyl chloride, phosphorus oxychloride, triphosgene, thionyl chloride, sulfuryl chloride, and phosphorus pentachloride. In some embodiments, the chlorinating agent, present for the reacting with the compound of formula 15a, is phosphorus oxychloride. In some embodiments, the reacting of the compound of formula 15a with a chlorinating agent is carried out at a temperature of about 50° C. to about 100° C. In some embodiments, the reacting of the compound of formula 15a with ammonia is carried out in a solvent component, wherein the solvent component comprises an organic solvent. In some embodiments, the solvent component, present for the reacting with the compound of formula 15a, comprises toluene.

In some embodiments, the compound of formula 15a is prepared by a process comprising:
(i) reacting a compound of formula 14a:

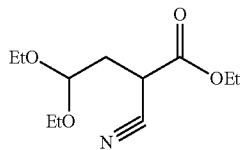

with formamidine acetate and an alkali metal alkoxide to generate a compound of formula 14aa:

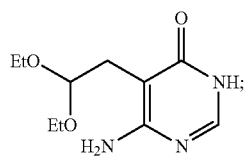

and
(ii) reacting the compound of formula 14aa with a strong acid.

In some embodiments, the alkali metal alkoxide, present for reacting with a compound of formula 14a, is sodium ethoxide. In some embodiments, the reacting of the compound of formula 14a with formamidine acetate and an alkali metal alkoxide is carried out at a temperature of about 50° C. to about 100° C. In some embodiments, the reacting of the compound of formula 14a with formamidine acetate and an alkali metal alkoxide is carried out in a solvent component, wherein the solvent component comprises a polar protic solvent. In some embodiments, the solvent component, present for the reacting of the compound of formula 14a with formamidine acetate and an alkali metal hydroxide, comprises an alcohol. In some embodiments, the solvent component, present for the reacting of the compound of formula 14a with formamidine acetate and an alkali metal hydroxide, comprises formula $C_{1-6}$ alkyl-OH.

In some embodiments, the solvent component, present for reacting with a compound of formula 14a, comprises ethanol.

In some embodiments, the strong acid, present for the reacting of the compound of formula 14aa, is hydrochloric acid.

In some embodiments, the compound of formula 14a is prepared by a process comprising:
reacting a compound of formula 13a:

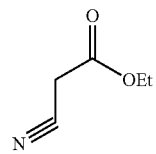

with bromoacetaldehyde diethyl acetal and sodium tert-amyloxide.

In some embodiments, the reacting of the compound of formula 13a with the bromoacetaldehyde diethyl acetal and sodium tert-amyloxide is carried out at a temperature of about 80° C. to about 100° C. In some embodiments, the reacting of the compound of formula 13a with the bromoacetaldehyde diethyl acetal and sodium tert-amyloxide is carried out in a solvent component, wherein the solvent component comprises a polar aprotic solvent. In some embodiments, the solvent component, present for the reacting of the compound of formula 13a with the bromoacetaldehyde diethyl acetal and the sodium tert-amyloxide, comprises dimethylsulfoxide.

In some embodiments, the compound of formula 3, or the salt thereof, is prepared by a process comprising:

reacting a compound of formula 6:

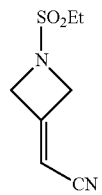

6 with hydrazine.

In some embodiments, the hydrazine is hydrazine hydrate.

In some embodiments, from about 1 to about 3 molar equivalents of the hydrazine are utilized relative to the compound of formula 6. In some embodiments, about 1.5 to about 2.5 molar equivalents of the hydrazine are utilized relative to the compound of formula 6. In some embodiments, about 2 to about 2.2 molar equivalents of the hydrazine are utilized relative to the compound of formula 6. In some embodiments, about 2.1 molar equivalents of the hydrazine are utilized relative to the compound of formula 6.

In some embodiments, the reacting of the compound of formula 6 is conducted in a solvent component. In some embodiments, the solvent component, present for the reacting of the compound of formula 6 with the hydrazine, comprises an organic solvent. In some embodiments, the solvent component, present for the reacting of the compound of formula 6 with the hydrazine, comprises an aprotic organic solvent. In some embodiments, the solvent component, present for the reacting of the compound of formula 6 with the hydrazine, comprises acetonitrile.

In some embodiments, the reacting of the compound of formula 6 with the hydrazine is conducted at a temperature of from about 20° C. to about 30° C. In some embodiments, the reacting of the compound of formula 6 with the hydrazine is conducted at an ambient temperature.

In some embodiments, the compound of formula 6 is prepared by a process comprising:

reacting a compound of formula 55:

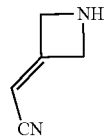

55 or a salt thereof, with ethane sulfonyl chloride to form a compound of formula 6.

In some embodiments, from about 1 to about 2 molar equivalents of the ethane sulfonyl chloride are utilized relative to the compound of formula 55, or the salt thereof. In some embodiments, about 1.5 molar equivalents of the ethane sulfonyl chloride are utilized relative to the compound of formula 55, or the salt thereof.

In some embodiments, the reacting of the compound of formula 55, or the salt thereof, with the ethane sulfonyl chloride, is conducted in the presence of a base. In some embodiments, the base, present for the reacting of the compound of formula 55, or the salt thereof, with the ethane sulfonyl chloride, is a tertiary amine. In some embodiments, the base, present for the reacting of the compound of formula 55, or the salt thereof, with the ethane sulfonyl chloride, is a tri-($C_{1-6}$ alkyl)amine. In some embodiments, the base, present for the reacting of the compound of formula 55, or the salt thereof, with the ethane sulfonyl chloride, is diisopropylethylamine.

In some embodiments, the reacting of the compound of formula 55, or the salt thereof, with the ethane sulfonyl chloride is conducted in a solvent component. In some embodiments, the solvent component, present for the reacting of the compound of formula 55, or the salt thereof, with the ethane sulfonyl chloride, comprises an organic solvent. In some embodiments, the solvent component, present for the reacting of the compound of formula 55, or the salt thereof, with the ethane sulfonyl chloride, comprises an aprotic organic solvent. In some embodiments, the solvent component, present for the reacting of the compound of formula 55, or the salt thereof, with the ethane sulfonyl chloride, comprises acetonitrile.

In some embodiments, the reacting of the compound of formula 55, or the salt thereof, with the ethane sulfonyl chloride is conducted at a temperature of from about −10° C. to about 30° C. In some embodiments, the temperature is about 0° C. to about 5° C. In some embodiments, the temperature is from about 0° C. to about 5° C. and then allowed to warm to room temperature.

In some embodiments, the compound of formula 55, or the salt thereof, is prepared by a process comprising:

deprotecting a compound of formula 54:

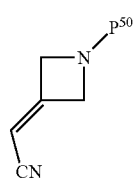

54 to form a compound of formula 55, or the salt thereof, wherein $P^{50}$ is a protecting group.

In some embodiments, $P^{50}$ is $R^{50}$—O—C(O)—, wherein $R^{50}$ is $C_{1-6}$ alkyl. In some embodiments, $R^{50}$ is methyl, ethyl, propyl, isopropyl, butyl, or t-butyl. In some embodiments, $P^{50}$ is t-butyl-O—C(O)—. In some embodiments, the deprotecting of the compound of formula 54 comprises treating the compound of formula 54 with a strong acid. In some embodiments, the strong acid, present for the deprotecting of the compound of formula 54, is HCl. In some embodiments, the deprotecting of the compound of formula 54 is conducted in a solvent component. In some embodiments, the solvent component, present for the deprotecting of the compound of formula 54, comprises a polar protic solvent and an organic solvent. In some embodiments, the solvent component, present for the deprotecting of the compound of formula 54, comprises an aprotic organic solvent. In some embodiments, the solvent component, present for the deprotecting of the compound of formula 54, comprises water and acetonitrile. In some embodiments, the deprotecting of the compound of formula 54 is conducted at an ambient temperature.

In some embodiments, the compound of formula 55, or the salt thereof, is the hydrochloride salt of the compound of formula 55.

In some embodiments, the compound of formula 54 is prepared by a process comprising:
reacting a compound of formula 7:

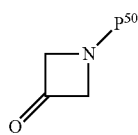

7 with diethyl cyanomethyl phosphate and a base to form a compound of formula 54.

In some embodiments, from about 1 to about 1.5 molar equivalents of the diethyl cyanomethyl phosphate are utilized relative to the compound of formula 7. In some embodiments, about 1.2 molar equivalents of the diethyl cyanomethyl phosphate are utilized relative to the compound of formula 7. In some embodiments, the base, present for the reacting of the compound of formula 7 with the diethyl cyanomethyl phosphate, is an alkali metal alkoxide. In some embodiments, the base, present for the reacting of the compound of formula 7 with the diethyl cyanomethyl phosphate, is potassium tert-butoxide.

In some embodiments, the reacting of the compound of formula 7 with the diethyl cyanomethyl phosphate and a base is carried out at a temperature between from about –20° C. to about 30° C. In some embodiments, the temperature is below about –5° C. In some embodiments, the temperature is from about –10° C. to about –5° C. and then allowed to warm to room temperature.

In some embodiments, the reacting of the compound of formula 7 with the diethyl cyanomethyl phosphate and a base is carried out in a solvent component, wherein the solvent component comprises an organic solvent. In some embodiments, the solvent component, present for the reacting of the compound of formula 7 with the diethyl cyanomethyl phosphate and the base, comprises a di-$C_{1-6}$ alkyl ether or a 4-10 membered heterocycloalkyl ether. In some embodiments, the solvent component, present for the reacting of the compound of formula 7 with the diethyl cyanomethyl phosphate and the base, comprises tetrahydrofuran.

In some embodiments, the compound of formula 7 is prepared by a process comprising:
oxidizing a compound of formula 56:

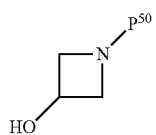

56 to form a compound of formula 7.

In some embodiments, the oxidizing of the compound of formula 56 is accomplished by a process comprising reacting the compound of formula 56 with TEMPO in the presence of sodium hypochlorite. In some embodiments, about 0.005 to about 0.02 equivalents of the TEMPO are utilized relative to the compound of formula 56. In some embodiments, about 0.01 equivalents of the TEMPO are utilized relative to the compound of formula 56. In some embodiments, the oxidizing the compound of formula 56 is carried out at a temperature between from about –10° C. to about 20° C. In some embodiments, the temperature is from about 0° C. to about 5° C.

In some embodiments, the oxidizing of the compound of formula 56 is carried out in a solvent component. In some embodiments, the solvent component, present for the oxidizing of the compound of formula 56, comprises water and an organic solvent. In some embodiments, the solvent component, present for the oxidizing of the compound of formula 56, comprises a polar aprotic solvent. In some embodiments, the solvent component, present for the oxidizing of the compound of formula 56, comprises ethyl acetate.

In some embodiments, the compound of formula 56 is prepared by a process comprising:
reacting a compound of formula 57:

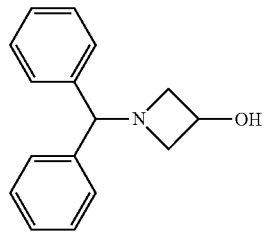

57 or a salt thereof, with hydrogen, a catalyst, and di-tert-butyl dicarbonate, wherein $P^{50}$ is tert-butyl-O—C(O)—.

In some embodiments, the catalyst, present for the reacting a compound of formula 57, or a salt thereof, with hydrogen and di-tert-butyl dicarbonate, is $Pd^0$ on carbon.

In some embodiments, from about 1 to about 1.5 molar equivalents of the di-tert-butyl dicarbonate are utilized relative to the compound of formula 57. In some embodiments, about 1.1 molar equivalents of the di-tert-butyl dicarbonate are utilized relative to the compound of formula 57. In some embodiments, the reacting of the compound of formula 57, or the salt thereof, with hydrogen, the catalyst, and di-tert-butyl dicarbonate is carried out at a pressure between from about 10 psi to about 50 psi. In some embodiments, the reacting of the compound of formula 57, or the salt thereof, with hydrogen, the catalyst, and di-tert-butyl dicarbonate is carried out at a pressure of about 30 psi. In some embodiments, the reacting of the compound of formula 57, or the salt thereof, with hydrogen, the catalyst, and di-tert-butyl dicarbonate is carried out at room temperature.

In some embodiments, the reacting of the compound of formula 57, or the salt thereof, with hydrogen, the catalyst, and di-tert-butyl dicarbonate is carried out in a solvent component, wherein the solvent component comprises an organic solvent. In some embodiments, the solvent component, present for the reacting of the compound of formula 57, or the salt thereof, with hydrogen, the catalyst, and di-tert-butyl dicarbonate, comprises a di-$C_{1-6}$ alkyl ether or a 4-10 membered heterocycloalkyl ether. In some embodiments, the solvent component, present for the reacting of the compound of formula 57, or the salt thereof, with hydrogen, the catalyst, and di-tert-butyl dicarbonate, comprises tetrahydrofuran.

In some embodiments, the compound of formula 57, or the salt thereof, is the hydrochloride salt of formula 57.

In some embodiments, the compound of formula 57, or the salt thereof, is prepared by a process comprising reacting diphenylmethanamine with 2-(chloromethyl)oxirane. In some embodiments, about 1 to about 1.1 molar equivalents of the diphenylmethanamine are utilized relative to the 2-(chloromethyl)oxirane. In some embodiments, the reacting the diphenylmethanamine with the 2-(chloromethyl)oxirane is carried out at a temperature between from about 20° C. to about 80° C. In some embodiments, the reacting the diphenylmethanamine with the 2-(chloromethyl)oxirane is carried out at room temperature and then heated to the refluxing temperature of methanol. In some embodiments, the reacting the diphenylmethanamine with the 2-(chloromethyl)oxirane is carried out in a solvent component, wherein the solvent component comprises a polar protic solvent. In some embodiments, the solvent component, present for the reacting of the diphenylmethanamine with the 2-(chloromethyl)oxirane, comprises an alcohol. In some embodiments, the solvent component, present for the reacting of the diphenylmethanamine with the 2-(chloromethyl)oxirane, comprises formula $C_{1-6}$ alkyl-OH. In some embodiments, the solvent component, present for the reacting of diphenylmethanamine with 2-(chloromethyl)oxirane, comprises methanol.

The present disclosure further provides processes of preparing baricitinib, or a salt thereof, comprising reacting a salt of formula 2c:

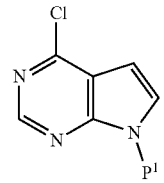

with a compound of formula 3:

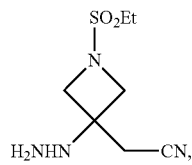

to form the baricitinib, or the salt thereof.

In some embodiments, the salt of formula 2c is prepared by a process comprising reacting a salt of formula 2d:

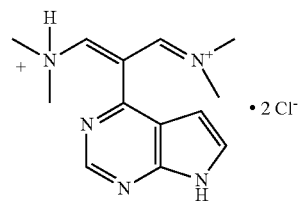

with a base to form the salt of formula 2c.

In some embodiments, the salt of formula 2d is prepared by a process comprising:

(a) reacting a compound of formula 2P:

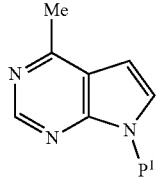

with MeMgBr in the presence of a Grignard catalyst to form a compound of formula 1aP:

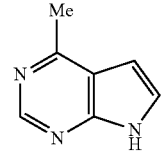

(b) deprotecting the compound of formula 1 aP to form a compound of formula 1a:

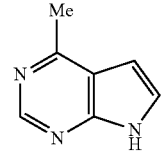

or a salt thereof; and (c) reacting the compound of formula 1a, or the salt thereof, with a Vilsmeier reagent formed from dimethylformamide and a chlorinating agent to form the salt of formula 2d;

wherein $P^1$ is an amino protecting group. In some embodiments, $P^1$ is trimethylsilyl.

In some embodiments, the salt of formula 2d is prepared by a process comprising:

(a) reacting a compound of formula 22P:

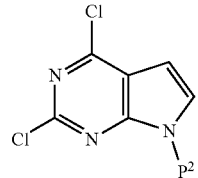

22P with MeMgBr in the presence of a Grignard catalyst to form a compound of formula 23P:

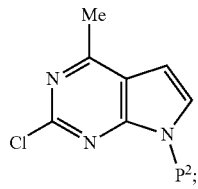

23P (b) reducing the compound of formula 23P to form a compound of formula 1a:

1a or a salt thereof; and (c) reacting the compound of formula 1a, or the salt thereof, with a Vilsmeier reagent formed from dimethylformamide and a chlorinating agent to form the salt of formula 2d;

wherein $P^2$ is an amino protecting group. In some embodiments, $P^1$ is t-butyldimethylsilyl.

In some embodiments, the compound of formula 3, or the salt thereof, is prepared by a process comprising:

reacting a compound of formula 6:

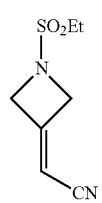

6 with hydrazine.

In some embodiments, provided herein is a process of preparing baricitinib, or a salt thereof, comprising:

(a) reacting a compound of formula 1a, or a salt thereof:

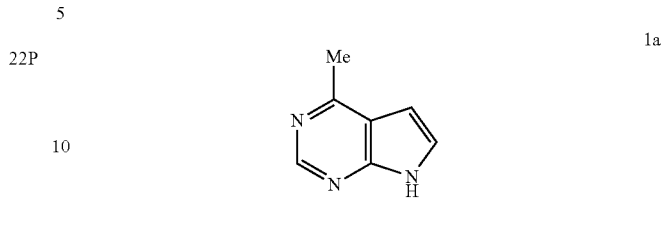

1a with a Vilsmeier reagent formed from dimethylformamide to generate a salt of formula 2c:

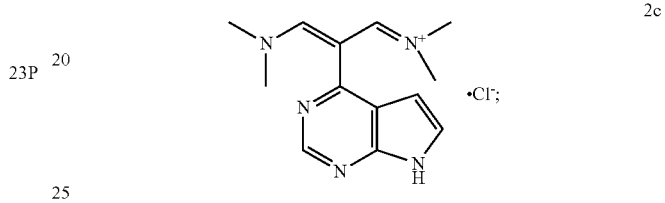

2c (b) reacting the salt of formula 2c with a salt of formula $M^+ClO_4^-$ to generate a salt of formula 2a:

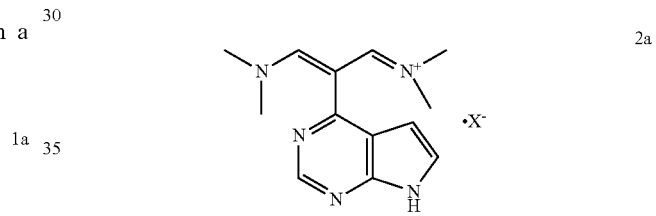

2a wherein $M^+$ is a counter cation and $X^-$ is $ClO_4^-$; and (c) reacting the salt of formula 2a with a compound of formula 3:

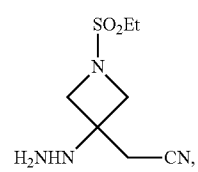

3 or a salt thereof, to form baricitinib, or the salt thereof.

In some embodiments, provided herein is a process of preparing baricitinib, or a salt thereof, comprising:

(a) reacting a compound of formula 5a:

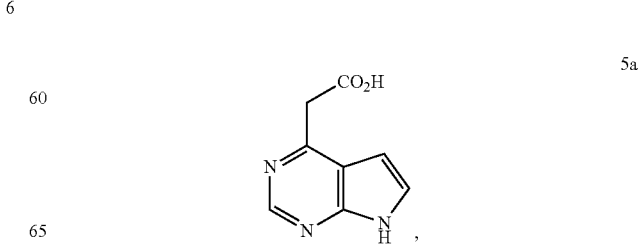

5a with a Vilsmeier reagent formed from dimethylformamide to generate a salt of formula 2c:

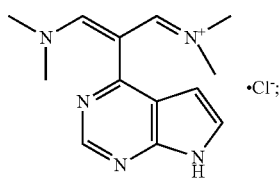

2c (b) reacting the salt of formula 2c with a salt of formula $M^+ClO_4^-$ to generate a salt of formula 2a:

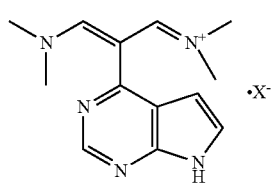

2a wherein $M^+$ is a counter cation and $X^-$ is $ClO_4^-$; and
(c) reacting the salt of formula 2a with a compound of formula 3:

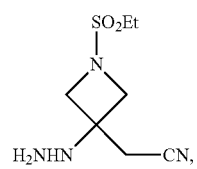

3 or a salt thereof, to form the baricitinib, or the salt thereof.

In some embodiments, provided herein is a process of preparing baricitinib, or a salt thereof, comprising:
(a) reacting a compound of formula 6:

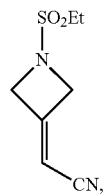

6 with hydrazine to generate a compound of formula 3:

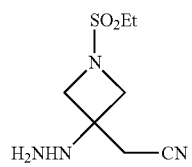

3 or a salt thereof; and
(b) reacting the compound of formula 3, or the salt thereof, with a salt of formula 2a:

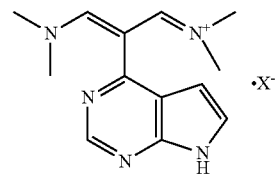

2a wherein $M^+$ is a counter cation and $X^-$ is $ClO_4^-$, to generate the baricitinib, or the salt thereof.

In some embodiments, the compound of formula 1a:

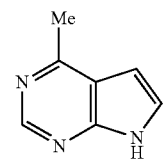

1a or a salt thereof, is prepared by a process comprising:
(a) reacting a compound of formula 12a:

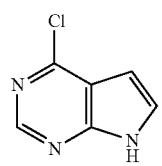

12a with trimethylsilyl chloride to generate a compound of formula 2P:

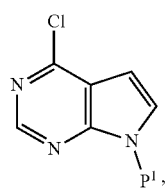

2P wherein $P^1$ is trimethylsilyl;
(b) reacting the compound of formula 12b with MeMgBr in the presence of a Grignard catalyst to generate a compound of formula 12c:

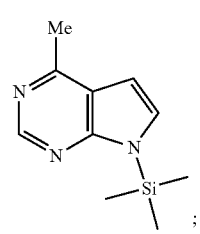

12d and
(c) deprotecting the compound of formula 12d to form the compound of formula 1a, or the salt thereof.

In some embodiments, the compound of formula 12a:

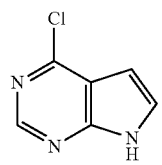

is prepared by a process comprising:
(a) reacting a compound of formula 13a:

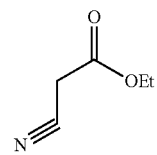

with bromoacetaldehyde diethyl acetal and sodium tert-amyloxide to generate a compound of formula 14a:

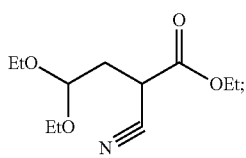

(b) reacting the compound of formula 14a with formamidine acetate and an alkali metal alkoxide to generate a compound of formula 14aa:

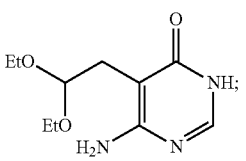

(c) reacting the compound of formula 14aa with a strong acid to generate a compound of formula 15a:

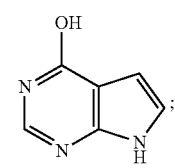

and
(d) reacting the compound of formula 15a with a chlorinating agent to form the compound of formula 12a.

In some embodiments, the compound of formula 1a:

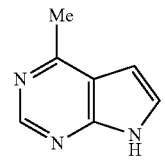

or a salt thereof, is prepared by a process comprising:
(a) reacting a compound of formula 22a:

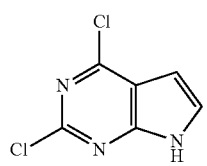

with t-butyldimethylsilyl chloride and an alkali metal hydride to generate a compound of formula 22P:

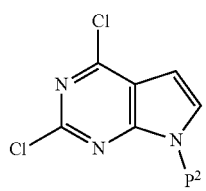

wherein $P^2$ is t-butyldimethylsilyl;
(b) reacting the compound of formula 22P with MeMgBr in the presence of a Grignard catalyst to generate a compound of formula 23a:

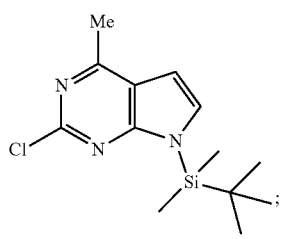

and
(c) reducing the compound of formula 23a with hydrogen and palladium on carbon to form the compound of formula 1a, or the salt thereof;
wherein $P^2$ is an amino protecting group.

In some embodiments, the compound of formula 6 is prepared by a process comprising:
(a) reacting diphenylmethanamine with 2-(chloromethyl)oxirane to generate a compound of formula 57, or a salt thereof:

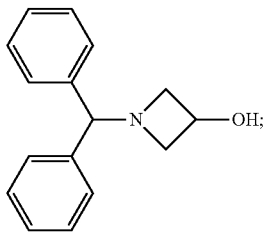

(b) reacting the compound of formula 57, or the salt thereof, with hydrogen, palladium on carbon, and di-tert-butyl dicarbonate to generate a compound of formula 56a:

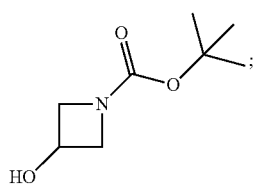

(c) oxidizing the compound of formula 56a to generate a compound of formula 7a:

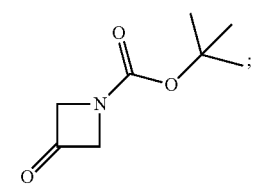

(d) reacting the compound of formula 7a with diethyl cyanomethyl phosphate and a base to generate a compound of formula 54a:

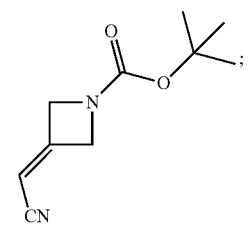

(e) deprotecting the compound of formula 54a to generate a compound of formula 55, or a salt thereof:

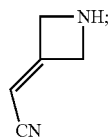

and (f) reacting the compound of formula 55, or the salt thereof, with ethane sulfonyl chloride to form the compound of formula 6.

In some embodiments, provided herein is a compound of formula 3:

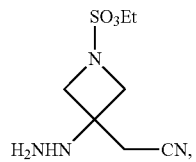

or a salt thereof.

In some embodiments, provided herein is a process of making a compound of formula 3, or a salt thereof, comprising:

reacting a compound of formula 6:

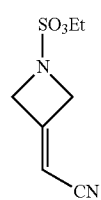

with hydrazine.

In some embodiments, the hydrazine is hydrazine hydrate. In some embodiments, from about 1 to about 3 molar equivalents of the hydrazine are utilized relative to the compound of formula 6. In some embodiments, from about 1.5 to about 2.5 molar equivalents of the hydrazine are utilized relative to the compound of formula 6. In some embodiments, from about 2 to about 2.2 molar equivalents of the hydrazine are utilized relative to the compound of formula 6. In some embodiments, about 2.1 molar equivalents of the hydrazine are utilized relative to the compound of formula 6. In some embodiments, the reacting of the compound of formula 6 with the hydrazine is conducted in a solvent component. In some embodiments, the solvent component, present for the reacting of the compound of formula 6 with the hydrazine, comprises an organic solvent. In some embodiments, the solvent component, present for the reacting of the compound of formula 6 with the hydrazine, comprises an aprotic organic solvent. In some embodiments, the solvent component, present for the reacting of the compound of formula 6 with the hydrazine, comprises acetonitrile. In some embodiments, the reacting of the compound of formula 6 with the hydrazine is conducted at a temperature of from about 20° C. to about 30° C. In some embodiments, the reacting of the compound of formula 6 with the hydrazine is conducted at an ambient temperature.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl", employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl. In some embodiments, the alkyl moiety is methyl.

As used herein, the terms "halo" and "halogen", employed alone or in combination with other terms, refer to fluoro, chloro, bromo, and iodo.

As used herein, the term "4-10 membered heterocycloalkyl ether" refers to a non-aromatic ring or ring system, which optionally contain one or more alkenylene groups as part of the ring structure, which has at least one oxygen heteroatom ring member and 4-10 ring members. Included within the term "heterocycloalkyl" are monocyclic 4-, 5-, 6- and 7-membered heterocycloalkyl groups. Examples of 4-10 membered heterocycloalkyl ether include tetrahydrofuran, tetrahydropyran, dioxane, and the like.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, or spectrophotometry (e.g., UV-visible); or by chromatography such as high performance liquid chromatography (HPLC) or thin layer chromatography (TLC) or other related techniques.

As used herein, the terms "reacting" and "contacting" are used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent.

The reacting steps of the processes described herein can be conducted for a time and under conditions suitable for preparing the identified product.

In some embodiments, the reagents and intermediates may be salts.

The compounds of the present disclosure also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi- salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloro ethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable solvents can include ether solvents such as: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, benzyl alcohol, phenol, glycerol, mixtures thereof, and the like.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, mixtures thereof, and the like.

Suitable hydrocarbon solvents include benzene, cyclohexane, pentane, hexane, toluene, cycloheptane, methylcyclohexane, heptane (e.g., n-heptane), ethylbenzene, m-, o-, or p-xylene, octane, indane, nonane, naphthalene, mixtures thereof, and the like.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to affect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include alkali metal hydroxides (e.g., lithium hydroxide, sodium hydroxide, and potassium hydroxide), and alkali metal carbonate (e.g., lithium carbonate, sodium carbonate, and potassium carbonate). Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The present disclosure also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in Remington's Pharmaceutical Sciences, 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

In some embodiments, baricitinib, intermediates for preparing baricitinib reagents, and salts thereof can include both anhydrous forms of that substance and solvated/hydrated forms of that substance. Different forms of the same substance have different bulk properties relating to, for example, hygroscopicity, solubility, stability, and the like. Forms with high melting points often have good thermodynamic stability which is advantageous in prolonging shelf-life drug formulations comprising the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

In some embodiments, the disclosed compounds, or salts thereof are crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

The different solid forms and salt forms thereof can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

Generally, the term "about" means±10%. In some embodiments, the term "about" means±5%.

In some embodiments, the solid forms and salt forms are substantially isolated. By "substantially isolated" is meant that the solid form, salt form or crystalline form thereof is at least partially or substantially separated from the environment in which it was formed or detected. Partial separation can include, for example, a composition enriched in the solid forms and salt forms. Substantial separation can include compositions containing at least about 50%, at least about 60%, at least about 70%, at least about 80%, at least about 90%, at least about 95%, at least about 97%, or at least about 99% by weight of the solid forms and salt forms. Methods for isolating solid forms and salt forms thereof are routine in the art.

In some embodiments, the solid forms and salt forms described herein can be found together with other substances such as water and solvents (e.g., hydrates and solvates) or can be isolated.

The phrase "pharmaceutically acceptable" is employed herein to refer to those salts, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The reactions described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g., a reaction temperature, that is about the temperature of the room in which the reaction is carried out, for example, a temperature from about 20° C. to about 30° C.

The protecting groups (e.g., $P^1$, $P^2$, $P^{50}$, etc.) described herein include, but are not limited to, the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. Examples of protecting groups as described herein include $CH_2OC(=O)C(CH_3)_3$, $CH_2OCH_2CH_2Si(CH_3)_3$, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl(Tsc), t-butoxycarbonyl (BOC), 1-adamantyloxycarbonyl(Adoc), 2-adamantylcarbonyl(2-Adoc), 2,4-dimethylpent-3-yloxycarbonyl(Doc), cyclohexyloxycarbonyl(Hoc), 1,1-dimethyl-2,2,2-trichloroethoxycarbonyl(TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl(Bum), benzyloxymethyl (BOM), 2-tetrahydropyranyl (THP), tri($C_{1-4}$ alkyl)silyl (e.g., tri(isopropyl)silyl or t-butyldimethylsilyl), 1,1-diethoxymethyl, 2-(trimethylsilyl)ethoxymethyl (SEM), N-pivaloyloxymethyl (POM), p-nitrophenylsulfonyl, p-toluenesulfonyl, phenylsulfonyl, methanesulfonyl, and the like. In some embodiments, the protecting group is tri($C_{1-4}$ alkyl) silyl (e.g., tri(isopropyl)silyl or t-butyldimethylsilyl). In some embodiments, the protecting group is t-butyldimethylsilyl. In some embodiments, the protecting group is p-toluenesulfonyl.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1. Preparation of 2- (3- (4- (7H-Pyrrolo[2, 3-d]pyrimidin-4-yl)-1H-pyrazol-1-yl)-1-(ethylsulfonyl)azetidin-3-yl)acetonitrile (Baricitinib, Compound 1)

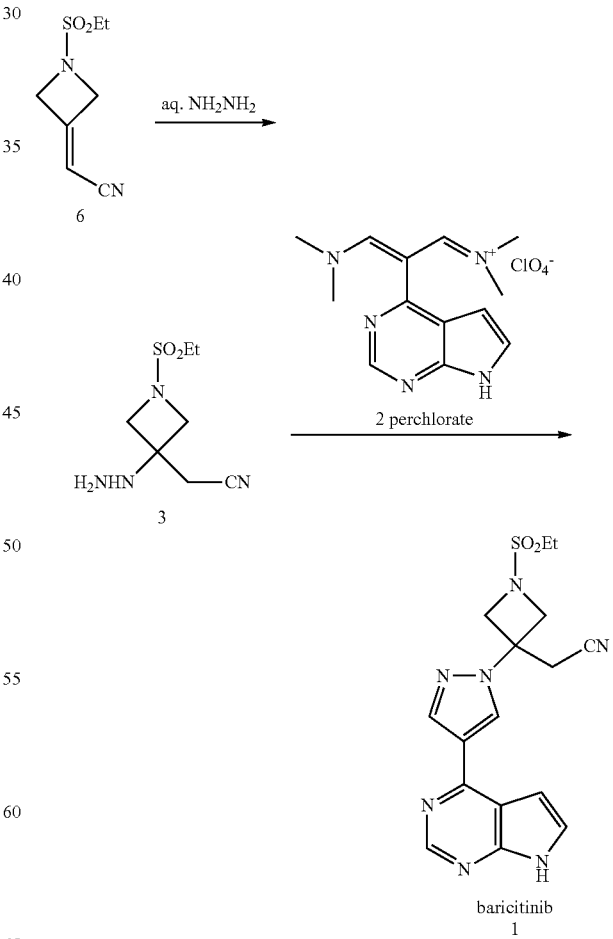

Step 1. 2-(1-(Ethylsulfonyl)-3-hydrazineylazetidin-3-yl)acetonitrile (Compound 3)

To a flask under nitrogen was charged 2-(1-(ethylsulfonyl)azetidin-3-ylidene)acetonitrile (Compound 6, 1.0 g, 5.37 mmol) and acetonitrile (10 mL). Hydrazine hydrate (0.66 g, 11.3 mmol, 2.1 equiv) was slowly addded to the reaction mixture over 30 minutes with reaction temperature controlled at below 25° C. The reaction was completed after stirring at ambient temperature for 2 hours. Upon completion, the reaction solvent was evaporated in vacuo. The residual reaction mixture was diluted by dichloromethane ($CH_2Cl_2$, 20 mL) and washed by brine (10 mL). The organic layer was separated and collected. The aqueous layer was extracted by another portion of dichloromethane ($CH_2Cl_2$, 10 mL), and the organic layer was collected. The combined organic layer was evaporated in vacuo. The crude desired product, 2-(1-(ethylsulfonyl)-3-hydrazineylazetidin-3-yl)acetonitrile (Compound 3, 0.82 g, 72%), was obtained as a gel, which was directly used in the next step without further purification. For Compound 3: $^1$H NMR (CDCl$_3$, 400 MHz) δ 3.97 (d, J=8.8 Hz, 2H), 3.68 (d, J=8.9 Hz, 2H), 3.35 (br, 3H), 2.99 (q, J=7.4 Hz, 2H), 2.93 (s, 2H), 1.33 (t, J=7.4 Hz, 3H) ppm; $^{13}$C NMR (CDCl$_3$, 101 MHz) δ 117.22, 57.43, 55.36, 45.72, 24.69, 7.86 ppm; $C_7H_{14}N_4O_2$ (MW: 218.28), LCMS (EI) m/e 219.2(M$^+$+H).

Step 2. 2-(3-(4-(7H-Pyrrolo[2,3-d]pyrimidin-4-yl)-1H-pyrazol-1-yl)-1-(ethylsulfonyl)azetidin-3-yl)acetonitrile (Baricitinib, Compound 1)

To a solution of 2-(1-(ethylsulfonyl)-3-hydrazineylazetidin-3-yl)acetonitrile (Compound 3, 0.84 g, 3.85 mmol, 1.32 equiv) in ethanol (8 mL) was added vinamidinium perchlorate (Compound 2 perchlorate, 1.0 g, 2.91 mmol) in one portion. The resulting reaction mixture was stirred at ambient temperature for 16 hours. To the reaction mixture was added n-heptane (16 mL) and the resulting mixture was stirred at ambient temperature for another hour. The reaction mixture was filtered and the solid was washed by n-heptane (10 mL). After drying overnight by pulling air through the wet cake, the desired product, 2-(3-(4-(7H-pyrrolo[2,3-d]pyrimidin-4-yl)-1H-pyrazol-1-yl)-1-(ethylsulfonyl)azetidin-3-yl)acetonitrile (Baricitinib, Compound 1, 1.2 g, 85%), was obtained as a brown solid. For Baricitinib (Compound 1): $^1$H NMR (DMSO-d$_6$, 300 MHz) δ 12.15 (s, 1H), 8.94 (s, 1H), 8.72 (s, 1H), 8.49 (s, 1H), 7.63 (d, 1H), 7.09 (d, 1H), 4.62 (d, 2H), 4.25 (d, 2H), 3.71 (s, 2H), 3.24 (q, 2H), 1.26 (t, 3H) ppm; $C_{16}H_{17}N_7O_2S$ (MW, 371.42), LCMS (EI) m/e 372 (M$^+$+H).

Example 2. Preparation of 2-(1-(Ethylsulfonyl)azetidin-3-ylidene)acetonitrile (Compound 6)

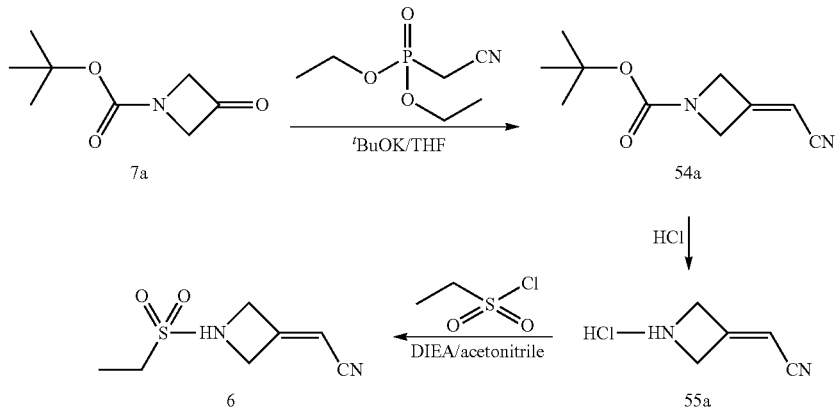

Step 1. tert-Butyl 3-(cyanomethylene)azetidine-1-carboxylate (Compound 54a)

Diethyl cyanomethyl phosphate (745 g, 4.20 mol, 1.20 equiv) and anhydrous tetrahydrofuran (THF, 9 L) were added to a four-neck flask equipped with a thermowell, an addition funnel and a nitrogen protection tube at room temperature. The solution was cooled with an ice-methanol bath to −14° C. and a 1.0 M solution of potassium tert-butoxide (t-BuOK) in anhydrous tetrahydrofuran (THF, 3.85 L, 3.85 mol, 1.1 equiv) was added over 20 min keeping the reaction temperature below −5° C. The resulting reaction mixture was stirred for 3 h at −10° C. and a solution of tert-butyl 3-oxoazetidine-1-carboxylate (Compound 7a, 600 g, 3.50 mol) in anhydrous tetrahydrofuran (THF, 2 L) was added over 2 h keeping the internal temperature below −5° C. The reaction mixture was stirred at −5 to −10° C. over 1 h and then slowly warmed up to room temperature and stirred at room temperature for overnight. The reaction mixture was then diluted with water (4.5 L) and saturated aqueous sodium chloride solution (NaCl, 4.5 L) and extracted with ethyl acetate (EtOAc, 2×9 L). The combined organic layers were washed with brine (6 L) and dried over anhydrous sodium sulfate ($Na_2SO_4$). The organic solvent was removed under reduced pressure and the residue was diluted with dichloromethane ($CH_2Cl_2$, 4 L) before being absorbed onto silica gel ($SiO_2$, 1.5 Kg). The crude product, which was absorbed on silica gel, was purified by flash column chromatography ($SiO_2$, 3.5 Kg, 0-25% EtOAc/hexanes gradient elution) to afford tert-butyl 3-(cyanomethylene)azetidine-1-carboxylate (Compound 54a, 414.7 g, 679.8 g theoretical, 61% yield) as white solid. For Compound 54a: $^1$HNMR (CDCl$_3$, 300 MHz), δ 5.40 (m, 1H), 4.70 (m, 2H), 4.61 (m, 2H), 1.46 (s, 9H) ppm; $C_{10}H_{14}N_2O_2$ (MW, 194.23), LCMS(EI) m/e 217 (M$^+$+Na).

Step 2. 2-(1-(Ethylsulfonyl)azetidin-3-ylidene)acetonitrile (Compound 6):

A solution of tert-butyl 3-(cyanomethylene)azetidine-1-carboxylate (Compound 54a, 1000 g, 5.2 mol) in acetonitrile (7 L) and a 3N aqueous HCl solution (7 L) was stirred at room temperature for 18 h. When HPLC showed that all the starting material (tert-butyl 3-(cyanomethylene)azetidine-1-carboxylate) was consumed, the reaction mixture was concentrated under reduced pressure to dryness. The residue, which contains the crude desired deprotection product (Compound 55a), was then suspended in acetonitrile (12 L) and the resulting suspension was cooled to 0-5° C. Diisopropyethylamine (DIEA, 3.14 L, 18.03 mol, 3.5 equiv) was then slowly added while keeping the internal temperature below 5° C. The resulting homogeneous solution was allowed to cool down to 0° C. and ethane sulfonyl chloride (EtSO$_2$Cl, 730 mL, 7.73 mol, 1.5 equiv) was added over 1 h while keeping the internal temperature below 5° C. The resulting reaction mixture was allowed to gradually warm to room temperature and stirred at room temperature for overnight. When HPLC showed that the reaction was complete, the reaction mixture was concentrated under reduced pressure to a volume of approximate 2 L. The bath temperature of the rotary evaporator was set to not exceed 45° C. The concentrated residue was then diluted with dichloromethane (CH$_2$Cl$_2$, 10 L) and the resulting dichloromethane solution was washed with aqueous sodium chloride solution (10 L). The aqueous phase was back extracted with dichloromethane (CH$_2$Cl$_2$, 5 L). The combined organic layers were dried over anhydrous sodium sulfate (Na$_2$SO$_4$) and the residue was absorbed onto silica gel (SiO$_2$, 1 Kg) under reduced pressure. The bath temperature of the rotary evaporator was set to not exceed 45° C. The material was then loaded onto a silica gel column (SiO$_2$, 2.5 Kg) and eluted with 20-60% ethyl acetate in heptane to afford 2-(1-(ethylsulfonyl)azetidin-3-ylidene)acetonitrile (Compound 6, 882 g, 968.4 g theoretical, 91% yield) as off-white solids. For Compound 6: $^1$H NMR (CDCl$_3$, 300 MHz) δ 5.46 (m, 1H), 4.77 (m, 2H), 4.70 (m, 2H), 3.05 (q, 2H), 1.39 (t, 3H) ppm; C$_7$H$_{10}$N$_2$O$_2$S (MW, 186.23), LCMS (EI) mle 187 (M$^+$+H).

Example 3. Preparation of tert-Butyl 3-oxoazetidine-1-carboxylate (Compound 7a)

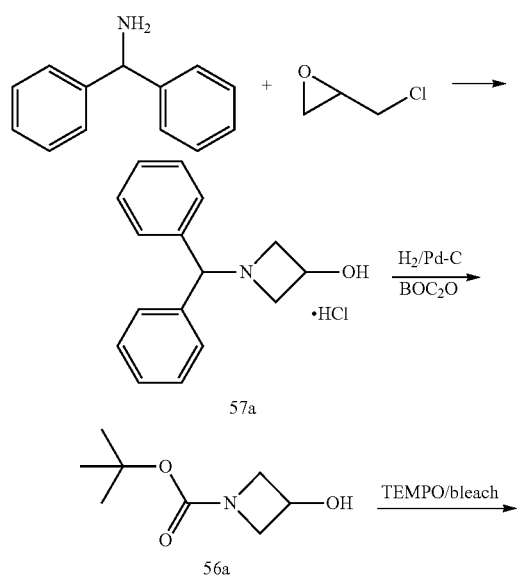

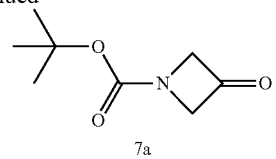

7a

Step 1. 1-Benzhydrylazetidin-3-ol hydrochloride (Compound 57a)

A solution of diphenylmethanamine (2737 g, 15.0 mol, 1.04 equiv) in methanol (MeOH, 6 L) was treated with 2-(chloromethyl)oxirane (1330 g, 14.5 mol) from an addition funnel at room temperature. During the initial addition a slight endotherm was noticed. The resulting reaction mixture was stirred at room temperature for 3 days before being warmed to reflux for an additional 3 days. When TLC showed that the reaction was deemed complete, the reaction mixture was first cooled down to room temperature and then to 0-5° C. in an ice bath. The solids were collected by filtration and washed with acetone (4 L) to give the first crop of the crude desired product (1516 g). The filtrate was concentrated under reduced pressure and the resulting semisolid was diluted with acetone (1 L). This solid was then collected by filtration to give the second crop of the crude desired product (221 g). The crude product, 1-benzhydrylazetidin-3-ol hydrochloride (Compound 57a, 1737 g, 3998.7 g theoretical, 43.4% yield), was found to be sufficiently pure to be used in the subsequent reaction without further purification. For Compound 57a: $^1$HNMR (DMSO-d$_6$, 300 MHz), δ 12.28 (br. d, 1H), 7.7 (m, 5H), 7.49 (m, 5H), 6.38 (d, 1H), 4.72 (br. s, 1H), 4.46 (m, 1H), 4.12 (m, 2H), 3.85 (m, 2H) ppm; C$_{16}$H$_{18}$C$_1$NO (free base of 57a, C$_{16}$H$_{17}$NO MW, 239.31), LCMS (EI) mle 240 (M$^+$+H).

Step 2. tert-Butyl 3-hydroxyazetidine-1-carboxylate (Compound 56a)

A suspension of 1-benzhydrylazetidin-3-ol hydrochloride (Compound 57a, 625 g, 2.27 mol) in a 10% solution of aqueous sodium carbonate (Na$_2$CO$_3$, 5 L) and dichloromethane (CH$_2$Cl$_2$, 5 L) was stirred at room temperature until all solids were dissolved. The two layers were separated, and the aqueous layer was extracted with dichloromethane (CH$_2$Cl$_2$, 2 L). The combined organic extracts were dried over sodium sulfate (Na$_2$SO$_4$) and concentrated under reduced pressure. This resulting crude free base of 1-benzhydrylazetidin-3-ol hydrochloride was then dissolved in tetrahydrofuran (THF, 6 L) and the solution was placed into a large Parr bomb. Di-tert-butyl dicarbonate (BOC$_2$O, 545 g, 2.5 mol, 1.1 equiv) and 20% palladium (Pd) on carbon (125 g, 50% wet) were added to the Parr bomb. The vessel was charged to 30 psi with hydrogen gas (H$_2$) and stirred under steady hydrogen atmosphere (vessel was recharged three times to maintain the pressure at 30 psi) at room temperature for 18 h. When HPLC showed that the reaction was complete (when no more hydrogen was taken up), the reaction mixture was filtered through a Celite pad and the Celite pad was washed with THF (4 L). The filtrates were concentrated under reduced pressure to remove the solvent and the residue was loaded onto a Biotage 150 column with a minimum amount of dichloromethane (CH$_2$Cl$_2$). The column was eluted with 20-50% ethyl acetate in heptane and the fractions containing the pure desired product were collected and combined. The solvents were removed under reduced pressure to afford tert-butyl 3-hydroxyazetidine-1-carboxylate (Compound 56a, 357 g, 393.2 g theoretical, 90.8% yield) as colorless oil, which solidified upon standing at room temperature in vacuum. For Compound 56a: $^1$HNMR (CDCl$_3$, 300 MHz), δ 4.56 (m 1H), 4.13 (m, 2H), 3.81 (m, 2H), 1.43 (s, 9H) ppm.

Step 3. tert-Butyl 3-oxoazetidine-1-carboxylate (Compound 7a)

A solution of tert-butyl 3-hydroxyazetidine-1-carboxylate (Compound 56a, 50 g, 289 mmol) in ethyl acetate (400 mL) was cooled to 0° C. The resulting solution was then treated with solid TEMPO (0.5 g, 3.2 mmol, 0.011 equiv) and a solution of potassium bromide (KBr, 3.9 g, 33.2 mmol, 0.115 equiv) in water (60 mL) at 0-5° C. While keeping the reaction temperature between 0-5° C., a solution of saturated aqueous sodium bicarbonate (NaHCO$_3$, 450 mL) and an aqueous sodium hypochlorite solution (NaClO, 10-13% available chlorine, 450 mL) were added. Once the solution of sodium hypochlorite was added, the color of the reaction mixture changed immediately. When additional amount of sodium hypochlorite solution was added, the color of the reaction mixture gradually faded. When TLC showed that all of the starting material was consumed, the color of the reaction mixture was no longer changed. The reaction mixture was then diluted with ethyl acetate (EtOAc, 500 mL) and two layers were separated. The organic layer was washed with water (500 mL) and saturated aqueous sodium chloride solution (500 mL) and dried over sodium sulfate (Na$_2$SO$_4$). The solvent was then removed under reduced pressure to give the crude product, tert-butyl 3-oxoazetidine-1-carboxylate (Compound 7a, 48 g, 49.47 g theoretical, 97% yield), which was found to be sufficiently pure and was used directly in the subsequent reaction without further purification. For crude Compound 7a: $^1$HNMR (CDCl$_3$, 300 MHz), δ 4.65 (s, 4H), 1.42 (s, 9H) ppm.

Example 4. Preparation of (E)-N-(3-(Dimethyl-amino)-2-(7H-pyrrolo[2,3- -d]pyrimidin-4-yl)ally-lidene)-N-methylmethanaminium chloride hydrochloride (Compound 2 chloride hydrochloride or Compound 2d)

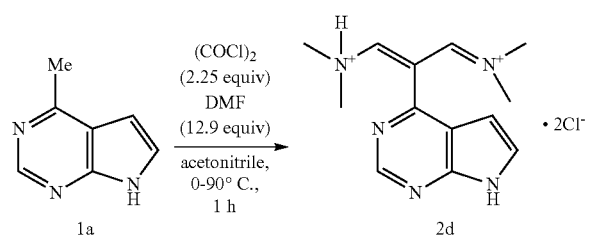

A solution of oxalyl chloride (21.88 g, 15.1 mL, 169 mmol, 2.25 equiv) in anhydrous acetonitrile (65 mL) was cooled to 0-5° C. in an ice bath. Anhydrous DMF (70.8 g, 75.0 mL, 969 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature over 40 minutes. Methyl-7H-pyrrolo[2,3-d]pyrimidine (1a, 10.0 g, 75.1 mmol) was charged into the in-situ generated Vilsmeier reagent as a solid in one portion at ambient temperature and the resulting slurry was agitated at ambient temperature for 5-10 minutes to ensure complete mixing before being warmed to 85-90° C. The reaction mixture was agitated at 85-90° C. for one hour before being gradually cooled to ambient temperature. Anhydrous tetrahydrofuran (THF, 100 mL) was charged and the resulting slurry was agitated at ambient temperature for two hours followed by at 0-5° C. for two hours. The solids were collected by filtration, washed with a one to one mixture of THF and MTBE (2×100 mL), and dried under vacuum to constant weight to afford the desired product, (E)-N-(3-(Dimethylamino)-2-(7H-pyrrolo[2,3-d]pyrimidin-4-yl)allylidene)-N-methylmethanaminium chloride hydrochloride (2d, 24.38 g, 23.72 g theoretical, 98.9% by HPLC area %, 90.2 wt % by NMR, 92.6% yield), as a yellow to brown crystalline solid (Form I), which contained 6-7% of DMF and acetonitrile and 1-2% of water and was used in the subsequent reaction without further purification. For Compound 2d: $^1$H NMR (500 MHz, DMSO-d$_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-d$_6$, 125 MHz) δ 163.8, 151.3, 147.6, 145.0, 132.1, 117.5, 102.9, 91.6, 48.9, 42.1 ppm; C$_{13}$H$_{19}$Cl$_2$N$_5$ (MW, 279.77 for Compound 2c and 244.32 for Compound 2 without anion) LCMS (EI) mle 244.2 (M$^+$, base peak).

Crystalline Form I of Compound 2d was characterized by XRPD, DSC and TGA.

X-Ray Powder Diffraction (XRPD): The X-Ray Powder Diffraction (XRPD) was obtained from Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

Form I of Compound 2d was confirmed to be crystalline solid according to XRPD analysis. The XRPD pattern of Compound 2d crystalline Form I is shown in FIG. 1 and the peak data is given in Table 1.

TABLE 1

XRPD Peak Data for Compound 2d Form I

| 2-Theta (°) | Relative Intensity (%) |
|---|---|
| 7.4 | 14.9 |
| 9.2 | 1.9 |
| 11.0 | 3.4 |
| 11.5 | 0.8 |
| 12.5 | 40.1 |
| 13.1 | 11.4 |
| 14.1 | 28.9 |
| 14.6 | 34.0 |
| 15.0 | 10.2 |
| 15.5 | 1.0 |
| 15.9 | 17.3 |
| 17.3 | 2.8 |
| 17.7 | 18.4 |
| 18.5 | 57.3 |
| 19.0 | 10.2 |
| 19.5 | 0.6 |
| 20.5 | 19.1 |
| 20.8 | 42.2 |
| 21.1 | 3.2 |
| 21.3 | 1.8 |
| 22.2 | 53.8 |
| 23.0 | 15.9 |

TABLE 1-continued

XRPD Peak Data for Compound 2d Form I

| 2-Theta (°) | Relative Intensity (%) |
|---|---|
| 23.1 | 3.6 |
| 24.1 | 11.5 |
| 24.3 | 26.7 |
| 24.9 | 3.2 |
| 25.3 | 18.9 |
| 25.5 | 16.9 |
| 26.0 | 22.4 |
| 26.3 | 100 |
| 27.2 | 1.9 |
| 27.9 | 81.5 |
| 28.2 | 6.3 |
| 28.8 | 11.7 |
| 29.2 | 19.8 |
| 29.5 | 3.9 |

Differential Scanning calorimetry (DSC): The DSC was obtained from TA Instruments Differential Scanning calorimetry, Discovery DSC2500 with autosampler. The DSC instrument conditions were as follows: 20-300° C. at 10° C./min; Tzero aluminum sample pan and lid; and nitrogen gas flow at 50 mL/min. DSC analysis of Compound 2d crystalline Form I revealed one endothermic peak with an onset temperature of 55.6° C. and a maximum at 100.6° C. The DSC thermogram of Compound 2d crystalline Form I is provided in in FIG. 2.

Thermogravimetric Analysis (TGA): The TGA was obtained from TA Instruments Thermogravimetric Analyzer, Discovery TGA5500 with autosampler. The general experimental conditions for TGA were: ramp from 25° C. to 300° C. at 10° C./min; nitrogen purge gas flow at 25 mL/min; platinum sample holder. TGA analysis of Compound 2d crystalline Form I revealed 8.0% weight loss below 100° C. and significant weight loss above 175° C. due to decomposition. The TGA thermogram of Compound 2d crystalline Form I is provided in in FIG. 3.

Example 5: Alternative Preparation of (E)-N-(3-(Dimethylamino)-2-(7H-pyrrolo[2,3-d]pyrimidin-4-yl)allylidene)-N-methylmethanaminium chloride hydrochloride (Compound 2d)

A solution of oxalyl chloride (43.76 g, 30.2 mL, 338 mmol, 2.25 equiv) in anhydrous acetonitrile (130 mL) was cooled to 0-5° C. in an ice bath. Anhydrous DMF (141.6 g, 140.0 mL, 1938 mmol, 12.9 equiv) was added dropwise into the solution to form the corresponding Vilsmeier reagent. During addition of DMF, the internal temperature was controlled to below 10° C. The ice bath was removed and the reaction mixture was gradually warmed to ambient temperature over 40 minutes. Methyl-7H-pyrrolo[2,3-d]pyrimidine hydrochloride (Compound 1a hydrochloride 25.44 g, 150 mmol) was charged into the in-situ generated Vilsmeier reagent as a solid in one portion at ambient temperature and the resulting slurry was agitated at ambient temperature for 5-10 minutes to ensure complete mixing before being warmed to 85-90° C. The reaction mixture was agitated at 85-90° C. for one hour before being gradually cooled to ambient temperature. Anhydrous tetrahydrofuran (THF, 200 mL) was charged and the resulting slurry was agitated at ambient temperature for 48 hours followed by at 0-5° C. for 2 hours. The solids were collected by filtration, washed with a one to one mixture of THF and MTBE (2×200 mL), and dried under vacuum to constant weight to afford the desired product, (E)-N-(3-(Dimethylamino)-2-(7H-pyrrolo[2,3-d]pyrimidin-4-yl)allylidene)-N-methylmethanaminium chloride hydrochloride (Compound 2d), 46.17 g, 47.43 g theoretical, 99.5% by HPLC area %, 95.2 wt % by NMR, 92.7% yield), as a yellow to brown crystalline solid (Form II), which contained 2.3% of DMF and acetonitrile and 0.8% of water and was used in the subsequent reaction without further purification. For Compound 2d: $^1$H NMR (500 MHz, DMSO-$d_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-$d_6$, 125 MHz) δ 163.8, 151.3, 147.6, 145.0, 132.1, 117.5, 102.9, 91.6, 48.9, 42.1 ppm; $C_{13}H_{19}Cl_2N_5$ (MW, 279.77 for Compound 2c and 244.32 for Compound 2 without anion) LCMS (EI) mle 244.2 ($M^+$, base peak).

Crystalline Form II of Compound 2d was characterized by XRPD, DSC and TGA.

X-Ray Powder Diffraction (XRPD): The X-Ray Powder Diffraction (XRPD) was obtained from Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

Crystalline Form II of Compound 2d was confirmed to be crystalline solid according to XRPD analysis. The XRPD pattern of Compound 2d crystalline Form II is shown in in FIG. 4 and the peak data is given in Table 2.

TABLE 2

XRPD Peak Data for Compound 2d Form II

| 2-Theta (°) | Relative Intensity (%) |
|---|---|
| 7.3 | 7.3 |
| 11.1 | 0.9 |
| 11.5 | 49.6 |
| 11.9 | 17.0 |
| 13.3 | 29.2 |
| 14.6 | 3.3 |
| 15.5 | 27.3 |
| 15.8 | 26.5 |
| 16.1 | 13.1 |
| 16.4 | 1.5 |
| 17.4 | 32.8 |
| 17.9 | 8.1 |
| 18.2 | 6.4 |
| 19.1 | 19.5 |
| 19.4 | 16.2 |
| 19.6 | 14.9 |
| 20.7 | 5.3 |
| 21.4 | 40.8 |
| 22.0 | 35.6 |
| 22.4 | 10.8 |
| 22.6 | 26.2 |
| 23.2 | 71.6 |
| 23.8 | 4.9 |
| 24.0 | 8.0 |
| 24.9 | 70.7 |
| 25.5 | 100 |
| 26.0 | 1.7 |
| 26.4 | 0.9 |
| 26.7 | 21.1 |
| 27.0 | 15.3 |
| 27.4 | 4.6 |
| 27.9 | 12.6 |
| 29.1 | 23.1 |
| 29.5 | 4.2 |

Differential Scanning calorimetry (DSC): The DSC was obtained from TA Instruments Differential Scanning calorimetry, Discovery DSC2500 with autosampler. The DSC instrument conditions were as follows: 20-300° C. at 10° C./min; Tzero aluminum sample pan and lid; and nitrogen gas flow at 50 mL/min. DSC analysis of Compound 2d crystalline Form II revealed one endothermic peak with an onset temperature of 46.6° C. and a maximum at 99.2° C. The DSC thermogram of Compound 2d crystalline Form II is provided in in FIG. 5.

Thermogravimetric Analysis (TGA): The TGA was obtained from TA Instruments Thermogravimetric Analyzer, Discovery TGA5500 with autosampler. The general experimental conditions for TGA were: ramp from 25° C. to 300° C. at 10° C./min; nitrogen purge gas flow at 25 mL/min; platinum sample holder. TGA analysis of Compound 2d crystalline Form II revealed 4.7% weight loss below 150° C. to and significant weight loss above 175° C. due to decomposition. The TGA thermogram of Compound 2d crystalline Form II is provided in in FIG. 6.

Example 6: Alternative Preparation of (E)-N-(3-(Dimethylamino)-2-(7H-pyrrolo[2,3-d]pyrimidin-4-yl)allylidene)-N-methylmethanaminium chloride hydrochloride (2d)

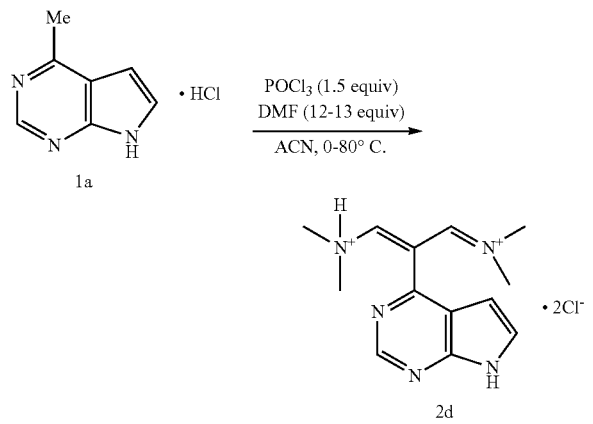

A solution of phosphorus oxochloride (POCl$_3$, 17.25 g, 10.5 mL, 112.5 mmol, 1.5 equiv) in anhydrous acetonitrile (65 mL) was cooled to 0-5° C. in an ice bath. Anhydrous DMF (70.8 g, 70.0 mL, 968 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature. Methyl-7H-pyrrolo[2,3-d]pyrimidine hydrochloride (Compound 1a hydrochloride, 12.72 g, 75.0 mmol) was charged into the in-situ generated Vilsmeier reagent as a solid in one portion at ambient temperature and the resulting slurry was agitated at ambient temperature for 5-10 minutes to ensure complete mixing before being warmed to 75-80° C. The reaction mixture was agitated at 75-80° C. for one hour before being gradually cooled to ambient temperature. Anhydrous tetrahydrofuran (THF, 100 mL) was charged and the resulting slurry was agitated at ambient temperature for two hours followed by at 0-5° C. for two hours. The solids were collected by filtration and washed with a one to one mixture of THF and MTBE (2×100 mL) to afford the desired product, (E)-N-(3-(Dimethylamino)-2-(7H-pyrrolo[2,3-d]pyrimidin-4-yl)allylidene)-N-methylmethanaminium chloride hydrochloride (Compound 2d, 27.83 g, 23.72 g theoretical, 96.1% by HPLC area %, 69.0 wt % by NMR, 81.0% yield), as a yellow to brown crystalline (Form I) solid, which contained 11.49% of DMF and acetonitrile and 1.38% of water and was used in the subsequent reaction without further purification. For Compound 2d: $^1$H NMR (500 MHz, DMSO-d$_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-d$_6$, 125 MHz) δ 163.8, 151.3, 147.6, 145.0, 132.1, 117.5, 102.9, 91.6, 48.9, 42.1 ppm; C$_{13}$H$_{19}$Cl$_2$N$_5$ (MW, 279.77 for Compound 2c and 244.32 for Compound 2 without anion) LCMS (EI) mle 244.2 (M$^+$, base peak).

Example 7: Preparation of (E)-N-(3-(Dimethylamino)-2-(7H-pyrrolo[2,3-d]pyrimidin-4-yl)allylidene)-N-methylmethanaminium chloride (Compound 2 chloride or Compound 2c) Using POCl$_3$

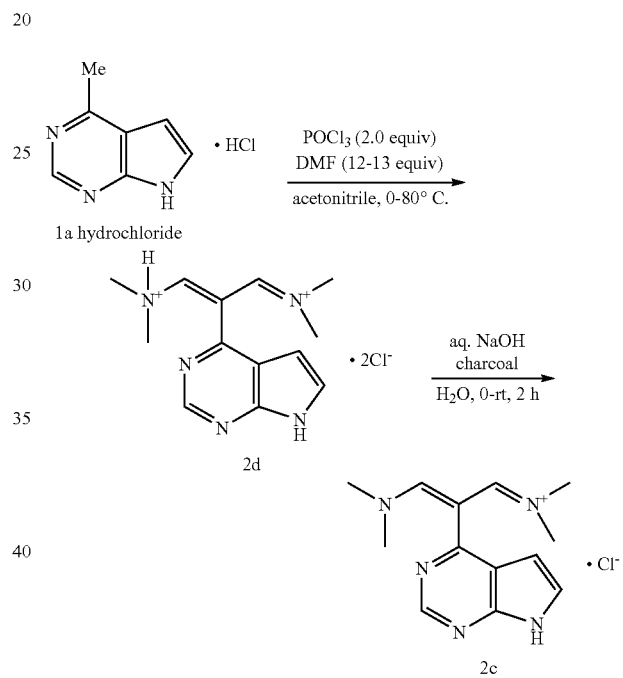

A solution of phosphorus oxochloride (POCl$_3$, 23.0 g, 14.0 mL, 150 mmol, 2.0 equiv) in anhydrous acetonitrile (65 mL) was cooled to 0-5° C. in an ice bath. Anhydrous DMF (70.8 g, 70.0 mL, 968 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature. Methyl-7H-pyrrolo[2,3-d]pyrimidine hydrochloride (Compound 1a hydrochloride, 12.72 g, 75.0 mmol) was charged into the in-situ generated Vilsmeier reagent as a solid in one portion at ambient temperature and the resulting slurry was agitated at ambient temperature for 5-10 minutes to ensure complete mixing before being warmed to 75-80° C. The reaction mixture was agitated at 75-80° C. for one hour before being gradually cooled to ambient temperature. Anhydrous tetrahydrofuran (100 mL) was charged and the resulting slurry was agitated at ambient temperature for two hours followed by at 0-5° C. for two hours. The solids were collected by filtration and washed with a one to one mixture of THF and MTBE (2×100 mL) to afford the desired product, (E)-N-(3-(Dimethylamino)-2-(7H-pyrrolo[2,3-d]pyrimidin-4-yl)allylidene)-N-methylmethanaminium chloride hydrochloride (Compound 2d), as a yellow to brown wet cake. The wet cake was then dissolved in water (120 mL), and the pH of the resulting aqueous solution was adjusted to 7-8 by treating with a 50% aqueous solution of sodium hydroxide (NaOH, 19.06 g) at 0-5° C. The neutralized aqueous solution was then treated with charcoal (5.5 g) and agitated at ambient temperature for 12 hours. The charcoal was removed by filtration through a Celite bed and the Celite bed was washed with water (50 mL). The resulting aqueous solution, which contained the desired product, (E)-N-(3-(Dimethylamino)-2-(7H-pyrrolo[2,3-d]pyrimidin-4-yl)allylidene)-N-methylmethanaminium chloride (Compound 2c, >99.0% pure by HPLC area %), was used for the subsequent reactions without further treatment.

Example 8: Synthesis of (E)-N-(3-(Dimethylamino)-2-(7H-pyrrolo[2,3-d]pyrimidin-4-yl)allylidene)-N-methylmethanaminium chloride (Compound 2c)

Using Triphosgene

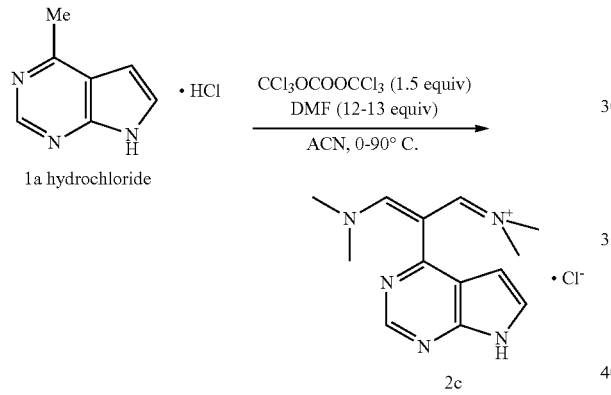

A solution of triphosgene ((CCl$_3$O)$_2$CO, 37.4 g, 126 mmol, 1.5 equiv) in anhydrous acetonitrile (73 mL) was cooled to 0-5° C. in an ice bath. Anhydrous DMF (79.0 g, 84 mL, 1083 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature over 40 minutes. Methyl-7H-pyrrolo[2,3-d]pyrimidine hydrochloride (Compound 1a hydrochloride, 14.25 g, 84.0 mmol) was charged into the in-situ generated Vilsmeier reagent as a solid in one portion at ambient temperature and the resulting slurry was agitated at ambient temperature for 5-10 minutes to ensure complete mixing before being warmed to 80-90° C. The reaction mixture was agitated at 80-90° C. for one hour before being gradually cooled to ambient temperature. Anhydrous tetrahydrofuran (THF, 112 mL) was charged and the resulting slurry was agitated at ambient temperature for 12 hours followed by at 0-5° C. for 2 hours. The solids were collected by filtration, washed with a one to one mixture of THF and MTBE (2×200 mL), and dried under vacuum to constant weight to afford the desired product, (E)-N-(3-(Dimethylamino)-2-(7H-pyrrolo[2,3-d]pyrimidin-4-yl)allylidene)-N-methylmethanaminium chloride (Compound 2c), 28.3 g, 23.5 g theoretical, 98.8% by HPLC area %, 64.9 wt % by HPLC, 78.2% yield), as a yellow to brown amorphous solid, which contained 19.7% of DMF and 0.8% of water and was used in the subsequent reaction without further purification. For Compound 2c: $^1$H NMR (500 MHz, DMSO-d$_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-d$_6$, 125 MHz) δ 163.8, 151.3, 147.6, 145.0, 132.1, 117.5, 102.9, 91.6, 48.9, 42.1 ppm; C$_{13}$H$_{19}$Cl$_2$N$_5$ (MW, 279.77 for Compound 2c and 244.32 for Compound 2 without anion) LCMS (D) m/e 244.2 (M$^+$, base peak).

Example 9: Preparation of (E)-N-(3-(dimethylamino)-2-(7H-pyrrolo[2,3-d]pyrimidin-4-yl)allylidene)-N-methylmethanaminium Salts

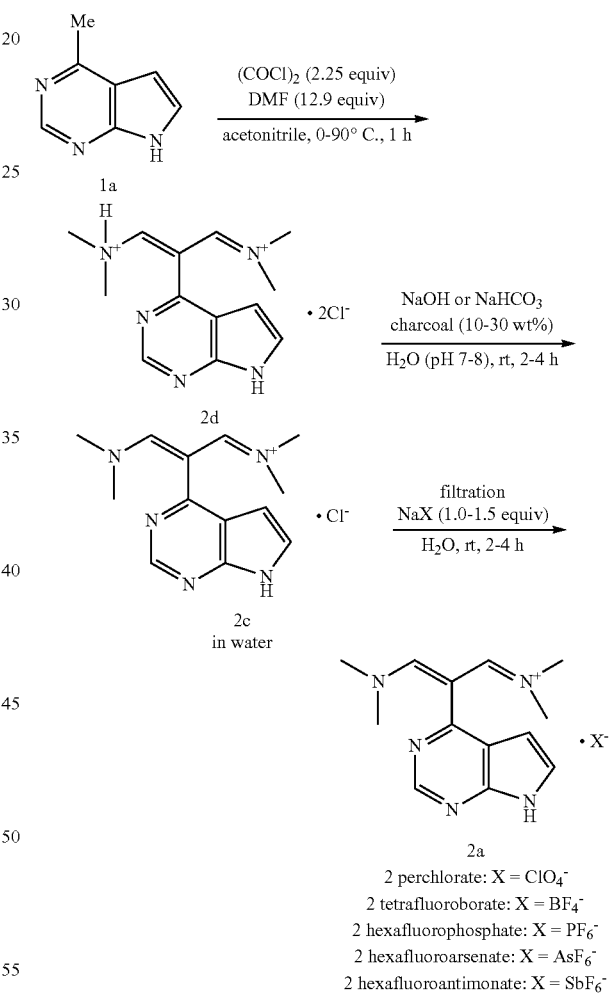

(E)-N-(3-(dimethylamino)-2-(7H-pyrrolo[2,3-c]pyrimidin-4-yl)allylidene)-N-methylmethanaminium perchlorate (Compound 2 perchlorate)

To a solution of (E)-N-(3-(dimethylamino)-2-(7H-pyrrolo[2,3-d]pyrimidin-4-yl)allylidene)-N-methylmethanaminium chloride (Compound 2c, 2.94 g, 10.525 mmol) in water (8.06 mL) was added sodium perchlorate (NaClO$_4$, 1.933 g, 15.79 mmol, 1.50 equiv) at ambient temperature. After stirred at 20-25° C. for 12 hour, the slurry was cooled in an ice bath for 2 hours. The solids was filtered, washed with cold $H_2O$ (3×2 mL) and dried under vacuum to afford the crude desired product, (E)-N-(3-(dimethylamino)-2-(7H-pyrrolo[2,3-d]pyrimidin-4-yl)allylidene)-N-methylmethanaminium perchlorate (Compound 2 perchlorate), as white solids, which were used in the subsequent reaction without further purification. $^1$H NMR (400 MHz, DMSO-$d_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; $C_{13}H_{18}ClN_5O_4$(MW, 343.77 for Compound 2 perchlorate and 244.32 for Compound 2 without anion) LCMS (EI) m/e 244.2 (M$^+$, base peak).

(E)-N-(3-(dimethylamino)-2-(7H-pyrrolo[2,3-c]pyrimidin-4-yl)allylidene)-N-methylmethanaminium tetrafluoroborate (Compound 2 tetrafluoroborate)

To a solution of (E)-N-(3-(dimethylamino)-2-(7H-pyrrolo[2,3-d]pyrimidin-4-yl)allylidene)-N-methylmethanaminium chloride (Compound 2c, 2.94 g, 10.525 mmol) in water (8.06 mL) was added sodium tetrafluoroborate ($NaBF_4$, 1.733 g, 15.79 mmol, 1.50 equiv) at ambient temperature. After stirring at 20-25° C. for 12 hours, the slurry was cooled in an ice bath for 2 hours. The solids was filtered, washed with cold $H_2O$ (3×2 mL) and dried under vacuum to afford the crude desired product, (E)-N-(3-(dimethylamino)-2-(7H-pyrrolo[2,3-d]pyrimidin-4-yl)allylidene-N-methylmethanaminium tertafluoroborate (Compound 2 tetrafluoroborate, 1.80 g, 3.49 g theoretical, 51.6% yield), as a white solid, which was used in the subsequent reaction without further purification. $^1$H NMR (400 MHz, DMSO-$d_6$) δ 12.39-12.34 (s, 1H), 8.85-8.80 (s, 1H), 7.99-7.94 (s, 2H), 7.71-7.65 (dd, J=3.4, 2.2 Hz, 1H), 6.52-6.46 (dd, J=3.5, 1.7 Hz, 1H), 3.34-3.29 (s, 6H), 2.38-2.33 (s, 6H) ppm; $^{11}$B NMR (DMSO-$d_6$, 128 MHz) δ-1.27 ppm; $^{19}$F NMR (DMSO-$d_6$, 376.5 MHz) δ-148.23 and -148.28 ppm; $C_{13}H_{18}BF_4N_5$ (MW, 331.13 for Compound 2 tetrafluoroborate and 244.32 for Compound 2 without anion) LCMS (EI) m/e 244.2 (M$^+$, base peak).

(E)-N-(3-(dimethylamino)-2-(7H-pyrrolo[2,3-d]pyrimidin-4-yl)allylidene)-N-methylmethanaminium hexafluorophosphate (Compound 2 hexafluorophosphate)

To a solution of crude (E)-N-(3-(dimethylamino)-2-(7H-pyrrolo[2,3-d]pyrimidin-4-yl)allylidene)-N-methylmethanaminium chloride hydrochloride (Compound 2d, 25.61 g, 91.6 mmol) in water (80 mL), generated from 4-methyl-7H-pyrrolo[2,3-d]pyrimidine (12.19 g, 91.6 mmol) via the corresponding Vilsmeier reaction as described in Example 4, was added an aqueous solution of sodium hydroxide (NaOH) at 0-5° C. to adjust the solution pH to 7-8. The resulting aqueous solution was added charcoal (7.69 g) and the mixture was agitated at ambient temperature for 2-4 hours. Charcoal was removed by filtration through a Celite bed and the wet charcoal cake was washed with water (15 mL). The combined aqueous solution was then added sodium hexafluorophosphate ($NaPF_6$, 20.08 g, 120 mmol, 1.31 equiv) at ambient temperature. After stirring at 20-25° C. for 1 hour, the slurry was cooled in an ice bath for 30 minutes. The solids was filtered, washed with cold $H_2O$ (2×25 mL) and dried under vacuum to afford the crude desired product, (E)-N-(3-(dimethylamino)-2-(7H-pyrrolo[2,3-d]pyrimidin-4-yl)allylidene)-N-methylmethanaminium hexafluorophosphate (Compound 2 hexafluorophosphate, 24.30 g, 35.81 g theoretical, 67.9% yield, 98.7% by HPLC area %), as white crystalline solids, which were used in the subsequent reaction without further purification. The crude Compound 2 hexafluorophosphate can be purified by recrystallization from water to generate pure product as white crystalline solids. For Compound 2 hexafluorophosphate: $^1$HNMR (500 MHz, DMSO-$d_6$) δ 12.36 (s, 1H), 8.83 (s, 1H), 7.97 (br s, 2H), 7.68 (dd, J=3.2, 2.6 Hz, 1H), 6.48 (dd, J=3.4, 1.8 Hz, 1H), 3.32 (s, 6H), 2.36 (br s, 6H) ppm; $^{13}$C NMR (125 MHz, DMSO-$d_6$) δ 163.7, 152.9, 151.4, 151.0, 128.9, 120.7, 101.5, 99.8, 48.9, 40.0 ppm; $^{19}$F NMR (DMSO-$d_6$, 470.6 MHz) δ-70.2 (d, $^1$J(PF)=711.1 Hz) ppm; $^{31}$PNMR (DMSO-$d_6$, 162 MHz) δ-144.19 (septet, $^1$J(PF)=711 Hz) ppm. $C_{13}H_{18}F_6N_5P$ (MW, 389.29 for Compound 2 hexafluorophosphate and 244.32 for Compound 2 without anion) LCMS (EI) mle 244.2 (M$^+$, base peak). The crystallinity of Compound 2 hexafluorophosphate was characterized by XRPD, DSC and TGA.

Figure 7:
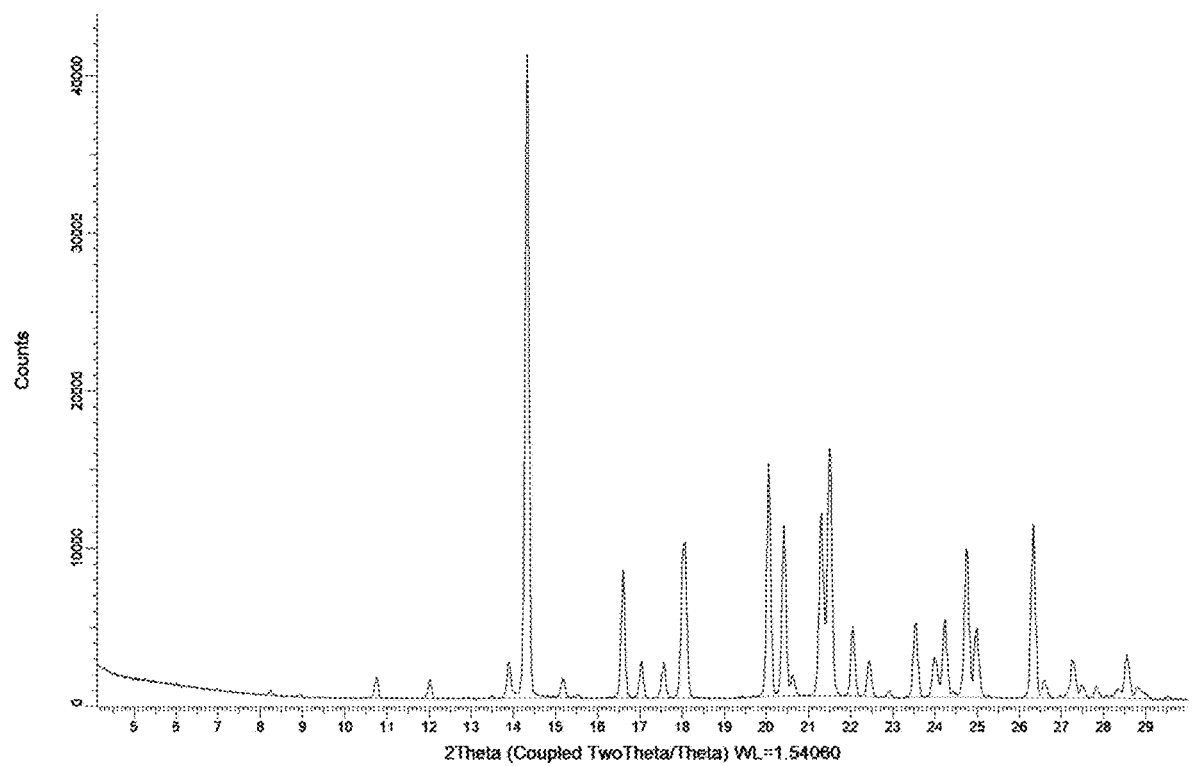
FIG. 7 is an XRPD pattern of Compound 2 hexafluorophosphate.

X-Ray Powder Diffraction (XRPD): The X-Ray Powder Diffraction (XRPD) was obtained from Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min. Compound 2 hexafluorophosphate was confirmed to be crystalline solid according to XRPD analysis. The XRPD pattern of Compound 2 hexafluorophosphate is shown in in FIG. 7 and the peak data is given in Table 3.

TABLE 3

XRPD Peak Data for Compound 2 hexafluorophosphate

| 2-Theta (°) | Relative Intensity (%) |
|---|---|
| 8.2 | 0.7 |
| 8.9 | 0.4 |
| 10.8 | 3.2 |
| 12.0 | 2.9 |
| 12.9 | 0.3 |
| 13.5 | 0.3 |
| 13.9 | 5.5 |
| 14.3 | 100 |
| 15.2 | 3.0 |
| 15.5 | 0.5 |
| 16.6 | 19.9 |
| 17.0 | 5.7 |
| 17.6 | 5.4 |
| 18.1 | 24.1 |
| 19.4 | 0.2 |
| 20.1 | 36.3 |
| 20.4 | 26.7 |
| 20.6 | 3.3 |
| 21.3 | 28.2 |
| 21.5 | 38.7 |
| 22.1 | 10.7 |
| 22.4 | 5.6 |
| 22.9 | 1.1 |
| 23.5 | 11.5 |
| 24.0 | 6.1 |
| 24.2 | 12.3 |
| 24.7 | 23.1 |
| 25.0 | 10.7 |
| 26.3 | 26.8 |
| 26.6 | 2.6 |
| 26.9 | 0.3 |
| 27.3 | 5.8 |
| 27.5 | 1.9 |

TABLE 3-continued

XRPD Peak Data for Compound 2 hexafluorophosphate

| 2-Theta (°) | Relative Intensity (%) |
|---|---|
| 27.8 | 1.7 |
| 28.1 | 0.3 |
| 28.3 | 1.5 |
| 28.6 | 6.7 |
| 28.8 | 1.8 |
| 29.0 | 0.9 |
| 29.5 | 0.4 |

Figure 8:
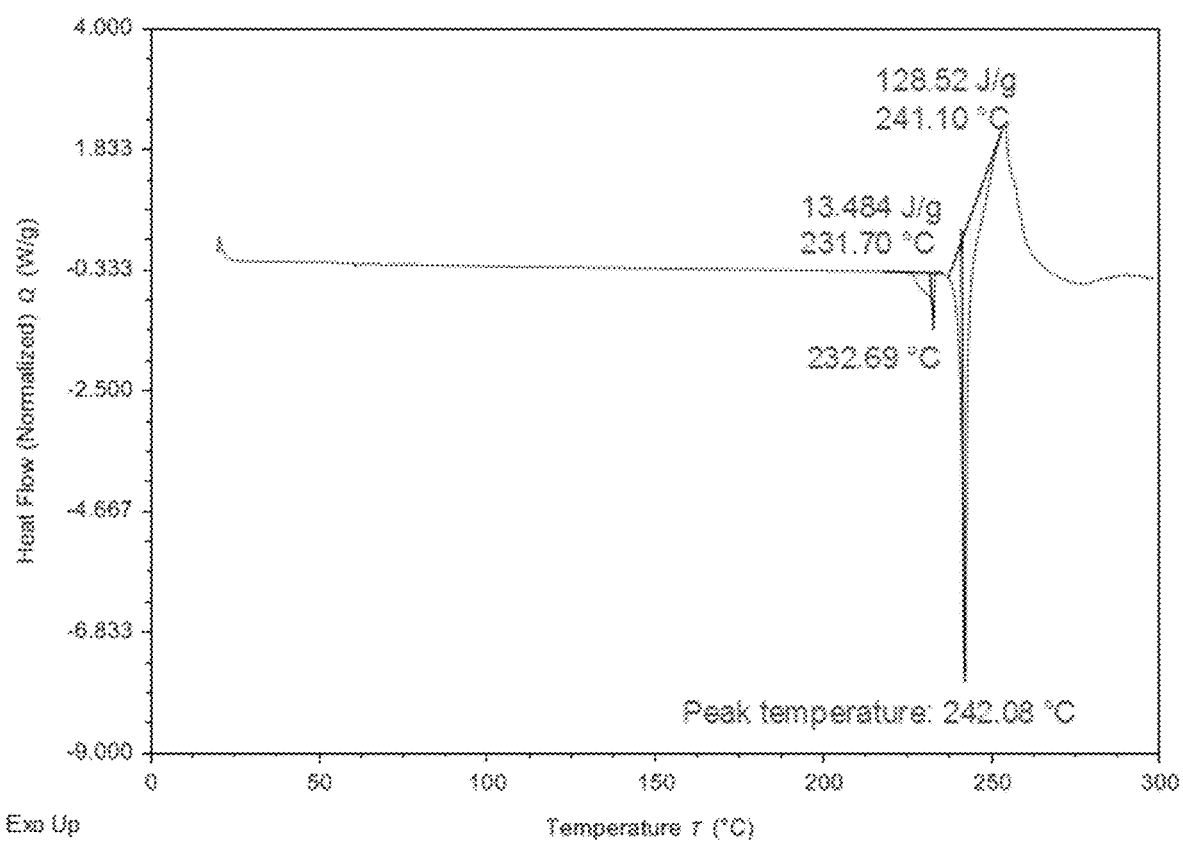
FIG. 8 is a DSC thermogram of Compound 2 hexafluorophosphate.

Differential Scanning calorimetry (DSC): The DSC was obtained from TA Instruments Differential Scanning calorimetry, Discovery DSC2500 with autosampler. The DSC instrument conditions were as follows: 20-300° C. at 10° C./min; Tzero aluminum sample pan and lid; and nitrogen gas flow at 50 mL/min. DSC analysis of Compound 2 hexafluorophosphate crystalline sample revealed one endothermic peak with an onset temperature of 231.7° C. and a maximum at 232.7° C. due to melting and second endothermic peak with an onset temperature of 241.1° C. and a maximum at 242.1° C. due to decomposition. The DSC thermogram of Compound 2 hexafluorophosphate is provided in in FIG. 8.

Figure 9:
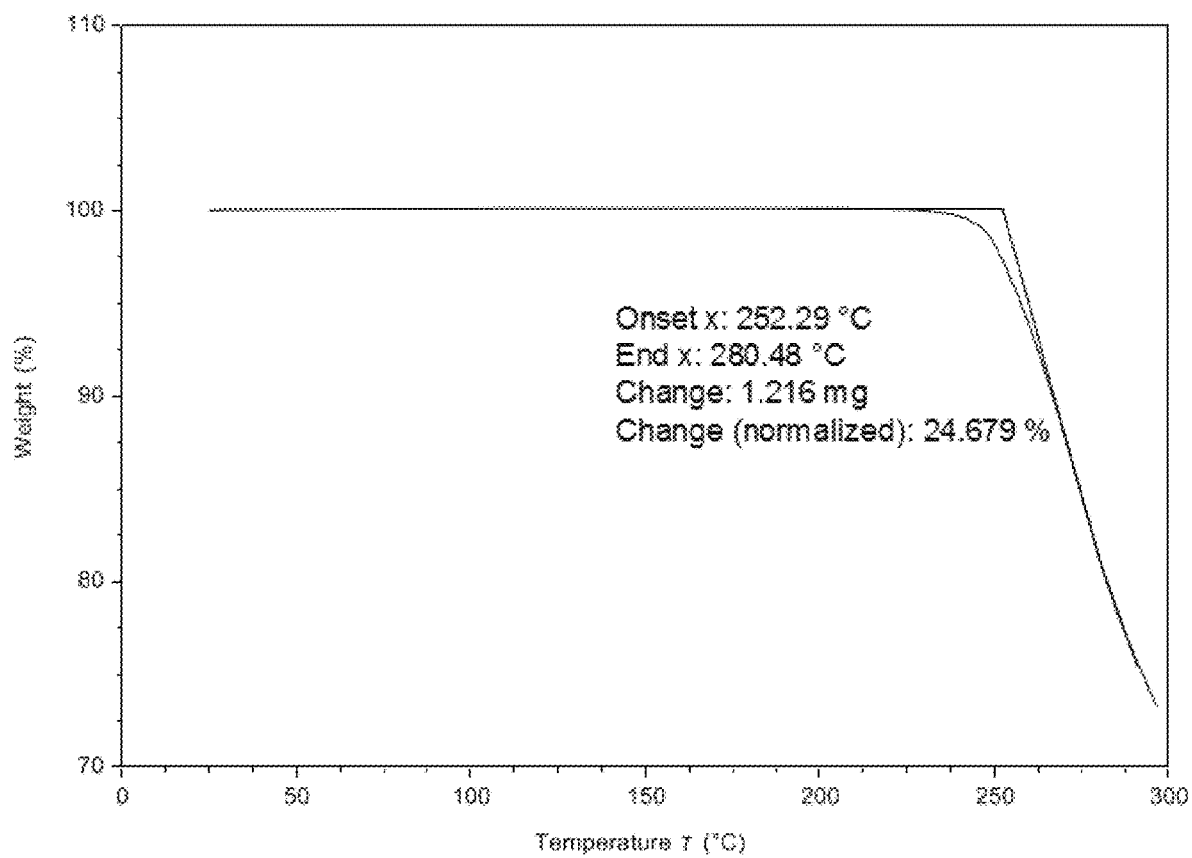
FIG. 9 is a TGA thermogram Compound 2 hexafluorophosphate.

Thermogravimetric Analysis (TGA): The TGA was obtained from TA Instruments Thermogravimetric Analyzer, Discovery TGA5500 with autosampler. The general experimental conditions for TGA were: ramp from 25° C. to 300° C. at 10° C./min; nitrogen purge gas flow at 25 mL/min; platinum sample holder. TGA analysis of Compound 2 hexafluorophosphate crystalline sample revealed significant weight loss above 250° C. due to decomposition. The TGA thermogram of Compound 2 hexafluorophosphate is provided in in FIG. 9.

(E)-N-(3-(dimethylamino)-2-(7H-pyrrolo[2,3-d]pyrimidin-4-yl)allylidene)-N-methylmethanaminium hexafluoroarsenate (Compound 2 hexafluoroarsenate)

To a solution of (E)-N-(3-(dimethylamino)-2-(7H-pyrrolo[2,3-d]pyrimidin-4-yl)allylidene)-N-methylmethanaminium chloride (Compound 2c, 2.94 g, 10.525 mmol) in water (8.06 mL) was added sodium hexafluoroarsenate (NaAsF$_6$, 3.35 g, 15.79 mmol, 1.50 equiv) at ambient temperature. After stirred at 20-25° C. for 12 hour, the slurry was cooled in an ice bath for 2 hours. The solids was filtered, washed with cold H$_2$O (3×2 mL) and dried under vacuum to afford the crude desired product, (E)-N-(3-(dimethylamino)-2-(7H-pyrrolo[2,3-d]pyrimidin-4-yl)allylidene)-N-methylmethanaminium hexafluoroarsenate (Compound 2 hexafluoroarsenate, 4.51 g, 4.56 g theoretical, 99% yield), as white solids, which were used in the subsequent reaction without further purification. For Compound 2 hexafluoroarsenate: $^1$H NMR (400 MHz, DMSO-d$_6$) δ 12.38 (s, 1H), 8.83 (s, 1H), 7.97 (s, 2H), 7.76-7.57 (t, J=2.9 Hz, 1H), 6.59-6.36 (dd, J=3.2, 1.8 Hz, 1H), 3.32 (s, 6H), 2.35 (s, 6H) ppm; $^{19}$F NMR (DMSO-d$_6$, 376.5 MHz) δ-62.16 (quartet, $^1$J(AsF)=937.5 Hz) ppm; C$_{13}$H$_{18}$F$_6$N$_5$As (MW, 433.23 for Compound 2 hexafluoroarsenate and 244.32 for Compound 2 without anion) LCMS (EI) m/e 244.2 (M$^+$, base peak).

(E)-N-(3-(dimethylamino)-2-(7H-pyrrolo[2,3-d]pyrimidin-4-yl)allylidene)-N-methylmethanaminium hexafluoroantimonate (Compound 2 hexafluoroantimonate)

To a solution of (E)-N-(3-(dimethylamino)-2-(7H-pyrrolo[2,3-d]pyrimidin-4-yl)allylidene)-N-methylmethanaminium chloride (Compound 2c, 2.94 g, 10.525 mmol) in water (8.06 mL) was added sodium hexafluoroantimonate (NaSbF$_6$, 4.08 g, 15.79 mmol, 1.50 equiv) at ambient temperature. After stirred at 20-25° C. for 12 hour, the slurry was cooled in an ice bath for 2 hours. The solids was filtered, washed with cold H$_2$O (3×2 mL) and dried under vacuum to afford the crude desired product, (E)-N-(3-(dimethylamino)-2-(7H-pyrrolo[2,3-d]pyrimidin-4-yl)allylidene)-N-methylmethanaminium hexafluoroantimonate (Compound 2 hexafluoroantimonate, 2.61 g, 5.05 g theoretical, 51.7% yield), as white solids, which were used in the subsequent reaction without further purification. For Compound 2 hexafluoroantimonate: $^1$H NMR (400 MHz, DMSO-d$_6$) δ 12.37 (s, 1H), 8.83 (s, 1H), 7.98 (s, 2H), 7.68 (s, 1H), 6.49 (s, 1H), 3.32 (s, 6H), 2.35 (s, 6H) ppm; $^{19}$F NMR (DMSO-d$_6$, 376.5 MHz) δ-166.86 ppm; C$_{13}$H$_{18}$F$_6$N$_5$Sb (MW, 480.07 for Compound 2 hexafluoroantimonate and 244.32 for Compound 2 without anion) LCMS (EI) m/e 244.2 (M$^+$, base peak).

Example 10: Alternative Preparation of (E)-N-(3-(dimethylamino)-2-(7H-pyrrolo[2,3-d]pyrimidin-4-yl)allylidene)-N-methylmethanaminium perchlorate (Compound 2 perchlorate)

Method 1

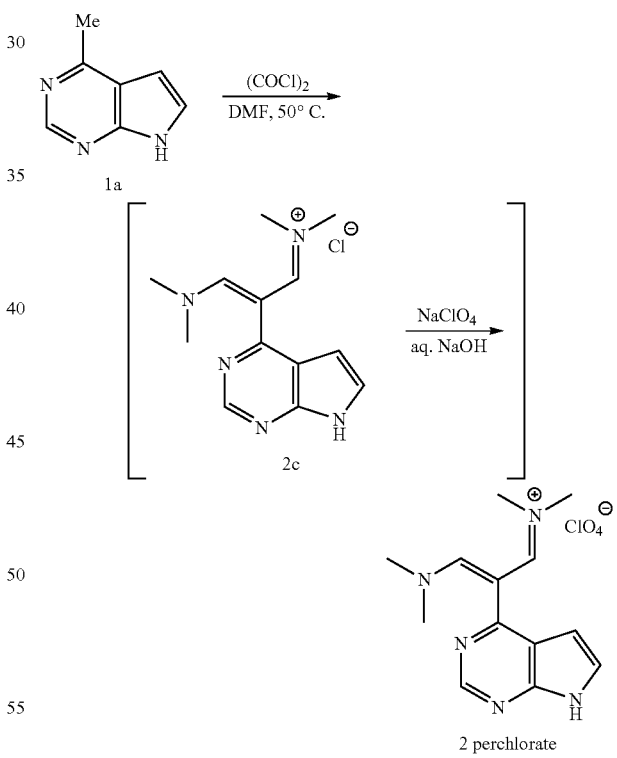

Oxalyl chloride (20.0 mL, 228 mmol, 3.04 equiv) was slowly charged to DMF (107 mL, 1378 mmol, 18.4 equiv) over 15 minutes while keeping the internal temperature at below 50° C. After addition, the resulting slurry was cooled to ambient temperature and stirred at ambient temperature for 2 hours. 4-Methyl-7H-pyrrolo[2,3-d]pyrimidine (Compound 1a, 10.0 g, 75 mmol) was added to the slurry at ambient temperature and the resulting reaction mixture was stirred at ambient temperature for 16 hours and then at 50°

C. for 5.5 hours. The reaction mixture was cooled to ambient temperature and quenched with ice (60 g). The quenched reaction mixture was concentrated under vacuum to a residue, which was then dissolved in water (50 mL). Sodium perchlorate (NaClO$_4$, 20.23 g, 165 mmol, 2.2 equiv) was then added to the aqueous solution at ambient temperature. The resulting mixture was cooled in an ice bath before sodium hydroxide (NaOH, 7.5 g, 188 mmol, 2.5 equiv) was added slowly. The solids were collected by filtration, washed with water (30 mL), and dried under vacuum to give the crude desired product, (E)-N-(3-(dimethylamino)-2-(7H-pyrrolo[2,3-d]pyrimidin-4-yl)allylidene)-N-methylmethanaminium perchlorate (Compound 2 perchlorate, 18.7 g, 25.78 g theoretical, 72.5% yield), as grey solids, which were used for the subsequent reaction without further purification. $^1$H NMR (400 MHz, DMSO-d$_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; C$_{13}$H$_{18}$ClN$_5$O$_4$(MW, 343.77 for Compound 2 perchlorate and 244.32 for Compound 2 without anion) LCMS (D) m/e 244.2 (M$^+$, base peak).

Method 2

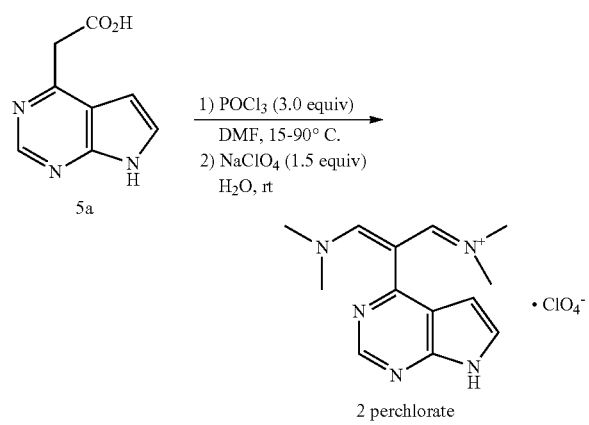

To a solution of 2-(7H-pyrrolo[2,3-d]pyrimidin-4-yl)acetic acid (Compound 5a, 354 mg, 2.0 mmol) in anhydrous DMF (2.92 g, 3.1 mL, 40 mmol, 20 equiv) was added phosphorus oxychloride (POCl$_3$, 920 mg, 0.56 mL, 6.0 mmol, 3.0 equiv) at ambient temperature. The resulting reaction mixture was then warmed to 80-90° C. and agitated at 80-90° C. for 30 minutes. When the reaction was complete, the reaction mixture was cooled down to ambient temperature. The cooled reaction mixture was quenched by pouring into ice (10 g). The solution was then concentrated under reduced pressure and the resulting residue was treated with water (3 mL). The aqueous solution was neutralized with an aqueous solution of NaOH to pH 7-8 before being treated with activated charcoal (50 mg). The mixture was agitated at ambient temperature for 30 minutes before being filtered through a Celite bed. The Celite bed was washed with water (2 mL). The combined filtrate and the wash solution was then treated with solid sodium perchlorate (NaClO$_4$, 367 mg, 3.0 mmol, 1.5 equiv) at ambient temperature. The mixture was stirred at ambient temperature for 1 hour followed by at 0-5° C. for 1 hour. The solids were then collected by filtration, washed with water (2×2 mL), dried under vacuum to give the crude desired product, (E)-N-(3-(dimethylamino)-2-(7H-pyrrolo[2,3-d]pyrimidin-4-yl)allylidene)-N-methylmethanaminium perchlorate (Compound 2 perchlorate), 330 mg, 688 mg theoretical, 48% yield), as grey solids, which were used for the subsequent reaction without further purification. For Compound 2 perchlorate: $^1$H NMR (400 MHz, DMSO-d$_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; C$_{13}$H$_{18}$ClN$_5$O$_4$ (MW, 343.77 for Compound 2 perchlorate and 244.32 for Compound 2 without anion) LCMS (D) m/e 244.2 (M$^+$, base peak).

Method 3

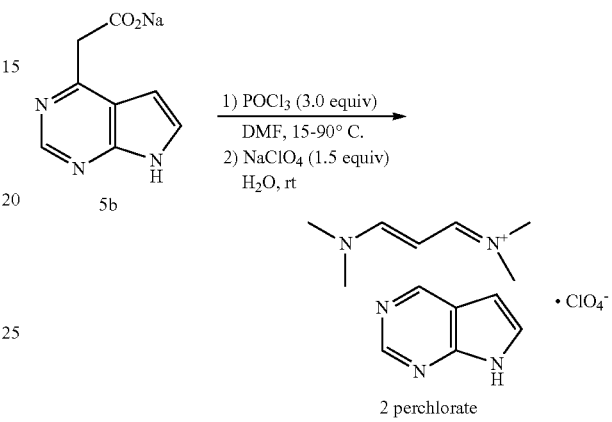

To a solution of sodium 2-(7H-pyrrolo[2,3-d]pyrimidin-4-yl)acetate (Compound 5b, 1.70 g, 8.54 mmol) in anhydrous DMF (12.48 g, 13.2 mL, 171 mmol, 20 equiv) was added phosphorus oxychloride (POCl$_3$, 3.93 g, 2.4 mL, 25.6 mmol, 3.0 equiv) at ambient temperature. The resulting reaction mixture was then warmed to 80-90° C. and agitated at 80-90° C. for 30 minutes. When the reaction was complete, the reaction mixture was cooled down to ambient temperature. The cooled reaction mixture was quenched by pouring into ice (40 g). The solution was then concentrated under reduced pressure and the resulting residue was treated with water (10 mL). The aqueous solution was neutralized with an aqueous solution of NaOH to pH 7-8 before being treated with activated charcoal (200 mg). The mixture was agitated at ambient temperature for 30 minutes before being filtered through a Celite bed. The Celite bed was washed with water (5 mL). The combined filtrate and the wash solution was then treated with solid sodium perchlorate (NaClO$_4$, 1.57 g, 12.8 mmol, 1.5 equiv) at ambient temperature. The mixture was stirred at ambient temperature for 1 hour followed by at 0-5° C. for 1 hour. The solids were then collected by filtration, washed with water (2×5 mL), dried under vacuum to give the desired product, (E)-N-(3-(dimethylamino)-2-(7H-pyrrolo[2,3-d]pyrimidin-4-yl)allylidene)-N-methylmethanaminium perchlorate (Compound 2 perchlorate, 1.3 g, 2.94 g theoretical, 44.3% yield), as off-white solids, which were used for the subsequent reaction without further purification. $^1$H NMR (400 MHz, DMSO-d$_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; C$_{13}$H$_{18}$ClN$_5$O$_4$(MW, 343.77 for Compound 2 perchlorate and 244.32 for Compound 2 without an anion) LCMS (EI) m/e 244.2 (M$^+$, base peak).

Example 11: Preparation of 2-(7H-Pyrrolo[2,3-d]pyrimidin-4-yl)malonaldehyde ((E)-3-hydroxy-2-(7H-pyrrolo[2,3-d]pyrimidin-4-yl)acrylaldehyde (Compound 2b)

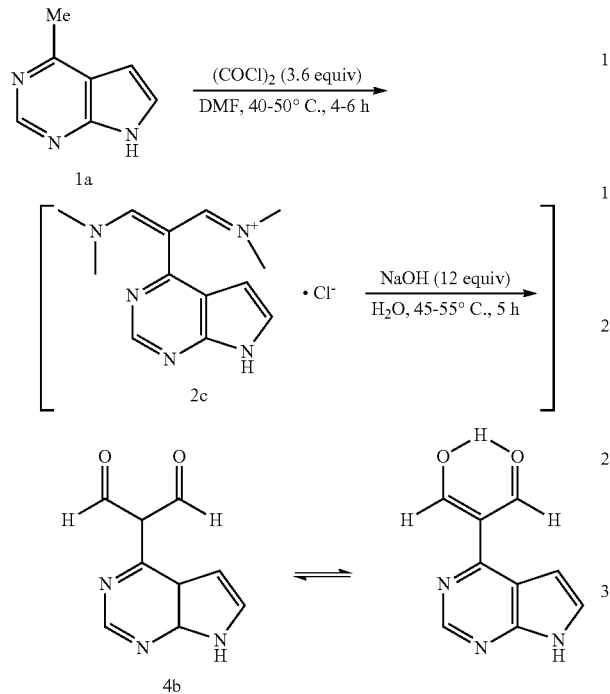

Oxalyl chloride (12.00 ml, 137 mmol, 3.64 equiv) was added dropwise to DMF (50 mL, 646 mmol, 17.18 equiv) while keeping the internal temperature at below 50° C. The resulting mixture was stirred at ambient temperature for 30 minutes. 4-Methyl-7H-pyrrolo[2,3-d]pyrimidine (Compound 1a, 5.00 g, 37.6 mmol) was added as a solid in one portion and the resulting reaction mixture was stirred at room temperature for 3 days and 50° C. for 4 hours. Once the reaction was complete, the reaction mixture was cooled to room temperature and quenched with ice (30 g). Sodium hydroxide (NaOH, 16.1 g, 403 mmol, 10.72 equiv) was added to the quenched reaction mixture and the mixture was stirred at room temperature for 26 hours. Additional sodium hydroxide (NaOH, 2.2 g, 55.0 mmol, 1.46 equiv) was added and the mixture was stirred at 40° C. for 4 hours. Once the hydrolysis reaction was complete, the mixture was cooled to 0-5° C. in an ice batch before the concentrated HCl solution was added to adjust pH to 5-6. The mixture was gradually warmed to ambient temperature and agitated at ambient temperature for 2 hours. Solids were collected by filtration, washed with cold water, and dried under vacuum to give the crude desired product, 2-(7H-pyrrolo[2,3-d]pyrimidin-4-yl)malonaldehyde ((E)-3-hydroxy-2-(7H-pyrrolo[2,3-d]pyrimidin-4-yl)acrylaldehyde, (Compound 2b, 6.33 g, 7.113 g theoretical, 89% yield), as a grey powder, which was used directly in the subsequent reaction without further purification. For Compound 2b: $^1$H NMR (400 MHz, DMSO-$d_6$) δ 13.74 (br s, 2H), 9.52 (s, 2H), 8.73 (s, 1H), 7.53 (dd, J=3.4, 2.3 Hz, 1H), 7.46 (dd, J=3.5, 1.7 Hz, 1H) ppm; $C_9H_7N_3O_2$ (MW, 189.17) LCMS (EI) mle 190.1 (M$^+$, base peak).

Example 12: Preparation of 4-Chloro-7H-pyrrolo[2,3-d]pyrimidine (Compound 12a)

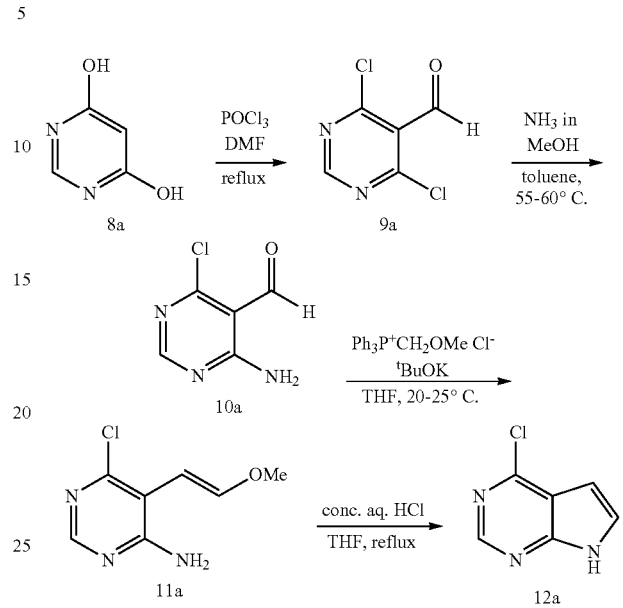

Step 1. 4,6-Dichloropyrimidine-5-carbaldehyde (Compound 9a)

In a 5 L 4-neck flask equipped with a mechanical stirrer, an addition funnel, a condenser, a thermocouple, and a $N_2$ sweep into an aqueous NaOH scrubbing solution, phosphorous oxychloride (POCl$_3$, 1 L, 10.572 mol, 4.82 equiv) was charged and cooled in an ice/salt bath. N,N-Dimethylformamide (DMF, 320 mL, 4.138 mol, 1.85 equiv) was then added dropwise to the flask at 0±2° C. After addition of approximately 100 mL of DMF over approximately 0.5 h, crystallization occurred and the reaction temperature was increased from 0 to 10° C. Addition was stopped and the mixture was allowed to re-cool to approximately 2° C. The remaining DMF was added over 2.5 h at below 8° C. The suspension became very thick making stirring difficult. When addition of DMF was complete, the mixture was stirred at 3-5° C. for 0.5 h. 4,6-dihydroxypyrimidine (Compound 8a, 250 g, 2.232 mol) was added portion wise as a solid. After about one third of 4,6-dihydroxypyrimidine was added, the reaction mixture became more mobile and a slow exothermic phenomena occurred with the reaction temperature increasing to approximately 12° C. over 0.5 h. The remaining 4,6-dihydroxypyrimidine was added portion wise over 0.25 h with the reaction temperature increasing from 12 to 27° C. The reaction temperature was maintained at 25-27° C. with intermittent cooling during which time the yellow suspension became thinner, then thicker once again. After the exothermic phenomenon subsided in about 1 h, the reaction mixture was heated slowly. At about 55° C. the reaction mixture became extremely thick and the second mild exothermic phenomenon was occurred. The heating mantle was removed while the reaction temperature continued to increase to about 63° C. and remained at this temperature for several minutes before dropping. Heating of the mixture was resumed until gentle reflux (about 100° C.) was attained. At about 95° C. a steady, fairly rapid evolution of HCl gas began and the reaction mixture gradually thinned and darkened. After about 0.5 h, a clear brown solution developed with the reflux temperature slowly increasing to 115° C. over 1.25 h. After a total of 2.5 h at reflux, the reaction mixture was cooled to ambient temperature and stirred overnight at ambient temperature. Excess amount of $POCl_3$ (as much as possible) was removed under reduced pressure (bath temperature 45-50° C.). The thick residual brown oil was poured very slowly into cold $H_2O$ (5 L) in a 20 L separation funnel, adding ice as needed to maintain the aqueous mixture near room temperature. The aqueous mixture was extracted with EtOAc (2×3 L followed by 1×2 L). The combined EtOAc extracts were washed with $H_2O$ (2×2.5 L), saturated $NaHCO_3$ aqueous solution (1 L), brine (1 L), dried over $Na_2SO_4$, filtered, and concentrated under reduced pressure (bath temperature at 35° C.) to afford the crude 4,6-dichloropyrimidine-5-carbaldehyde (Compound 9a, 270 g, 395 g theoretical, 68.4%) as yellow-orange solids. A 20 g portion of this crude material was purified by Kugelrohr distillation (oven temperature at 90-100° C., 225 mTorr) to give 15.3 g of pure 4,6-dichloropyrimidine-5-carbaldehyde (Compound 9a) as white solids that turned yellow on standing at room temperature. For 4,6-Dichloropyrimidine-5-carbaldehyde: $^1H$ NMR (300 MHz, $CDCl_3$) δ 10.46 (s, 1H), 8.89 (s, 1H) ppm.

Step 2.
4-Amino-6-chloropyrimidine-5-carbaldehyde
(Compound 10a)

A solution of 7 M $NH_3$ in MeOH (265 mL, 1.855 mol, 2.0 equiv) was added over 1.25 h to a solution of 4,6-dichloropyrimidine-5-carbaldehyde (Compound 9a, 163.7 g, 0.9301 mol) in toluene (3 L) at ambient temperature. The reaction temperature slowly increased from 20 to 26° C. and a yellow suspension formed. Mild cooling was applied to maintain the reaction temperature at below 26° C. The suspension was stirred at ambient temperature for 3.5 h before the solids were collected by filtration. The solids were washed with EtOAc (1 L). The filtrate was concentrated under reduced pressure, and the solids were triturated with toluene and n-heptane (2:1 v/v, 600 mL), filtered and dried to give 71.1 g of 4-amino-6-chloropyrimidine-5-carbaldehyde as a yellow solid. The original solid filtered from the reaction mixture contained additional amount of 4-amino-6-chloropyrimidine-5-carbaldehyde. The product was extracted from the filtered solid by stirring in EtOAc (1.25 L) for 1.5 h, filtering, then stirring in THF (750 mL) for 1 h and filtering. Both EtOAc and THF filtrates were concentrated under reduced pressure, and the resulting solids were triturated with toluene and n-heptane (2:1 v/v, 450 mL), filtered and dried to give an additional 44.1 g of 4-amino-6-chloropyrimidine-5-carbaldehyde as yellow solids. The combined yield of 4-amino-6-chloropyrimidine-5-carbaldehyde (115.2 g, 146.5 g theoretical) was 78.6%. For 4-Amino-6-chloropyrimidine-5-carbaldehyde: $^1HNMR$ (300 MHz, DMSO-$d_6$) δ 10.23 (s, 1H), 8.71 (bs, 1H), 8.55 (bs, 1H), 8.39 (s, 1H) ppm; $C_5H_4ClN_3O$ (MW, 157.56), LCMS (D) m/e 158 ($M^++H$).

Step 3.
6-Chloro-5-(2-methoxyvinyl)pyrimidin-4-ylamine
(Compound 11a)

A suspension of (methoxymethyl)triphenylphosphonium chloride (276.0 g, 0.807 mol, 1.1 equiv) in THF (1.5 L) was cooled in an ice/salt bath to −2° C. and 1 M potassium tert-butoxide (KO$^t$Bu) in THF (807 mL, 0.807 mol, 1.1 equiv) was added over 1.5 hour at −2 to −3° C. The deep red-orange mixture was stirred at −2 to −3° C. for 1 h. 4-Amino-6-chloropyrimidine-5-carbaldehyde (Compound 10a, 115.2 g, 0.7338 mol, 1.0 equiv) was then added portion wise to the reaction mixture as a solid form using THF (200 mL) to rinse the container and funnel. During the addition the reaction temperature increased from −3 to 13° C. and a brown color developed. When the reaction temperature dropped to 10° C., the cooling bath was removed and the reaction mixture was allowed to warm to ambient temperature and stirred at ambient temperature for 42 h. The reaction mixture was cooled to −2° C. before being quenched by the slow addition of saturated $NH_4Cl$ aqueous solution (750 mL). The mixture was concentrated under reduced pressure to remove most of the THF. The residue was partitioned between EtOAc (3 L) and $H_2O$ (1 L). The organic phase was filtered to remove insoluble material at the interface, then extracted with 2 N HCl (4×250 mL) followed by 3 N HCl (2×250 mL). The combined HCl extracts were back-extracted with EtOAc (500 mL) then filtered through Celite to remove insoluble material. The filtrate was cooled in an ice/brine bath, adjusted to pH 8 with a 6 N aqueous NaOH solution and extracted with EtOAc (3×1 L). The combined EtOAc extracts were washed with brine (1 L), dried over $Na_2SO_4$, stirred with charcoal (10 g) and silica gel (10 g) for 1 h. The mixture was filtered through Celite, washing the Celite pad with EtOAc (1 L). The filtrate was concentrated, co-evaporating residual EtOAc with n-heptane (500 mL). The resulting tan solid was pumped under high vacuum for 2 h to afford crude 6-chloro-5-(2-methoxyvinyl)pyrimidin-4-ylamine (Compound 11a, 72.3 g, 136.2 g theoretical, 53.1%). The crude desired product Compound 11a was used in the following reaction without further purification. A sample of crude product Compound 11a (2.3 g) was purified by silica gel column chromatography on, eluting with 0-35% EtOAc/n-heptane to give 1.7 g of pure 6-chloro-5-(2-methoxyvinyl)pyrimidin-4-ylamine (Compound 11a) as white solids, which was found to be a 1 to 2 mixture of E/Z isomers. For 6-Chloro-5-(2-methoxyvinyl)pyrimidin-4-ylamine: $^1H$ NMR (300 MHz, DMSO-$d_6$) for E-isomer: δ8.02 (s, 1H), 7.08 (bs, 2H), 6.92 (d, 1H, J=13.1), 5.35 (d, 1H, J=13.0 Hz), 3.68 (s, 3H) ppm and for Z-isomer: δ 8.06 (s, 1H), 7.08 (bs, 2H), 6.37 (d, 1H, J=6.8 Hz), 5.02 (d, 1H, J=6.7 Hz), 3.69 (s, 3H) ppm; $C_7H_8ClN_3O$ (MW, 185.61), LCMS (D) m/e 186/188 ($M^++H$).

Step 4. 4-Chloro-7H-pyrrolo[2,3-d]pyrimidine
(Compound 12a)

Concentrated aqueous hydrochloric acid (HCl, 5 mL) was added to a solution of crude 6-chloro-5-(2-methoxyvinyl)pyrimidin-4-ylamine (Compound 11a, 70.0 g, 0.3784 mol) in THF (700 mL) and the resulting reaction mixture was heated to reflux for 7.5 h. On warming a light suspension was formed that gradually re-dissolved.

When the reaction was deemed complete as monitored by HPLC, the reaction mixture was cooled to ambient temperature and stirred at ambient temperature for overnight. Solid $NaHCO_3$ (15 g) was added to the reaction mixture and the resulting mixture was stirred at ambient temperature for 1 h. Charcoal (7 g), silica gel (7 g) and $Na_2SO_4$ (20 g) were added and the mixture was heated to 40° C. for 1 h. The mixture was then cooled to ambient temperature and filtered through Celite, washing the Celite pad with THF (1 L). The filtrate was concentrated under reduced pressure and the resulting solid was dried under reduced pressure to afford crude 4-chloro-7H-pyrrolo[2,3-d]pyrimidine (Compound 12a, 58.1 g, 58.1 g theoretical, 100%) as yellow-brown solids. This crude desired product Compound 12 was dissolved in EtOAc (1.0 L) at 50-55° C. and treated with activated charcoal (3 g). The mixture was filtered while warm through Celite and the Celite pad was washed with warm EtOAc (250 mL). The filtrate was concentrated to about 500 mL and the suspension was allowed to stand at ambient temperature for overnight. The suspension was subsequently cooled to 0-5° C. for 2 h before the solids were collected by filtration. The solids were dried to afford pure 4-chloro-7H-[pyrrolo[2,3-d]pyrimidine (Compound 12a, 54.5 g, 58.1 g theoretical, 94%) as yellow-brown crystals. For Compound 12a: $^1$H NMR (400 MHz, DMSO-$d_6$) δ 12.58 (bs, 1H), 8.58 (s, 1H), 7.69 (d, 1H, J=3.5 Hz), 6.59 (d, 1H, J=3.5 Hz) ppm; LCMS (EI) m/e 154/156 (M$^+$+H).

Example 13: Alternative Preparation of 4-Chloro-7H-pyrrolo[2,3-d]pyrimidine (Compound 12a)

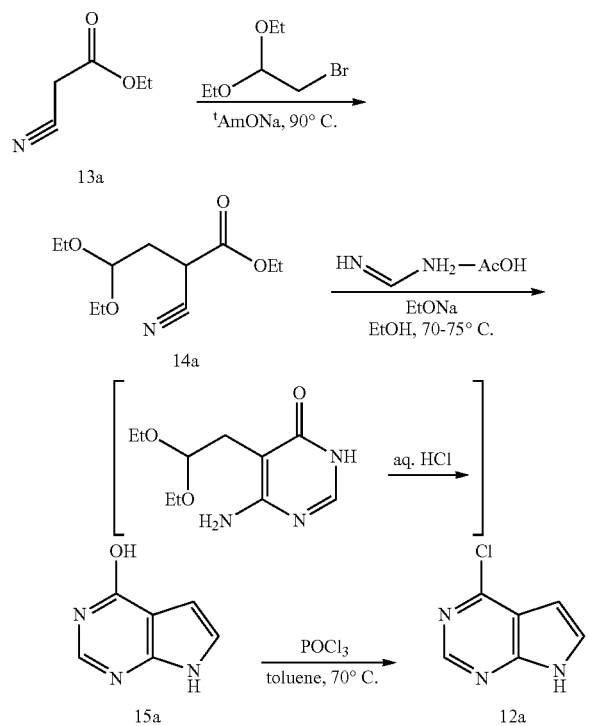

Step 1. Ethyl 2-cyano-4,4-diethoxybutanoate (Compound 14a)

To a mixture of ethyl cyanoacetate (Compound 13a, 182 Kg, 1609 moles) and DMSO (325 Kg) was added portionwise sodium tert-amyloxide ($^t$AmONa, 158.8 Kg) at 5° C. The mixture was then warmed to 70-75° C. and ethyl cyanoacetate (191 Kg, 1689 moles; total 3298 moles, 5.0 equiv) was charged. The mixture was stirred at 70-75° C. for 30 minutes before bromoacetaldehyde diethyl acetal (130.4 Kg, 665.2 moles) was added. The resulting reaction mixture was then heated to 90° C. and agitated at 90° C. until the reaction was complete. The reaction mixture was cooled to 5° C. and a 16% aqueous solution of ammonium chloride (NH$_4$Cl) was added. The mixture was agitated for 30 minutes before ethyl acetate (490 Kg) was charged. The organic phase was separated and washed with water (695 Kg). The aqueous phase was extracted with ethyl acetate (455 Kg). The combined organic phase was washed with a 17% aqueous solution of sodium chloride (NaCl, 318 Kg) and brine (325 Kg). The organic solution was dried over sodium sulfate (Na$_2$SO$_4$) and filtered. The filtrate was concentrated under reduced pressure. The residue was dissolved in petroleum ether (390 Kg) and treated with charcoal at 60° C. The mixture was filtered and the filtrate was concentrated to dryness to afford the crude ethyl 2-cyano-4,4-diethoxybutanoate (Compound 14a, 146.6 Kg, 152.5 Kg theoretical, 96.1%) as a yellow to brown oil, which was directly utilized in the subsequent reaction without further purification.

Step 2. 7H-Pyrrolo[2,3-d]pyrimidin-4-ol (Compound 15a)

To a reactor was charged a solution of 18% sodium ethoxide (EtONa) in ethanol (1558 Kg) and formamidine acetate (153.5 Kg, 1474.4 moles). The mixture was agitated at ambient temperature for 1 hour before ethyl 2-cyano-4,4-diethoxybutanoate (Compound 14a, 269.8 Kg, 1176.7 moles, 1.25 equiv) was charged. The reaction mixture was heated to 75° C. and agitated at 75° C. until no unreacted ethyl 2-cyano-4,4-diethoxybutanoate (Compound 14) was detected. The mixture was cooled to 0° C. and an aqueous solution of 21% ammonium chloride (NH$_4$Cl, 783 Kg) was charged. The resulting mixture was agitated at 0° C. for 30 minutes and concentrated under the reduced pressure. The residual solution was cooled to 20-30° C. and filtered. The cake was reslurried with water (493 Kg) and filtered. The solids were suspended in water (474 Kg) and the concentrated hydrochloric acid (HCl, 89.2 Kg) was added. The mixture was agitated at 20° C. for 1 hour and then warmed to 30° C. until the cyclization reaction was complete. The mixture was then cooled to 5° C. and an aqueous solution of ammonium hydroxide (NH$_4$OH, 72 Kg) was added. After addition, the mixture was agitated at 5° C. for 1 h and then filtered. The wet cake was washed with water and dried in a vacuum oven to afford 7H-Pyrrolo[2,3-d]pyrimidin-4-ol (Compound 15a, 99.6 Kg, 159 Kg theoretical, 62.6%) as off-white to yellow solids, which was used in the subsequent reaction without further purification.

Step 3. 4-Chloro-7H-pyrrolo[2,3-d]pyrimidine (Compound 12a)

7H-Pyrrolo[2,3-d]pyrimidin-4-ol (Compound 15a, 99.6 Kg, 737 moles) was added to a solution of DIEA (128.4 Kg, 99.5 3 moles, 1.35 equiv) in toluene (500 Kg) at ambient temperature and the resulting mixture was cooled to 0° C. POCl$_3$ (338 Kg, 2202 moles, 3.0 equiv) was then added to the mixture at 0° C. and the resulting reaction mixture was heated to 70° C. and agitated at 70° C. until the reaction was complete. The reaction mixture was cooled to 30° C. and added water (3500 Kg), sodium carbonate (Na$_2$CO$_3$, 700 Kg) and 2-methyltetrahydrofuran (MeTHF, 1200 Kg). The resulting mixture was then filtered. The organic phase of the filtrate was separated and washed with brine (424 Kg), dried over sodium sulfate (Na$_2$SO$_4$), and filtered. The filtrate was concentrated to remove approximately 1000 Kg of MeTHF. The remaining solution was treated with charcoal (28 Kg) at 60° C. for 1 hour and filtered. The filtrate was concentrated to a thick slurry, cooled to 0° C., and filtered. The cake was dried under reduced pressure to afford pure 4-chloro-7H- pyrrolo[2,3-d]pyrimidine (Compound 12a, 71.9 Kg, 113.2 Kg theoretical, 63.5%) as yellow to brown crystals. 4-Chloro-7H-pyrrolo[2,3-d]pyrimidine (Compound 12a) manufactured by this synthetic method is identical in every comparable aspect with the compound obtained by Example 12. $^1$H NMR (400 MHz, DMSO-$d_6$) δ 12.58 (bs, 1H), 8.58 (s, 1H), 7.69 (d, 1H, J=3.5 Hz), 6.59 (d, 1H, J=3.5 Hz) ppm; LCMS (EI) m/e 154/156 (M$^+$+H).

Example 14. Preparation of 4-Methyl-7H-pyrrolo[2,3-d]pyrimidine (Compound 1a)

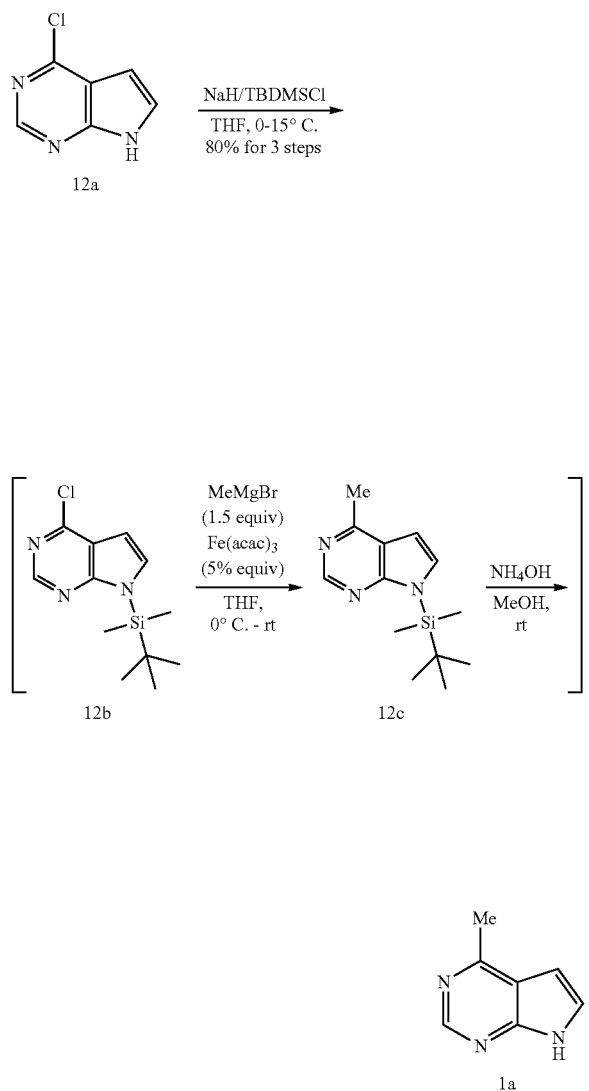

A suspension of sodium hydride (NaH, 60% suspension in mineral oil, 309, 7726 mmol, 1.211 equiv) in THF (4.0 L) was cooled to 0-5° C. in an ice bath before 4-chloro-7H-pyrrolo[2,3-d]pyrimidine (Compound 12a, 980.0 g, 6381 mmol) was charged. The mixture was agitated at 0-15° C. for 30 minutes before a solution of TBDMS-Cl (1165 g, 7728 mmol, 1.211 equiv) in THF was charged at 0-15° C. The resulting mixture was agitated at 0-15° C. for 1-2 hours. The mixture was cooled to −10° C. and Iron(III) acetylacetonate (Fe(acac)$_3$, 113 g, 319 mmol, 0.05 equiv) was charged. A solution of methylmagnesium bromide in THF (3260 mL, 9780 mmol, 1.53 equiv) was the slowly charged to the mixture and the internal temperature was controlled to below 15° C. The resulting reaction mixture was agitated at 15-30° C. for 2 hours. Once the coupling reaction was complete, an aqueous solution of ammonium chloride (NH$_4$Cl, 8.0 L) was charged to quench the reaction mixture and the internal temperature was controlled to below 10° C. during quenching. Methyl tert-butyl ether (MTBE, 5.0 L) was charged into the quenched reaction mixture and the resulting mixture was filtered through a Celite bed. The Celite bed was washed with MTBE (2×500 mL). The two phases of the combined filtrate and wash solution were separated and the aqueous phase was extracted with MTBE (2×5.0 L). The combined organic extracts were concentrated under the reduced pressure and the residue was dissolved in methanol (MeOH, 5.0 L). The solution was then treated with an aqueous solution of 26-28% ammonium hydroxide (NH$_4$OH, 1.0 L) and the resulting mixture was agitated at 15-40° C. for 16 hours. When the N-TBDMS-deprotection reaction was complete, the reaction mixture was concentrated under reduced pressure and n-heptane (2×4.0 L) was charged to remove water under the azeotropic conditions. The residue was then treated with n-heptane (8.0 L) and the resulting mixture was agitated at ambient temperature for at least one hour. The solids were collected by filtration and washed with n-heptane (2×1.0 L) to afford the crude desired product, 4-methyl-7H-pyrrolo[2,3-d]pyrimidine (Compound 1a, 840 g, 849.6 g theoretical, 98.9%), as brown powders, which was purified by recrystallization in a mixture of ethyl acetate and n-heptane.

A solution of crude methyl-7H-pyrrolo[2,3-d]pyrimidine (Compound 1a, 1640 g) in methanol (MeOH, 8.0 L) was treated with charcoal (2.0 Kg) and the resulting mixture was agitated at ambient temperature for 16 hours. The mixture was filtered through a Celite bed and the Celite bed was washed with MeOH (2×8.0 L). The combined methanol solution was concentrated under the reduced pressure and the residue was added ethyl acetate (8.0 L). The resulting solution was concentrated under the reduced pressure to remove most of ethyl acetate (approximately 6.0 L) before n-heptane (8.0 L) was introduced. The resulting mixture was agitated at ambient temperature for 14 hours. The solids were collected by filtration, washed by a mixture of ethyl acetate and n-heptane followed by n-heptane, and dried to constant weight to afford the purified methyl-7H-pyrrolo[2, 3-d]pyrimidine (Compound 1a, 1325 g, 1640 g theoretical, 80.8% for purification by recrystallization and 80% for overall) as yellow to light brown crystalline powders. For Compound 1a: $^1$H NMR (DMSO-$d_6$, 500 MHz) δ12.10 (br s, 1H), 8.61 (s, 1H), 7.47 (dd, J=3.3, 2.5 Hz, 1H), 6.62 (s, dd, J=3.5, 1.7 Hz, 1H), 2.64 (s, 3H) ppm; $^{13}$C NMR (DMSO-$d_6$, 125 MHz) δ 158.7, 151.3, 151.2, 126.5, 117.6, 99.6, 21.3 ppm; C$_7$H$_7$N$_3$(MW, 133.15) LCMS (EI) m/e 134.1 (M$^+$+H, base peak).

Example 15. Alternative Preparation of 4-Methyl-7H-pyrrolo[2,3-d]pyrimidine (Compound 1a)

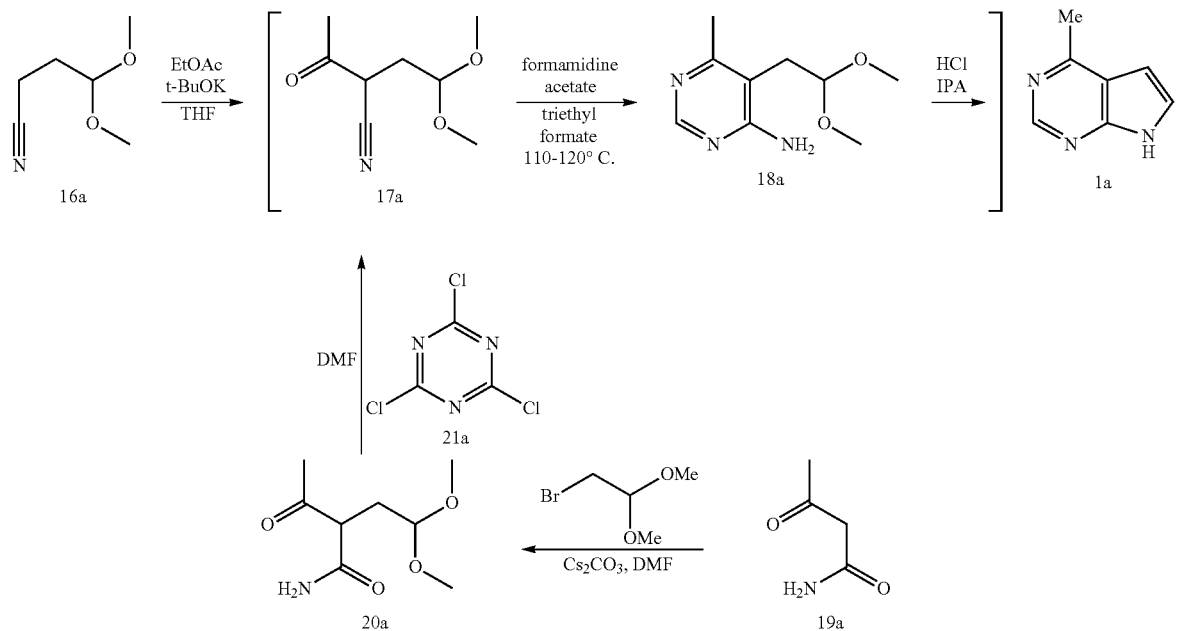

Step 1. 4-Methyl-7H-pyrrolo[2,3-d]pyrimidine (Compound 1a)

A turbid mixture of potassium tert-butoxide (18.31 g, 163 mmol, 2.12 equiv) in THF (100 mL) was cooled in an ice bath before a solution of 4,4-dimethoxybutanenitrile (Compound 16a, 10.00 g, 77 mmol) and ethyl acetate (7.46 g, 85 mmol, 1.1 equiv) in THF (20 mL) were charged over 15 minutes. The mixture was allowed to warm to room temperature and stirred at ambient temperature for 3 hours. 2-Acetyl-4,4-dimethoxybutanenitrile, generated in situ, was then treated with formamidine acetate (65.0 g, 624 mmol, 8.1 equiv), 1-butanol (80 mL) and triethyl orthoformate (56.2 mL, 337 mmol, 4.38 equiv) at ambient temperature. The resulting mixture was heated to 110-120° C. and stirred at 110-120° C. for 1 hour. Additional triethyl orthoformate (26.5 mL, 159 mmol, 2.06 equiv) was added. The mixture was stirred at 110° C. for additional 16 hours. Additional formamidine acetate (31.38 g, 302 mmol, 3.92 equiv) and triethyl orthoformate (56.5 mL, 115 mmol, 1.5 equiv) were added in three portions over 24 hours. The mixture was heated for an additional 24 hours and concentrated under the reduced pressure to a residue. The residue was treated with water (150 mL) and MeTHF (210 mL). The resulting mixture was passed through a bed of Celite (12 g). Two phases of the filtrate were separated and the aqueous phase was extracted with MeTHF (175 mL×2). The combined organic extracts were concentrated under the reduced pressure, and the resulting residue was treated a solution of HCl in IPA (5.5 M, 50.8 g), water (31 mL), and concentrated HCl (12 M, 15.6 g). The mixture was stirred at room temperature for 3 days. A concentrated aqueous NH$_4$OH solution (38.6 g, 28-30%) was added and the mixture was concentrated to a residue, which was triturated with THF (170 mL, 2×150 mL). Filtrates were combined and concentrated to a residue, which was dissolved in DCM (30 mL) and purified by column chromatography over silica gel (SiO$_2$, 120 g), eluting with 0-100% of EtOAc in DCM, to afford the desired product, 4-methyl-7H-pyrrolo[2,3-d]pyrimidine (Compound 1a, 5.1 g, 10.25 g theoretical, 49.8% for three steps), as an off-white crystalline solid, which is identical in every comparable aspect with the compound obtained by Example 14.

Step 2. 2-Acetyl-4,4-dimethoxybutanamide (Compound 20a)

A solution of 3-oxobutanamide (Compound 19a, 5.0 g, 49.5 mmol) in DMF (15 mL) was treated with cesium carbonate (Cs$_2$CO$_3$, 16.11 g, 49.5 mmol, 1.0 equiv) at ambient temperature. The resulting mixture was stirred at ambient temperature. 2-Bromo-1,1-dimethoxyethane (8.36 g, 49.5 mmol, 1.0 equiv) was then added to the mixture and the resulting reaction mixture was heated to 80° C. for 5-8 hours. The reaction mixture was cooled to ambient temperature and then quenched with water (20 mL). The quenched reaction mixture was then extracted with ethyl acetate (3×20 mL) and the combined organic extracts were washed with water (2×10 mL), dried with anhydrous sodium sulfate (Na$_2$SO$_4$), and concentrated under reduced pressure. The residue was purified by silica gel (SiO$_2$) column chromatography to afford 2-acetyl-4,4-dimethoxybutanamide (Compound 20a, 5.8 g, 9.37 g theoretical, 61.9%) as a thick oil, which contains some residual DMF. For 2-acetyl-4,4-dimethoxybutanamide: $^1$H NMR (DMSO-d$_6$, 400 MHz) δ 6.70 (s, 1H), 6.30 (s, 1H), 4.28 (dd, 1H), 3.47 (t, 1H), 3.23 (s, 6H), 2.25 (s, 3H), 2.19, (m, 1H), 2.00 (m 1H); C$_8$H$_{15}$NO$_4$ (MW, 189.21), LCMS (EI) m/e 190.2 (M$^+$+H).

Step 3. 2-Acetyl-4,4-dimethoxybutanenitrile (Compound 17a)

A solution of 2-acetyl-4,4-dimethoxybutanamide (Compound 20a, 1.0 g, 4.23 mmol) in DMF (4 mL) was treated with cyanuric chloride (Compound 21a, 0.39 g, 2.11 mmol, 0.5 equiv). The resulting reaction mixture was stirred at ambient temperature for 1 h. Once the reaction was complete, the reaction mixture was quenched with water (10 mL) and the quenched reaction mixture was extracted with ethyl acetate (3×10 mL). The combined organic extracts were washed with water (2×10 mL), dried with anhydrous sodium sulfate ($Na_2SO_4$), and concentrated under reduced pressure. The residue was purified by silica gel ($SiO_2$) column chromatography to afford 2-acetyl-4,4-dimethoxybutanenitrile (Compound 17a, 280 mg, 724 mg theoretical, 38.7%) as a thick oil. For 2-acetyl-4,4-dimethoxybutanenitrile: $^1H$ NMR (DMSO-$d_6$, 400 MHz, a mixture of ketone and enol forms obtained) δ 10.7 (br. s, ½ H for enol form of —OH), 4.38 (m, 1H), 3.25 (m, 6H for two OMe and ½ H for ketone form of —CH—), 2.25-2.50 (m, 2H), 2.15 and 2.25 (s, 3H); $C_8H_{13}NO_3$ (MW, 171.196), LCMS (EI) m/e 172.2 (M$^+$+H). 2-Acetyl-4,4-dimethoxybutanenitrile (Compound 17a) generated by this method reacts with formamidine acetate followed by treatment with HCl to afford 4-methyl-7H-pyrrolo[2,3-d]pyrimidine (Compound 1a) according to Example 14 described above.

Example 16. Preparation of 4-Methyl-(7H-pyrrolo[2,3-d]pyrimidin-4-yl) hydrochloride (Compound 1a hydrochloride)

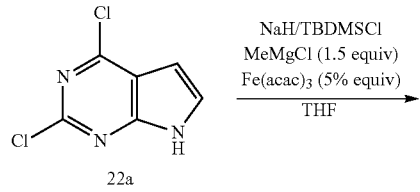

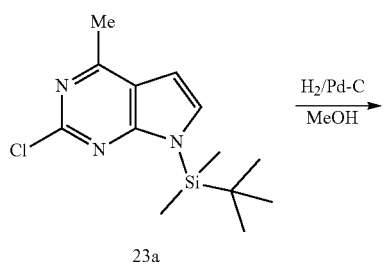

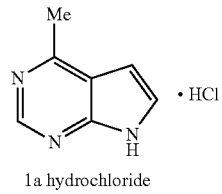

To a reactor under nitrogen were charged 2,4-dichloro-7H-pyrrolo[2,3-d]pyrimidine (Compound 22a, 200 g, 1.064 mole) and THF (1.2 L). The content in the reactor was cooled to below −5° C. before 60% NaH in mineral oil (51 g, 1.28 moles, 1.2 equiv) was added portion wise. During addition of NaH, the internal temperature was maintained at −5 to 5° C. After the addition, agitation was continued for 30 minutes and then a solution of TBDMS-Cl (193 g, 1.28 moles, 1.2 equiv) in THF (200 mL) was added slowly by keeping the internal temperature at −5 to 5° C. Agitation of the reaction mixture was continued for 30 minutes and Fe(acac)$_3$ (18.8 g, 53. 2 mmol, 0.05 equiv) was then added followed by the addition of a 3.0 M solution of MeMgCl in THF (532 mL, 1.596 moles, 1.5 equiv) at −5 to 5° C. After the reaction mixture was kept for an additional 1 h, by which time IPC by HPLC showed the completion of the coupling reaction, the reaction mixture was poured into a solution of EDTA di-sodium salt dihydrate (200 g) in water (2.0 L) while the internal temperature was controlled at below 15° C. The biphasic mixture was diluted with methyl tert-butyl ether (MTBE, 2.0 L), treated with Celite (150 g), and filtered by centrifuge. The solid cake was washed with MTBE and the filtrate was allowed for phase separation. The aqueous phase was separated and extracted with MTBE (1.0 L). The organic phase was combined and washed successively with 3% citric acid aqueous solution (2×400 mL) and brine (600 mL). After being dried over $Na_2SO_4$, the organic phase was filtered and concentrated to dryness. The residue was taken up with petroleum ether (2.0 L) and any insoluble materials were removed by filtration through a thin layer of silica gel. The filtrate was concentrated to give the crude desired product, 7-(tert-butyldimethylsilyl)-2-chloro-4-methyl-7H-pyrrolo[2,3-d]pyrimidine (Compound 22a, 300 g), as an oily residue, which was used directly in the subsequent reaction without further purification.

A mixture of crude 7-(tert-butyldimethylsilyl)-2-chloro-4-methyl-7H-pyrrolo[2,3-d]pyrimidine (Compound 22a, 300 g, 1.064 moles) and 5% palladium on carbon (Pd/C, 30 g) in methanol (1.8 L) was vigorously agitated under 1 atm of hydrogen at 50-55° C. for 3 hours. After IPC by HPLC confirmed the completion of the reaction, the reaction mixture was cooled to 20-25° C. and filtered. The filter cake was washed with methanol and the filtrate was concentrated to dryness. The residue was suspended in ethyl acetate (EtOAc, 225 mL) and agitated at 10-15° C. for 1 hour. The solids were collected by filtration, washed with ethyl acetate and dried under vacuum at 40-45° C. to give 4-methyl-7H-pyrrolo[2,3-d]pyrimidine hydrochloride (Compound 1a hydrochloride, 151.5 g, 180.5 g theoretical, 84% yield for two steps) as light yellow crystalline powders. For Compound 1a hydrochloride: $^1H$ NMR (DMSO-$d_6$, 500 MHz) δ ppm 13.54 (br s, 1H), 9.04 (s, 1H), 7.95 (dd, J=3.4, 2.4 Hz, 1H), 7.13 (s, dd, J=3.4, 1.5 Hz, 1H), 2.97 (s, 3H); $^{13}C$ NMR (DMSO-$d_6$, 125 MHz) δ ppm 154.0, 151.0, 144.0, 131.6, 117.2, 103.1, 17.6; $C_7H_8ClN_3$(MW, 169.61; $C_7H_7N_3$ for free base, MW 133.15) LCMS (EI) mle 134.1 (M$^+$+H, base peak).

Example 17. Preparation of Sodium 2-(7H-pyrrolo[2,3-d]pyrimidin-4-yl)acetate (5b) and 2-(7H-pyrrolo[2,3-d]pyrimidin-4-yl)acetic acid (Compound 5a)

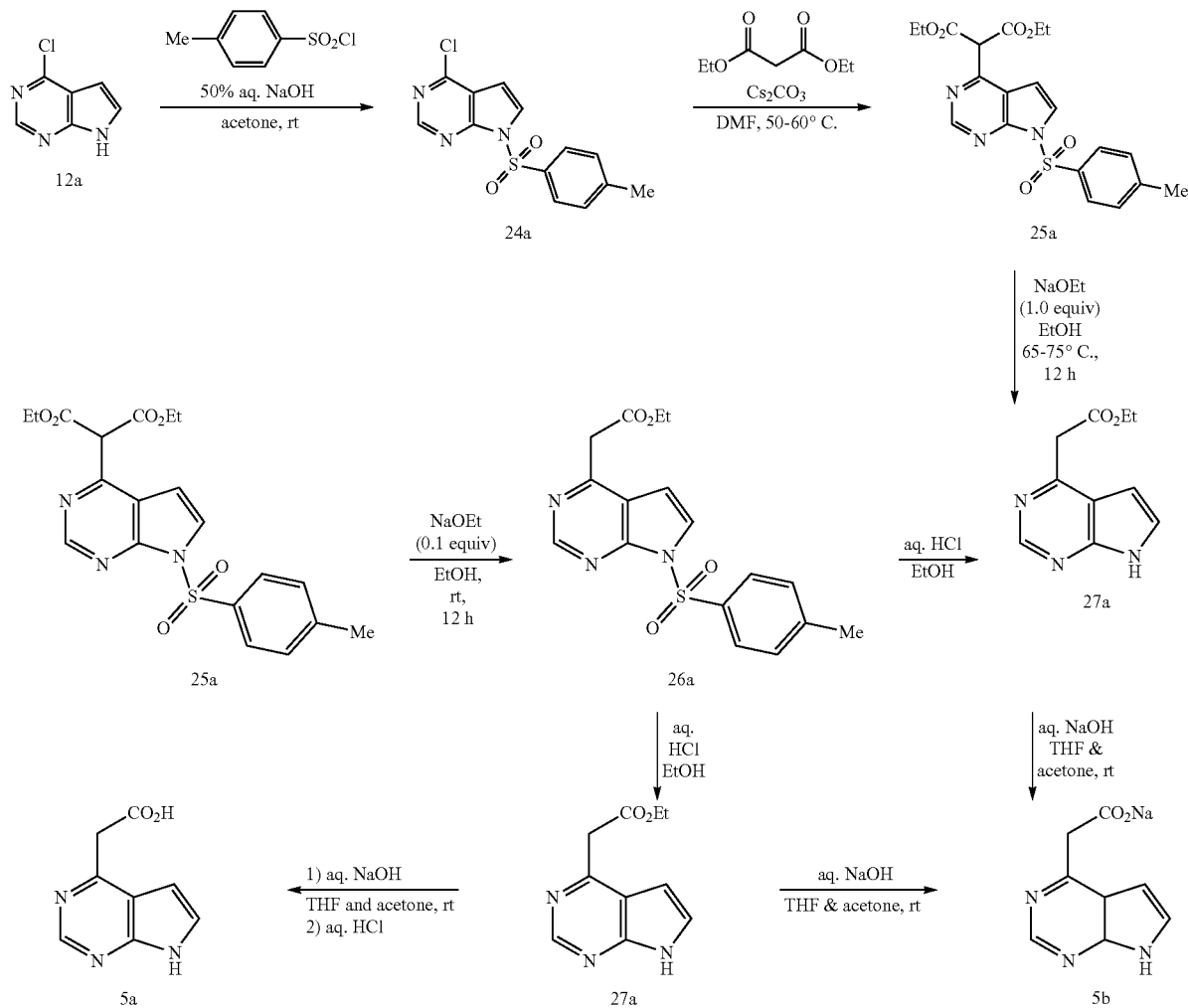

Step 1. 4-Chloro-7-tosyl-7H-pyrrolo[2,3-d]pyrimidine (Compound 24a):

A suspension of 4-chloro-7H-pyrrolo[2,3-d]pyrimidine (Compound 12a, 18.0 g, 117 mmol) in acetone (180 mL) was added a 50% aqueous sodium hydroxide solution (NaOH, 14.07 g, 176 mmol, 1.5 equiv) at ambient temperature. The resulting mixture was then agitated at ambient temperature until a clear solution was generated. p-Toluenesulfonyl chloride (pTsCl, 25.7 g, 135 mmol, 1.15 equiv) was added to the solution at ambient temperature and the resulting reaction mixture was agitated at ambient temperature for 1 hour. When the reaction was complete, the reaction mixture was filtered, and the solids were washed with acetone before being discarded. The filtrate was then concentrated under the reduced pressure, and the residue was treated with methyl tert-butyl ether (MTBE, 180 mL) and n-heptane (180 mL). The resulting mixture was agitated at ambient temperature for 1 hour. The solids were collected by filtration, washed with n-heptane (180 mL), and dried in the vacuum oven to the constant weight to afford the desired product, 4-chloro-7-tosyl-7H-pyrrolo[2,3-d]pyrimidine (Compound 24a, 32.1 g, 36.0 g theoretical, 89.2% yield), as off-white powders, which was used in the subsequent reactions without further purification. For 4-Chloro-7-tosyl-7H-pyrrolo[2,3-d]pyrimidine: $^1$H NMR (DMSO-$d_6$, 400 MHz) δ 8.78 (s, 1H), 8.10 (d, 2H), 7.79 (d, 1H), 7.34 (d, 2H), 6.72 (d, 1H), 2.41 (s, 3H) ppm; $C_{13}H_{10}ClN_3O_2S$ (MW, 307.75), LCMS (EI) m/e 308.1 (M$^+$+H).

Step 2. Diethyl 2-(7-tosyl-7H-pyrrolo[2,3-d]pyrimidin-4-yl)malonate (Compound 25a)

A solution of 4-chloro-7-tosyl-7H-pyrrolo[2,3-d]pyrimidine (Compound 24a, 7.0 g, 22.75 mmol) and diethyl malonate (5,46 g, 34.1 mmol, 1.5 equiv) in anhydrous DMF (30 mL) was treated with solid cesium carbonate ($Cs_2CO_3$, 18.53 g, 56.9 mmol, 2.5 equiv) at ambient temperature. The resulting reaction mixture was them warmed to 50-60° C. and agitated at 50-60° C. for 2-3 hours. When the reaction was complete, the reaction mixture was cooled to ambient temperature before being treated with water (H₂O, 80 mL). The quenched reaction mixture was then agitated at ambient temperature for 1 hour followed by at 0-5° C. for 1 hour. The solids were collected by filtration, washed with water (50 mL) followed by n-heptane (50 mL), and dried in the vacuum oven at 40° C. to constant weight to afford the desired product, diethyl 2-(7-tosyl-7H-pyrrolo[2,3-d]pyrimidin-4-yl)malonate (Compound 25a, 6.2 g, 9.81 g theoretical, 63.2% yield), as off-white powders, which were used in the subsequent reactions without further purification. For Diethyl 2-(7-tosyl-7H-pyrrolo[2,3-d]pyrimidin-4-yl)malonate: $^1$H NMR (CDCl₃, 400 MHz) δ 8.98 (s, 1H), 8.12 (d, 2H), 7.77 (d, 1H), 7.34 (d, 2H), 6.72 (d, 1H), 5.10 (s, 1H), 4.25 (m, 4H), 2.42 (s, 3H), 1.27 (m, 6H) ppm; $C_{20}H_{21}N_3O_6S$ (MW, 431.46), LCMS (EI) m/e 432.3 (M⁺+H).

Step 3. Ethyl 2-(7-tosyl-7H-pyrrolo[2,3-d]pyrimidin-4-yl)acetate (Compound 26a)

A solution of diethyl 2-(7-tosyl-7H-pyrrolo[2,3-d]pyrimidin-4-yl)malonate (Compound 25a, 4.0 g, 9.27 mmol) in ethanol (EtOH, 20 mL) was treated with a solution of 21% sodium ethoxide in ethanol (NaOEt, 21 wt %, 0.30 g, 0.927 mmol, 0.10 equiv) at ambient temperature and the resulting reaction mixture was agitated at ambient temperature for 12 hours. The reaction mixture was quenched with a 0.1 N aqueous hydrochloric acid solution (10 mL) and the resulting mixture was concentrated under the reduced pressure. The residue was then purified by the silica gel (SiO₂) column chromatography to afford the desired product, ethyl 2-(7-tosyl-7H-pyrrolo[2,3-d]pyrimidin-4-yl)acetate (Compound 26a, 2.08 g, 3.33 g theoretical, 62.6% yield), as off-white powders, which were used in the subsequent reaction without further purification. For Ethyl 2-(7-tosyl-7H-pyrrolo[2,3-d]pyrimidin-4-yl)acetate: $^1$H NMR (CDCl₃, 400 MHz) δ 8.96 (s, 1H), 8.11 (d, 2H), 7.75 (d, 1H), 7.33 (d, 2H), 6.70 (d, 1H), 4.19 (q, 2H), 4.30 (s, 2H), 2.41 (s, 3H), 1.25 (t, 3H) ppm; $C_{17}H_{17}N_3O_4S$ (MW, 359.40), LCMS (EI) m/e 360.2 (M⁺+H).

Step 4. Ethyl 2-(7H-pyrrolo[2,3-d]pyrimidin-4-yl) acetate (Compound 27a)

A solution of diethyl 2-(7-tosyl-7H-pyrrolo[2,3-d]pyrimidin-4-yl)malonate (Compound 25a, 4.0 g, 9.27 mmol) in ethanol (EtOH, 20 mL) was treated with a solution of 21% sodium ethoxide in ethanol (NaOEt, 21 wt %, 3.0 g, 9.27 mmol, 1.0 equiv) at ambient temperature. The resulting reaction mixture was heated to 65-75° C. and agitated at 65-75° C. for 12 hours. The reaction mixture was quenched with a 1.0 N aqueous hydrochloric acid solution and the resulting mixture was concentrated under the reduced pressure. The residue was then purified by the silica gel (SiO₂) column chromatography to afford the desired product, ethyl 2-(7H-pyrrolo[2,3-d]pyrimidin-4-yl)acetate (Compound 27a, 1.3 g, 1.9 g theoretical, 68.3% yield), as off-white powders, which were used in the subsequent reactions without further purification. For Ethyl 2-(7H-pyrrolo[2,3-d]pyrimidin-4-yl)acetate: $^1$H NMR (CDCl₃, 400 MHz) δ 11.40 (br s, 1H), 8.90 (s, 1H), 7.42 (d, 1H), 6.65 (d, 1H), 4.23 (q, 2H), 4.13 (s, 2H), 1.27 (t, 3H) ppm; $C_{10}H_{11}N_3O_2$(MW, 205.22), LCMS (EI) m/e 206.2 (M⁺+H).

Step 5. Sodium 2-(7H-pyrrolo[2,3-d]pyrimidin-4-yl) acetate (Compound 5b)

A solution of ethyl 2-(7H-pyrrolo[2,3-d]pyrimidin-4-yl) acetate (Compound 27a,1.2 g, 5.85 mmol) in acetone (10 mL) and THF (10 mL) was treated with an aqueous solution of 6 N sodium hydroxide (6 N NaOH, 1.462 mL, 8.77 mmol, 1.5 equiv) at ambient temperature. The resulting reaction mixture was agitated at ambient temperature for 5 hours. The solids were collected by filtration and the isolated solids were suspended in methanol (MeOH, 4.0 mL). The resulting suspension was then added acetone (15 mL) and the mixture was agitated at ambient temperature for 1 hour. The solids were collected by filtration, washed with acetone (2×5 mL), and dried under vacuum to afford the desired product, sodium 2-(7H-pyrrolo[2,3-d]pyrimidin-4-yl)acetate (Compound 5b, 1.1 g, 1.164 g theoretical, 94.5% yield), as off-white powders, which was used in the subsequent reaction without further purification. For Sodium 2-(7H-pyrrolo[2,3-d]pyrimidin-4-yl)acetate: $^1$H NMR (DMSO-d₆, 400 MHz) δ 8.36 (s, 1H), 7.37 (d, 1H), 6.40 (d, 1H), 3.61 (s, 2H) ppm; $C_8H_6N_3NaO_2$ (MW, 199.15; $C_8H_7N_3O_2$ for the corresponding acid, MW 177.16), LCMS (EI) m/e 178.1 (M⁺+H).

Step 6. 2-(7H-Pyrrolo[2,3-d]pyrimidin-4-yl)acetic acid (Compound 5a):

A solution of ethyl 2-(7H-pyrrolo[2,3-d]pyrimidin-4-yl) acetate (Compound 27a, 1.2 g, 5.85 mmol) in acetone (10 mL) and THF (10 mL) was treated with an aqueous solution of 6 N sodium hydroxide (6 N NaOH, 1.462 mL, 8.77 mmol, 1.5 equiv) at ambient temperature. The resulting reaction mixture was agitated at ambient temperature for 5 hours. The reaction mixture was then treated with a solution of 1 N aqueous hydrochloric acid (1 N HCl, 9.0 mL) before being concentrated under the reduced pressure. The residue was then purified by the silica gel (SiO₂) column chromatography to afford the desired product, 2-(7H-pyrrolo[2,3-d] pyrimidin-4-yl)acetic acid (Compound 5a, 0.83 g, 1.04 g theoretical, 79.8% yield), as off-white solids, which were used in the subsequent reaction without further purification. For 2-(7H-pyrrolo[2,3-d]pyrimidin-4-yl)acetic acid: $^1$H NMR (DMSO-d₆, 400 MHz) δ 12.01 (br s, 1H), 8.56 (s, 1H), 7.36 (d, 1H), 6.57 (d, 1H), 3.66 (s, 2H) ppm; $C_8H_7N_3O_2$ (MW, 177.16), LCMS (EI) m/e 178.1 (M⁺+H).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A process of preparing baricitinib, or a salt thereof, comprising:

reacting a compound of formula 3:

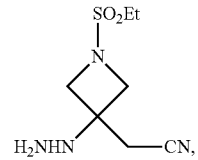

or a salt thereof, with a reagent which is selected from: (i) a salt of formula 2a, and (ii) a compound of formula 2b:

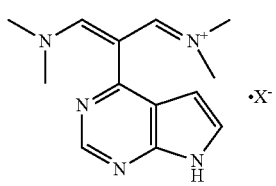

wherein X⁻ is a counter anion.

2. The process of claim 1, wherein the reagent is the compound of formula 2b.

3. The process of claim 1, wherein the salt of formula 2a, or the compound of formula 2b is prepared by a process comprising:

reacting a compound of formula 1a:

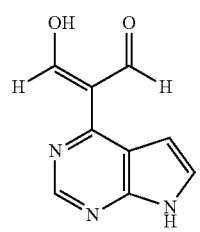

or a salt thereof, with a Vilsmeier reagent formed from dimethylformamide.

4. The process of claim 3, wherein the Vilsmeier reagent is prepared by a process comprising reacting dimethylformamide with a chlorinating agent.

5. The process of claim 4, wherein the chlorinating agent is selected from oxalyl chloride, phosphorus oxychloride, triphosgene, thionyl chloride, sulfuryl chloride, and phosphorus pentachloride.

6. The process of claim 3, wherein the product of the reacting with the Vilsmeier reagent is a salt of formula 2d:

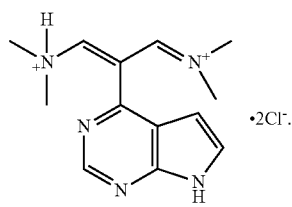

7. The process of claim 6, further comprising reacting the salt of formula 2d with a base to form a salt of formula 2c:

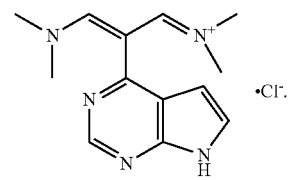

8. The process of claim 3, wherein the product of the reacting with the Vilsmeier reagent is a salt of formula 2c:

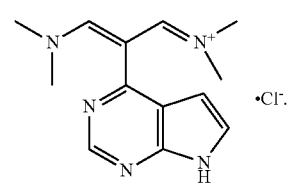

9. The process of claim 8, further comprising reacting the salt of formula 2c with a salt of formula M⁺X⁻ to form the salt of formula 2a, wherein:

M⁺ is a counter cation; and

X⁻ is a counter anion other than Cl⁻.

10. The process of claim 3, wherein the compound of formula 1a, or the salt thereof, is prepared by a process comprising:

deprotecting a compound of formula 1aP:

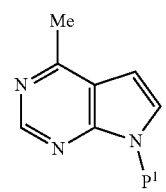

wherein P¹ is an amino protecting group.

11. The process of claim 10, wherein the compound of formula 1aP is prepared by a process comprising:

reacting a compound of formula 2P:

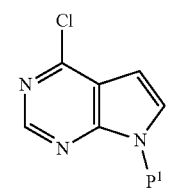

with MeMgBr in the presence of a Grignard catalyst, wherein P¹ is an amino protecting group.

12. The process of claim 11, wherein the compound of formula 2P is prepared by a process comprising:

protecting a compound of formula 12a:

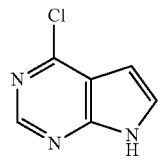

12a to form the compound of formula 2P.

13. The process of claim 12, wherein the compound of formula 12a is prepared by a process comprising:

reacting a compound of formula 11a:

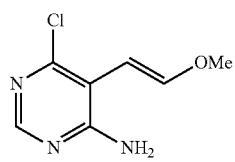

11a or a salt thereof, with a strong acid.

14. The process of claim 13, wherein the compound of formula 11a, or a salt thereof, is prepared by a process comprising:

reacting a compound of formula 10a:

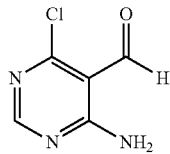

10a or a salt thereof, with (methoxymethyl)triphenylphosphonium chloride and a base.

15. The process of claim 14, wherein the compound of formula 10a, or a salt thereof, is prepared by a process comprising:

reacting a compound of formula 9a:

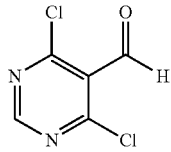

9a with ammonia.

16. The process of claim 15, wherein the compound of formula 9a is prepared by a process comprising:

reacting a compound of formula 8a:

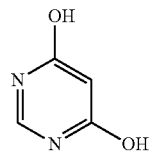

8a with a Vilsmeier reagent formed from dimethylformamide.

17. The process of claim 12, wherein the compound of formula 12a is prepared by a process comprising:

reacting a compound of formula 15a:

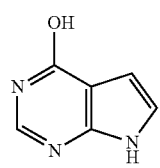

15a with a chlorinating agent.

18. The process of claim 17, wherein the compound of formula 15a is prepared by a process comprising:

(i) reacting a compound of formula 14a:

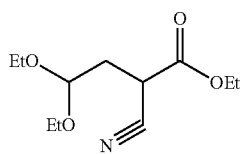

14a with formamidine acetate and an alkali metal alkoxide to generate a compound of formula 14aa:

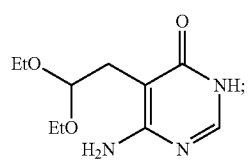

14aa and (ii) reacting the compound of formula 14aa with a strong acid.

19. The process of claim 18, wherein the compound of formula 14a is prepared by a process comprising:

reacting a compound of formula 13a:

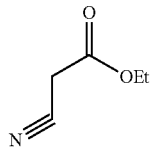

13a with bromoacetaldehyde diethyl acetal and sodium tert-amyloxide.

20. The process of claim 3, wherein the compound of formula 1a, or the salt thereof, is prepared by a process comprising:

reducing a compound of formula 23P:

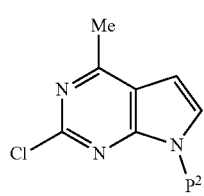

23P wherein $P^2$ is an amino protecting group.

21. The process of claim 20, wherein the compound of formula 23P is prepared by a process comprising:

reacting a compound of formula 22P:

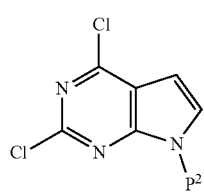

22P with MeMgCl in the presence of a Grignard catalyst, wherein $P^2$ is an amino protecting group.

22. The process of claim 21, wherein the compound of formula 22P is prepared by a process comprising:

protecting a compound of formula 22a:

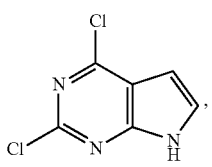

22a to form the compound of formula 22P.

23. The process of claim 22, wherein the compound of formula 1a, or the salt thereof, is prepared by a process comprising:

reacting a compound of formula 18a:

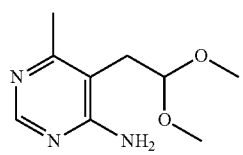

18a with an acid to form the compound of formula 1a, or the salt thereof.

24. The process of claim 23, wherein the compound of formula 18a is prepared by a process comprising:

reacting a compound of formula 17a:

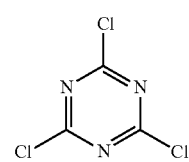

17a with formamidine acetate and triethyl orthoformate to form the compound of formula 18a.

25. The process of claim 24, wherein the compound of formula 17a is prepared by a process comprising:

reacting a compound of formula 20a:

20a with a compound of formula 21a:

21a to form the compound of formula 17a.

26. The process of claim 1, wherein the salt of formula 2a or the compound of formula 2b is prepared by a process comprising:

reacting a compound of formula 5a:

or a salt thereof, with a Vilsmeier reagent formed from dimethylformamide.

27. The process of claim 1, wherein the compound of formula 3, or a salt thereof, is formed by a process comprising:

reacting a compound of formula 6:

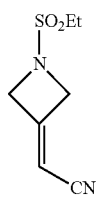

with hydrazine.

28. A process of preparing baricitinib, or a salt thereof, comprising reacting a salt of formula 2c:

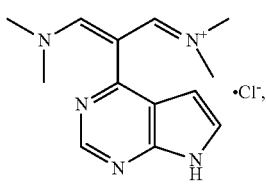

with a compound of formula 3:

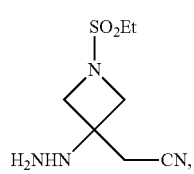

to form the baricitinib, or the salt thereof.

29. The process of claim 28, wherein the salt of formula 2c is prepared by a process, comprising reacting a salt of formula 2d:

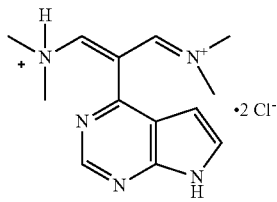

with a base to form the salt of formula 2c.

30. The process of claim 29, wherein the salt of formula 2d is prepared by a process comprising:

(a) reacting a compound of formula 2P:

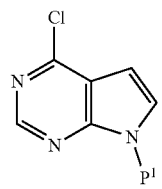

with MeMgBr in the presence of a Grignard catalyst to form a compound of formula 1aP:

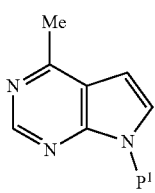

(b) deprotecting the compound of formula 1aP to form a compound of formula 1a:

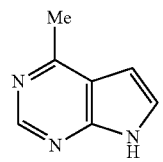

or a salt thereof; and (c) reacting the compound of formula 1a, or the salt thereof, with a Vilsmeier reagent formed from dimethylformamide and a chlorinating agent to form the salt of formula 2d;

wherein $P^1$ is an amino protecting group.

31. The process of claim 28, wherein the compound of formula 3, or the salt thereof, is prepared by a process comprising:
reacting a compound of formula 6:
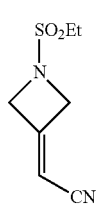
6
with hydrazine.
* * * * *